(12) United States Patent
Teufel et al.

(10) Patent No.: US 10,870,679 B2
(45) Date of Patent: Dec. 22, 2020

(54) MODULATION OF STRUCTURED POLYPEPTIDE SPECIFICITY

(71) Applicant: BicyleRD Limited, Cambridge (GB)

(72) Inventors: Daniel Paul Teufel, Cambridge (GB); Catherine Stace, Cambridge (GB); Edward Walker, Cambridge (GB); John Tite, Cambridge (GB)

(73) Assignee: BicycleRD Limited, Cambridge (GB)

( * ) Notice: Subject to any disclaimer, the term of this patent is extended or adjusted under 35 U.S.C. 154(b) by 3 days.

(21) Appl. No.: 16/013,795

(22) Filed: Jun. 20, 2018

(65) Prior Publication Data

US 2018/0362585 A1    Dec. 20, 2018

Related U.S. Application Data

(63) Continuation of application No. 14/781,294, filed as application No. PCT/EP2014/057440 on Apr. 11, 2014, now Pat. No. 10,118,947.

(30) Foreign Application Priority Data

Apr. 11, 2013    (GB) .................................. 1306623.8

(51) Int. Cl.
| | | |
|---|---|---|
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 7/08* | (2006.01) | |
| *C07K 7/54* | (2006.01) | |
| *C12N 9/64* | (2006.01) | |
| *C07K 7/50* | (2006.01) | |
| *C07K 7/06* | (2006.01) | |

(52) U.S. Cl.
CPC ................. *C07K 7/08* (2013.01); *C07K 7/06* (2013.01); *C07K 7/50* (2013.01); *C07K 7/54* (2013.01); *C12N 9/6445* (2013.01)

(58) Field of Classification Search
None
See application file for complete search history.

(56) References Cited

U.S. PATENT DOCUMENTS

| 10,118,947 B2 * | 11/2018 | Teufel .................. C12N 9/6445 |
|---|---|---|
| 2010/0317547 A1 | 12/2010 | Winter et al. |
| 2013/0316950 A1 * | 11/2013 | Popel ..................... C07K 14/78 514/13.3 |
| 2014/0256590 A1 | 9/2014 | Wurdinger et al. |
| 2014/0256596 A1 * | 9/2014 | Tite .......................... C07K 1/00 506/18 |
| 2016/0046673 A1 | 2/2016 | Tuefel et al. |
| 2016/0222063 A1 | 8/2016 | Teufel et al. |

FOREIGN PATENT DOCUMENTS

| EP | 2474613 B1 | 7/2014 |
|---|---|---|
| WO | WO 2006/078161 A1 | 7/2006 |
| WO | WO 2013/050615 A1 | 4/2013 |
| WO | WO 2013/050616 A1 | 4/2013 |

OTHER PUBLICATIONS

Gentilucci et al., Curr. Pharma. Design 16:3185-3203 (2010) (Year: 2010).*
Angelini et al., Bioconjugate Chem. 23:1856-1863 (2012) (Year: 2012).*
"Tryptophan" available online at http://www.russelllab.org/aas/Trp.html, 2 pages (first available 2010) (Year: 2010).*
Adessi et al., "Converting a peptide into a drug: strategies to improve stability and bioavailability", Curr. Med. Chem., vol. 9, No. 9, pp. 963-978 (2002).
Baeriswyl et al., "Bicyclic peptides with optimized ring size inhibit human plasma kallikrein and its orthologues while sparing paralogous proteases", Chem. Med. Chem., vol. 7, No. 7, pp. 1173-1176 (2012).
Betts et al., "Amino acid properties and consequences of substitutions", *Bioinformatics for Geneticists*, Barnes et al., Eds., John Wiley & Sons, Ltd., ISBNs: 0-470-84393-4 (HB); 0-470-84392-2 (PB), pp. 289-316 (2003).

* cited by examiner

*Primary Examiner* — Thea D'Ambrosio
(74) *Attorney, Agent, or Firm* — Andrea L. C. Reid; Dechert LLP

(57) ABSTRACT

The invention describes peptide ligands specific for human plasma Kallikrein.

21 Claims, 35 Drawing Sheets

Specification includes a Sequence Listing.

HArg5    Arg5    Agb5    Agp5    β-HArg5

SDMA5    NDMA5        4GuanPhe5        Cit5

Alanine     2-Aminobutyric Acid     beta-Alanine

Ala     Aba     b-Ala

Amino isobutyric acid     Dipropyl Glycine     Penicillamine

Aib     Dpg     Pen

Azetidine carboxylic acid

Aze

Homoarginine

HArg

Nα-Me Arg

NMe-Arg

4-guanidyl phenylalanine

4GuanPhe

MODULATION OF STRUCTURED POLYPEPTIDE SPECIFICITY

CROSS-REFERENCE TO RELATED APPLICATIONS

This application is continuation of U.S. application Ser. No. 14/781,294, filed Sep. 29, 2015, now allowed, which is a national phase filing under 35 U.S.C. 371 of International Patent Application No. PCT/EP/2014/057440, filed Apr. 11, 2014, which claims priority to British application number GB 1306623.8, filed Apr. 11, 2013.

REFERENCE TO SEQUENCE LISTING

A Sequence Listing is being submitted electronically via EFS in the form of a text file, created Nov. 11, 2019, and named Bicycle_163626_SL.txt (69,404 bytes), the contents of which are incorporated herein by reference in their entirety.

TECHNICAL FIELD

The present invention relates to polypeptides which are covalently bound to molecular scaffolds such that two or more peptide loops are subtended between attachment points to the scaffold. In particular, the invention describes peptides which are specific for the human protease plasma Kallikrein and are modified in one or two peptide loops to enhance potency and/or protease resistance.

BACKGROUND

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers, et al., Nat Rev Drug Discov 2008, 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu, B., et al., Science 330 (6007), 1066-71), a cyclic peptide with the Arg-Gly-Asp motif binding to integrin αVb3 (355 $Å^2$) (Xiong, J. P., et al., Science 2002, 296 (5565), 151-5) or the cyclic peptide inhibitor upain-1 binding to urokinase-type plasminogen activator (603 $Å^2$; Zhao, G., et al., J Struct Biol 2007, 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney, R. J., et al., J Med Chem 1998, 41 (11), 1749-51). The favorable binding properties achieved through macrocyclization are even more pronounced in multicyclic peptides having more than one peptide ring as for example in vancomycin, nisin or actinomycin.

Different research teams have previously tethered polypeptides with cysteine residues to a synthetic molecular structure (Kemp, D. S. and McNamara, P. E., J. Org. Chem, 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 1 of this document shows a schematic representation of the synthesis of various loop peptide constructs. The constructs disclosed in this document rely on —SH functionalised peptides, typically comprising cysteine residues, and heteroaromatic groups on the scaffold, typically comprising benzylic halogen substituents such as bis- or tris-bromophenylbenzene. Such groups react to form a thioether linkage between the peptide and the scaffold.

We recently developed a phage display-based combinatorial approach to generate and screen large libraries of bicyclic peptides to targets of interest (Heinis, et al., Nat Chem Biol 2009, 5 (7), 502-7; see also international patent application WO2009/098450). Briefly, combinatorial libraries of linear peptides containing three cysteine residues and two regions of six random amino acids (Cys-(Xaa)$_6$-Cys-(Xaa)$_6$-Cys) (SEQ ID NO: 210) were displayed on phage and cyclised by covalently linking the cysteine side chains to a small molecule (tris-(bromomethyl)benzene). Bicyclic peptides isolated in affinity selections to the human proteases cathepsin G and plasma Kallikrein (PK) had nanomolar inhibitory constants. The best inhibitor, PK15, inhibits human PK (hPK) with a $K_i$ of 3 nM. Similarities in the amino acid sequences of several isolated bicyclic peptides suggested that both peptide loops contribute to the binding. PK15 did not inhibit rat PK (81% sequence identity) nor the homologous human serine proteases factor XIa (hfXIa; 69% sequence identity) or thrombin (36% sequence identity) at the highest concentration tested (10 μM) (Heinis, et al., Nat Chem Biol 2009, 5 (7), 502-7). This finding suggested that the bicyclic inhibitor is highly specific and that other human trypsin-like serine proteases will not be inhibited. A synthetic, small peptidic inhibitor such as PK15 having the above described potency and target selectivity has potential application as a therapeutic to control PK activity in hereditary angioedema, a life-threatening disease which is characterized by recurrent episodes of edema or to prevent contact activation in cardiopulmonary bypass surgery.

The peptide PK15 was isolated from a library based on the peptide PK2, H-ACSDRFRNCPLWSGTCG-NH$_2$ (SEQ ID NO: 1), in which the second 6-amino acid loop was randomised. The sequence of PK15 was H-ACSDRFRNCPADEALCG-NH$_2$ (SEQ ID NO: 2), and the IC50 binding constant for human Kallikrein was 1.7 nM.

SUMMARY OF THE INVENTION

We have analysed kallikrein-binding reagents in order to optimise binding affinity and activity. In our copending unpublished patent application PCT/EP2012/069898, selective bicyclic peptide ligands which are Inhibitors of human plasma kallikrein have been described.

In one embodiment described therein, the loops of the peptide ligand comprise five amino acids and a first loop comprises the motif $G_r x^W/_F P x^K/_R G_r$ (SEQ ID NO: 211), wherein $G_r$ is a reactive group. In the present context, the reference to a "first" loop does not necessarily denote a particular position of the loop in a sequence. In some embodiments, however, the first loop may be proximal loop in an amino terminus to carboxy terminus peptide sequence. For example, the polypeptide further comprises a second, distal loop which comprises the motif $G_r^T/_L H^Q/_T x L G_r$ (SEQ ID NO: 212). Examples of sequences of the first loop include $G_r x W P A R G_r$ (SEQ ID NO: 3), $G_r x W P S R G_r$ (SEQ ID NO: 4), $G_r x F P F R G_r$ (SEQ ID NO: 5) and $G_r x F P Y R G_r$ (SEQ ID NO: 2). In these examples, x may be any amino acid, but is for example S or R.

For example, the polypeptide may be one of the polypeptides set forth in Table 4, Table 5 or Table 6.

The reactive group can be a reactive amino acid. For example, the reactive amino acid is cysteine.

Variants of the polypeptides can be prepared by identifying those residues which are available for mutation and preparing libraries which include mutations at those positions. For example, the polypeptide 06-56 in Table 4, FIGS. 5, 6 can be mutated without loss of activity at positions Q4 and T10 (see Examples below). Polypeptide ligands comprising mutations at these positions can be selected which have improved binding activity in comparison with 06-56.

For a kallikrein-inhibiting bicycle, it is pertinent to obtain an adequate protease stability profile, such that it has a low protease-driven clearance in plasma or other relevant environments. In a rapid comparative plasma stability assay (Method #1) that observed the progressive disappearance of parent peptide in rat plasma, it was found that the N-terminal alanine (which is present at the time of selections and was originally included in synthetic peptides of lead sequences) is rapidly removed across all bicycle sequences tested by both rat and human plasma. This degradation was avoided by synthesising a lead candidate lacking both N- and C-terminal alanines. To remove potential recognition points for amino- and carboxypeptidases, the free amino-terminus that now resides on Cys 1 of the lead candidate is capped with acetic anhydride during peptide synthesis, leading to a molecule that is N-terminally acetylated. In an equal measure, the C-terminal cysteine is synthesised as the amide so as to remove a potential recognition point for carboxypeptidases.

Thus, in one example Bicyclic lead candidates have the following generic sequence:

Ac-C$_1$AA$_1$AA$_2$AA$_n$C$_2$AA$_{n+1}$AA$_{n+2}$AA$_{n+3}$C$_3$(TMB)-NH$_2$ where "Ac" refers to N-terminal acetylation, "—NH$_2$" refers to C-terminal amidation, where "C$_1$, C$_2$, C$_3$" refers to the first, second and third cysteine in the sequence, where "AA$_1$" to "AA$_n$" refers to the position of the amino acid (whose nature "AA" is defined by the selections described above), and where "(TMB)" indicates that the peptide sequence has been cyclised with TBMB (trisbromomethylbenzene) or any other suitable reactive scaffold.

In this context, the lead peptides "Ac-(06-34-18)(TMB)" and "Ac-(06-34-18)(TMB) Phe2 Tyr4" have the sequences Ac-CSWPARCLHQDLC-NH$_2$ (SEQ ID NO: 7) and Ac-CSFPYRCLHQDLC-NH$_2$ (SEQ ID NO: 8), respectively. These can be numbered according to the above scheme as

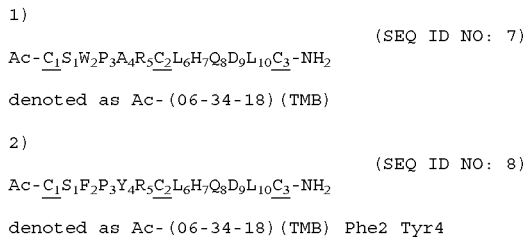

1)
(SEQ ID NO: 7)
Ac-<u>C</u>$_1$S$_1$W$_2$P$_3$A$_4$R$_5$<u>C</u>$_2$L$_6$H$_7$Q$_8$D$_9$L$_{10}$<u>C</u>$_3$-NH$_2$ denoted as Ac-(06-34-18)(TMB)

2)
(SEQ ID NO: 8)
Ac-<u>C</u>$_1$S$_1$F$_2$P$_3$Y$_4$R$_5$<u>C</u>$_2$L$_6$H$_7$Q$_8$D$_9$L$_{10}$<u>C</u>$_3$-NH$_2$ denoted as Ac-(06-34-18)(TMB) Phe2 Tyr4 where the invariant cysteines are underlined. These peptides have been characterised in detail, and shown to have sub-nanomolar potency against kallikrein, with very favourable selectivity profiles towards kallikrein-homologous proteins, while retaining good cross-reactivity towards rat kallikrein. The latter is valuable for establishing pharmacodynamics in animal models.

The unmodified peptide Ac-06-34-18(TMB)-NH$_2$ has a half-life of 2.3 hrs in rat plasma, while that of Ac-06-34-18 (TMB)-NH$_2$ Phe2 Tyr4 is slightly shorter, at 0.9 hrs (Table 1). In an effort to identify the proteolytic recognition site(s) in Ac-06-34-18(TMB)-NH$_2$, the peptide was sampled in rat plasma over time (method #1), and each sample was analysed for the progressive appearance of peptide fragments using MALDI-TOF mass spectrometry. This revealed Arg5 in Loop 1 to be the main site of protease recognition and subsequent peptide degradation.

A process of chemical synthesis was undertaken to identify Arginine5 substitutes that would sufficiently protect the peptide from rat plasma protease degradation. It was found that removal of Arg 5 in loop 1, or replacement of the Arg side chain with any non-charged or charged chemical entities, enhances the stability of the peptide ligand.

Moreover, the proteolytic stability is enhanced by chemical modification of the peptide bonds N- or C-terminally adjacent to Arg5. The chemical modification is, for example, α-N-alkylation, or modification of the peptide bond with its reduced amide form.

In one embodiment, proteolytic stability is enhanced by steric obstruction of nearby amino acids to Arg5. For example, the steric obstruction results from α-N-alkylation.

These Bicyclic Peptide candidates were then evaluated for the following characteristics:

1) maintenance of potency against human kallikrein (seeking a Ki of 10 nM or lower)
2) maintenance of potency against rat kallikrein (seeking a Ki of 50 nM or lower)
3) enhanced stability in rat plasma (greater $t_{1/2}$ desirable compared to the wildtype peptide)
4) maintenance of selectivity profile against other kallikrein-related enzymes and proteins.

In the course of the investigations in PCT/EP2012/069898, it was determined that the following Arginine modifications or mimics fulfilled the 4 above criteria, these being a) 4-guanidylphenylalanine (4-GuanPhe: $t_{1/2}$ increase in rat plasma: 1-5 fold);
b) homoarginine (HArg: $t_{1/2}$ increase in rat plasma: ~2-5-fold); and
c) α-N-methylarginine (NMe-Arg: $t_{1/2}$ increase in rat plasma: >10-fold)

We have found that certain non-natural amino acids permit binding to plasma Kallikrein with nM Ki, whilst increasing residence time in plasma significantly. The data are summarized in Table 1 and FIG. 17.

Moreover, PCT/EP2012/069898 also disclosed an additional modification at position 3 in 06-34-18, where the proline was replaced with azetidine carboxylic acid (Aze3). This modification, likely due to its greater constraint and reduced entropy, invariably enhances the potency of an 06-34-18-based peptide by a factor of 2 to 5 (Table 1). In combination with the stability enhancing modifications at Arg 5 (specifically, HArg, NMe-Arg and 4GuanPhe), more potent Bicyclic Peptide derivatives are obtained.

Exemplary non-natural amino acids are selected from N-methyl Arginine, homo-arginine and hydroxyproline. N-methyl and homo-derivatives of Arginine are used to replace Arginine, and proline 3 can be replaced by, for example, hydroxyproline, azetidine carboxylic acid, or an alpha-substituted amino acid, such as aminoisobutyric acid. In another embodiment, arginine may be replaced with guanidyl-phenylalanine.

In one embodiment, the polypeptide comprises a first loop which comprises the motif $G_rxWPARG_r$ (SEQ ID NO: 3), wherein P is replaced with azetidine carboxylic acid; and/or R is replaced with N-methyl arginine; and/or R is replaced with homoarginine; and/or R is replaced with guanidyl-phenylalanine.

In one embodiment, the polypeptide comprises a first loop which comprises the motif $G_rxFPYRG_r$ (SEQ ID NO: 6), wherein R is replaced with N-methyl arginine; and/or R is replaced with homoarginine, and wherein proline is replaced by azetidine carboxylic acid; and/or R is replaced with guanidyl-phenylalanine.

We have now developed the approaches used in PCT/EP2102/069898, and set forth herein, as applied to the optimization of the second loop. In accordance with the present invention, we have identified an additional protease recognition site in loop 2, which is located at Histidine 7 in the 06-34-18 sequence. This residue is in particular recognised by proteases contained in ex vivo human plasma. Moreover, this site is also recognised by rat membrane-bound proteases as determined in an in vivo rat pharmacokinetic study. Thus, for 06-34-18 to attain a suitable pharmacokinetic stability profile as required for therapeutic purposes, both protease recognition sites (Arg5 in Loop1 and His7 in Loop2) have to be stabilised such that the peptide is resistant to human plasma proteases, and the proteolytically aggressive environment encountered both in vivo in rat and human.

Accordingly, in a first aspect, the present invention provides a peptide ligand specific for human Kallikrein comprising a polypeptide comprising at least three reactive groups, separated by at least two loop sequences, and a molecular scaffold which forms covalent bonds with the reactive groups of the polypeptide such that at least two polypeptide loops are formed on the molecular scaffold, wherein the loops of the peptide ligand comprises five amino acids and one loop comprises the motif $G_r{}^T/_LH^Q/_TxLG_r$ (SEQ ID NO: 212).

In the context of peptide 06-34-18, this loop is the second loop, positioned C-terminal to a first loop.

For example, the motif is $G_rxHxDLG_r$ (SEQ ID NO: 213), wherein $G_r$ is a reactive group. For example, the motif $G_rTHxxLG_r$ (SEQ ID NO: 214).

In one embodiment, two adjacent loops of the polypeptide comprise the motif $G_rx^w/_FPx^K/_RG_r{}^T/_LH^Q/_TDLG_r$ (SEQ ID NO: 9).

Examples of such polypeptides are set forth in Table 4, Table 5 or Table 6.

In a second aspect, the invention relates to a peptide ligand as described in the first aspect of the invention, wherein removal of His 7 in loop 2, or replacement of the histidine side chain with any non-charged or charged chemical entities, enhances the stability of the peptide ligand.

For example, proteolytic stability is enhanced by chemical modification of the peptide bonds N- or C-terminally adjacent to His7. The chemical modification is, for example, α-N-alkylation, or modification of the peptide bond with its reduced amide form.

In one embodiment, proteolytic stability is enhanced by steric obstruction of nearby amino acids to His 7. For example, the steric obstruction results from replacement of position 9 with its D-amino acid enantiomer, or α-N-alkylation.

In another embodiment, proteolytic stability is enhanced by introduction of sterically obstructive amino acids at position 6. For example, proteolytic stability is enhanced by introduction of Cβ-derivatised amino acids such as phenylglycine or cyclohexylglycine at position 6, which enhance the potency of the peptide ligand sequence towards human plasma kallikrein and reduce the proteolytic hydrolysis of the C-terminal peptide bond.

The teaching of the present invention may be combined with the teaching of PCT/EP2012/06989, such that the polypeptide according to the invention can comprise a first loop which comprises the motif $G_rxWPARG_r$ (SEQ ID NO: 3) or $G_rxFPYRG_r$ (SEQ ID NO: 9) and a second loop comprising the motif $G_r{}^T/_LH^Q/_TxLG_r$ (SEQ ID NO: 212).

In one example, in the first loop Pro 3 is replaced with azetidine carboxylic acid; and/or Arg 5 is replaced with N-methyl arginine; and/or Arg 5 is replaced with homoarginine; and/or Arg 5 is replaced with guanidylphenylalanine.

PK122 (SEQ ID NO: 203); PK123 (SEQ ID NO: 202); PK124 (SEQ ID NO: 204); PK125 (SEQ ID NO: 179); PK126 (SEQ ID NO: 180); PK127 (SEQ ID NO: 181); PK128 (SEQ ID NO: 182); PK129 (SEQ ID NO: 183); PK130 (SEQ ID NO: 184); PK131 (SEQ ID NO: 185); PK132 (SEQ ID NO: 186); PK133 (SEQ ID NO: 187); PK134 (SEQ ID NO: 188); PK135 (SEQ 9 ID NO: 189); PK136 (SEQ ID NO: 190); PK137 (SEQ ID NO: 191); PK138 (SEQ ID NO: 192); PK139 (SEQ ID NO: 193); PK140 (SEQ ID NO: 194); PK141 (SEQ ID NO: 195); PK142 (SEQ ID NO: 196); PK143 (SEQ ID NO: 197)

Figure 2:
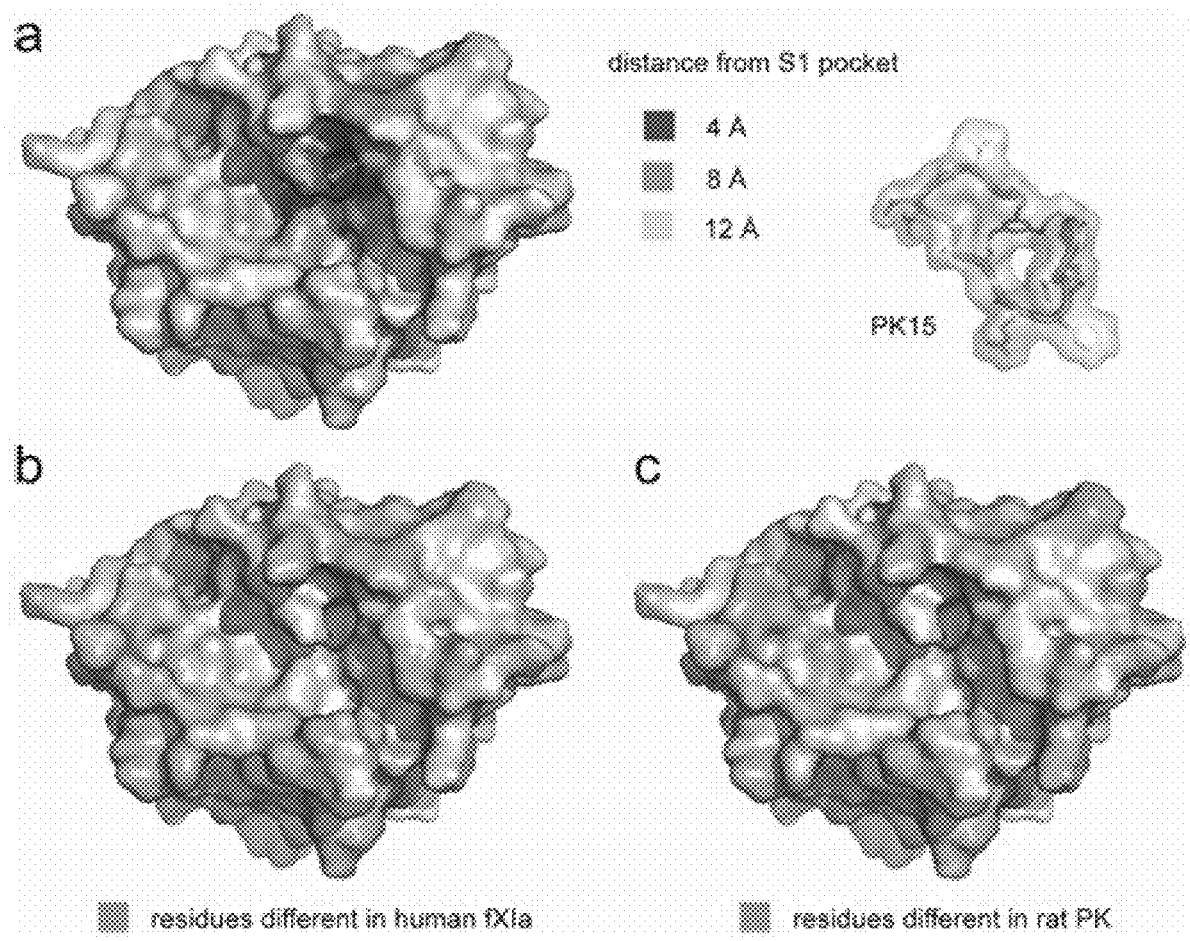

FIG. 2 Comparison of the surface amino acids of hPK and homologous serine proteases. (a) Structure of hPK (PDB entry 2ANW) with surface representation. Atoms of amino acids being exposed to the surface and closer than 4, 8 and 12 Å to benzamidine (in grey) bound to the S1 pocket are stained more darkly. (b) Structure of hPK. The side chains of amino acids that are different in hfXIa are highlighted. (c) Structure of hPK. The side chains of amino acids that are different in rPK are highlighted.

Figure 3:
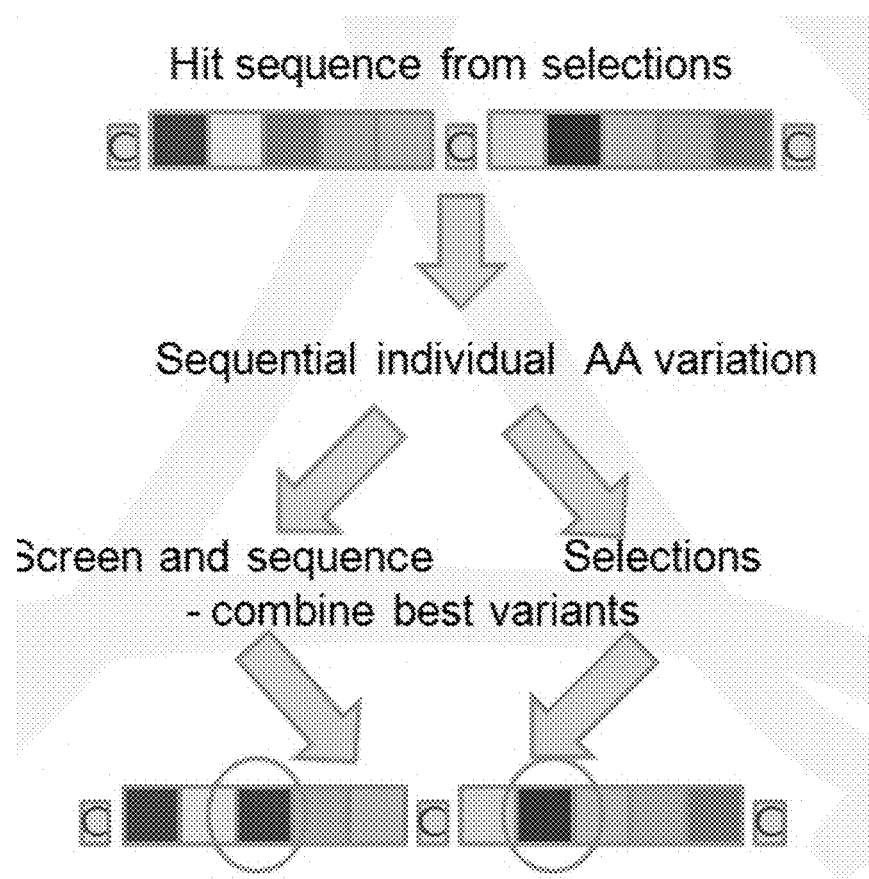
Figure 4:
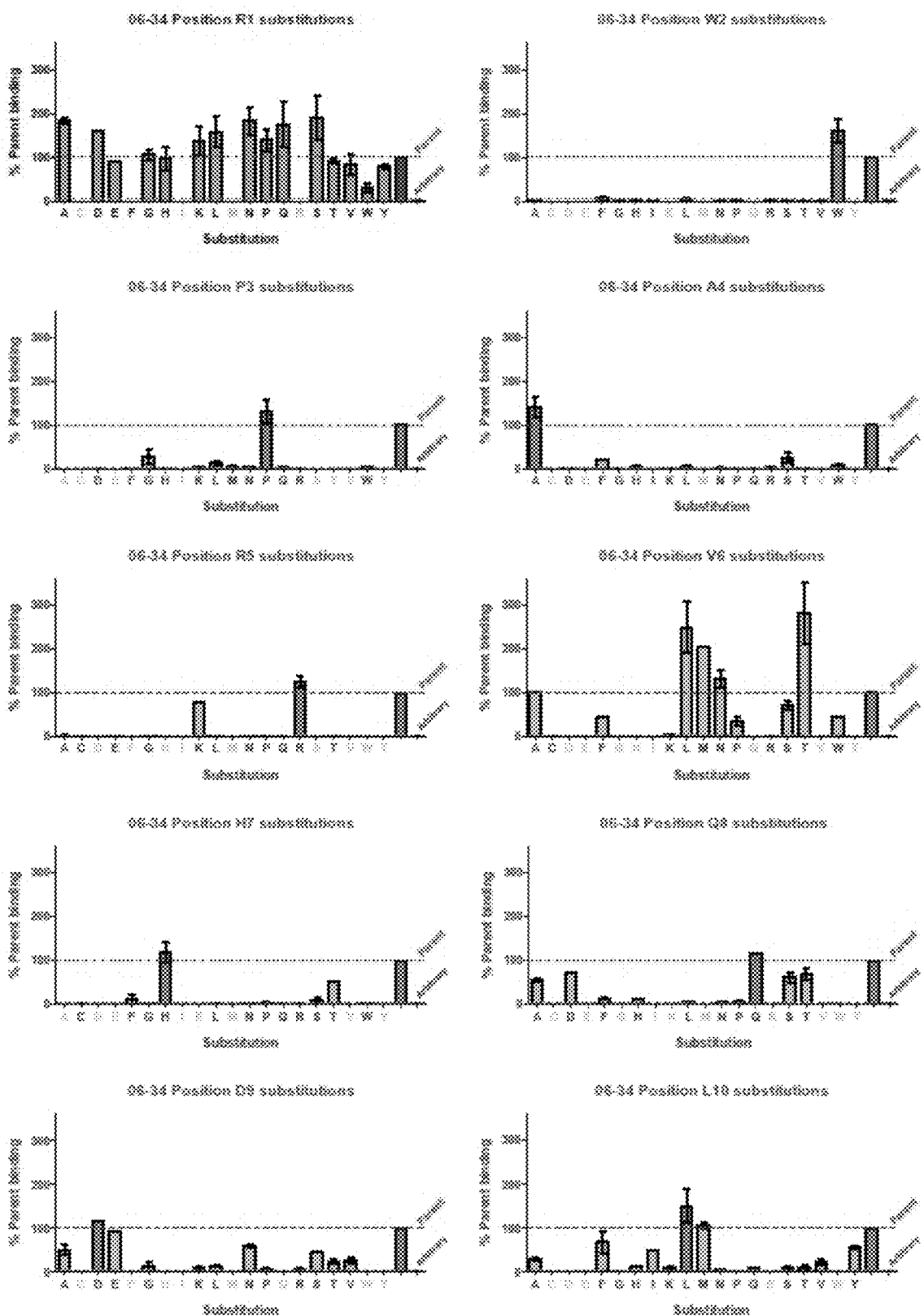

FIG. 3 Pictorial representation of the method used for determination of preferred residues for mutation in polypeptide ligands FIG. 4 Analysis of amino acid substitutions in peptide 06-34 (Table 4) on the binding of the peptide to plasma Kallikrein at 2 nM. For each position, the effect of various mutations at that position is shown, in comparison to the parent sequence.

Figure 5:
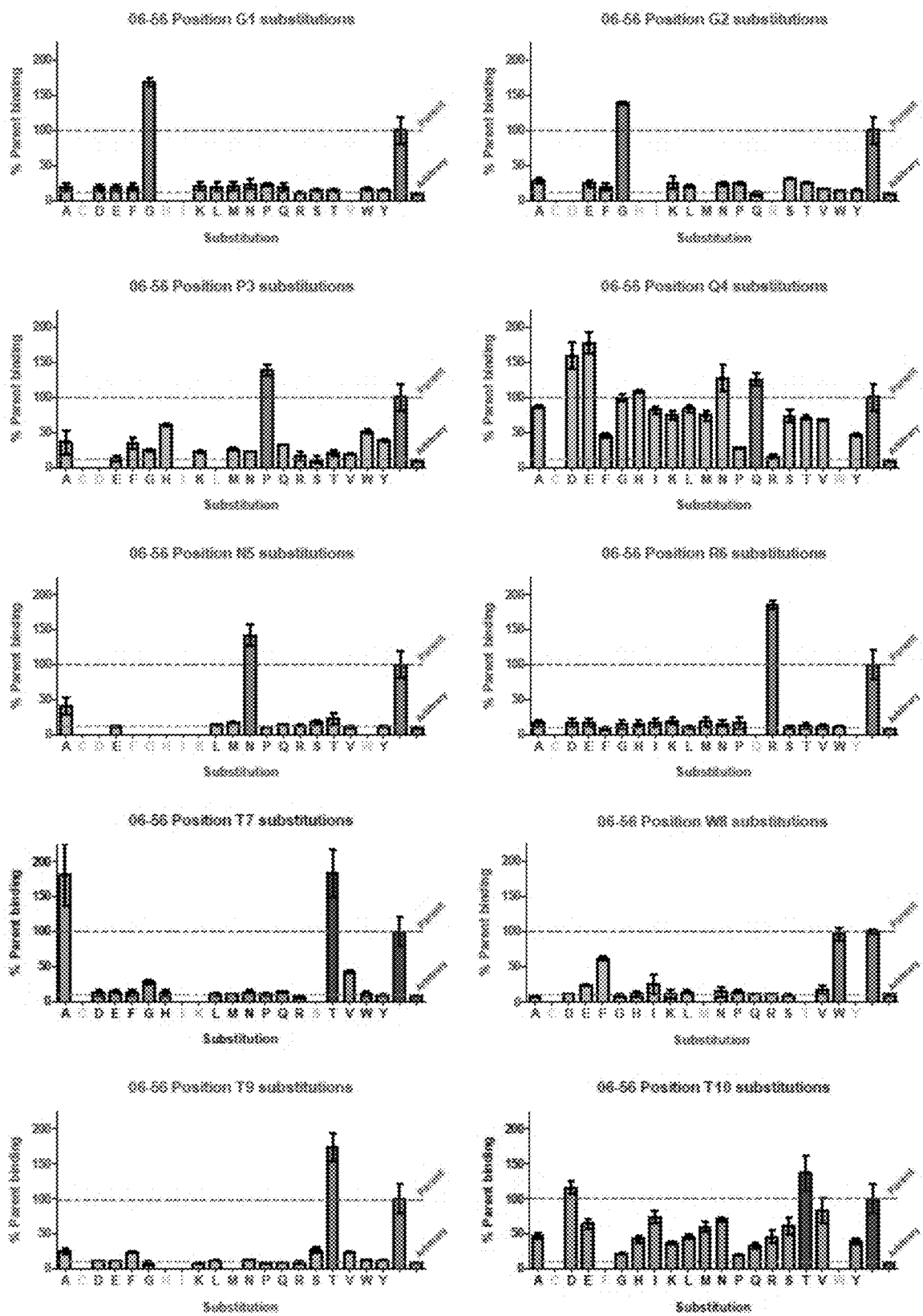

FIG. 5 Analysis of amino acid substitutions in peptide 06-56 (Table 4) on the binding of the peptide to plasma Kallikrein at 2 nM. For each position, the effect of various mutations at that position is shown, in comparison to the parent sequence.

Figure 6:
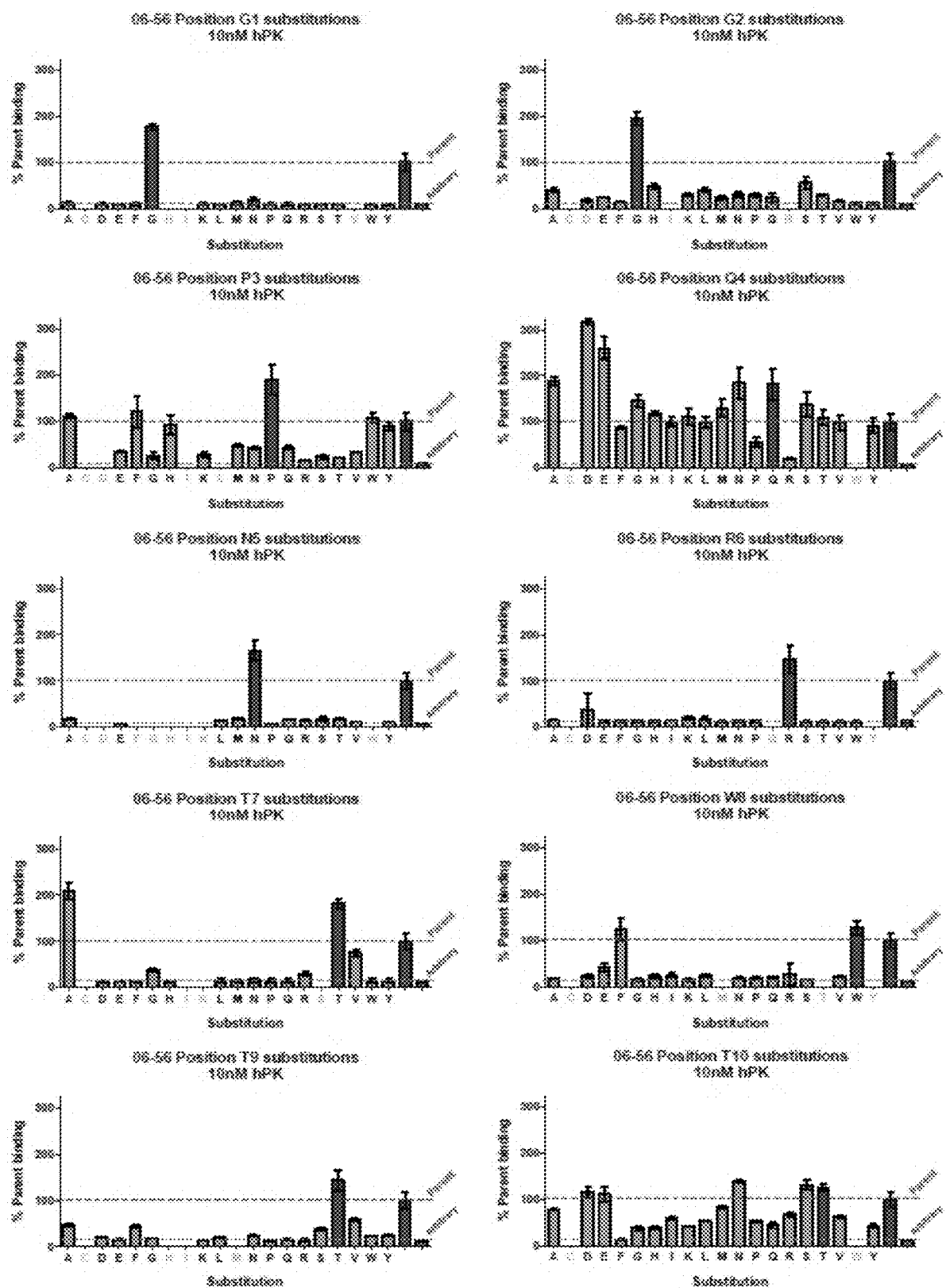

FIG. 6 Analysis of amino acid substitutions in peptide 06-56 (Table 4) on the binding of the peptide to plasma Kallikrein at 10 nM. For each position, the effect of various mutations at that position is shown, in comparison to the parent sequence.

Figure 7:
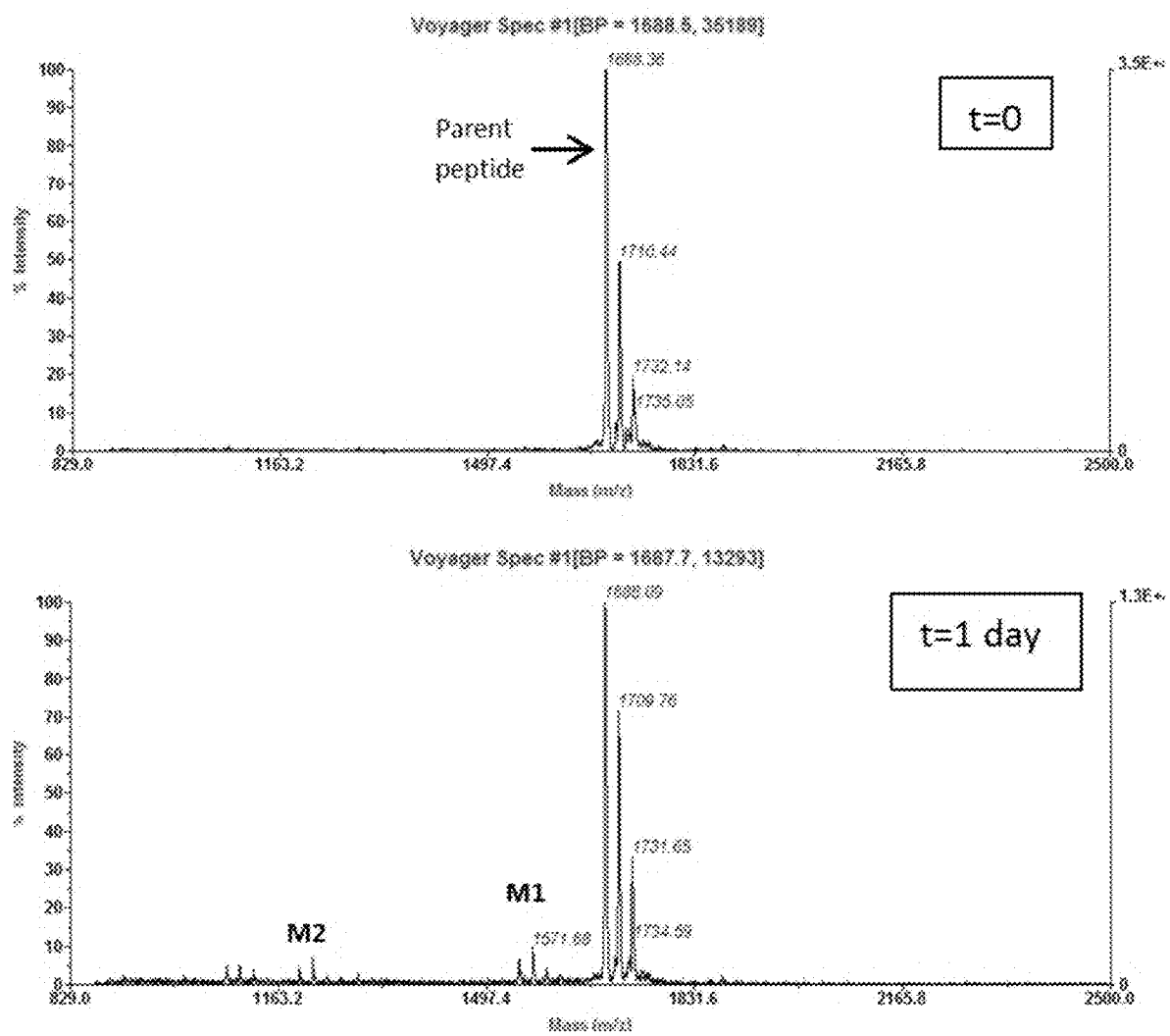
Figure 7:
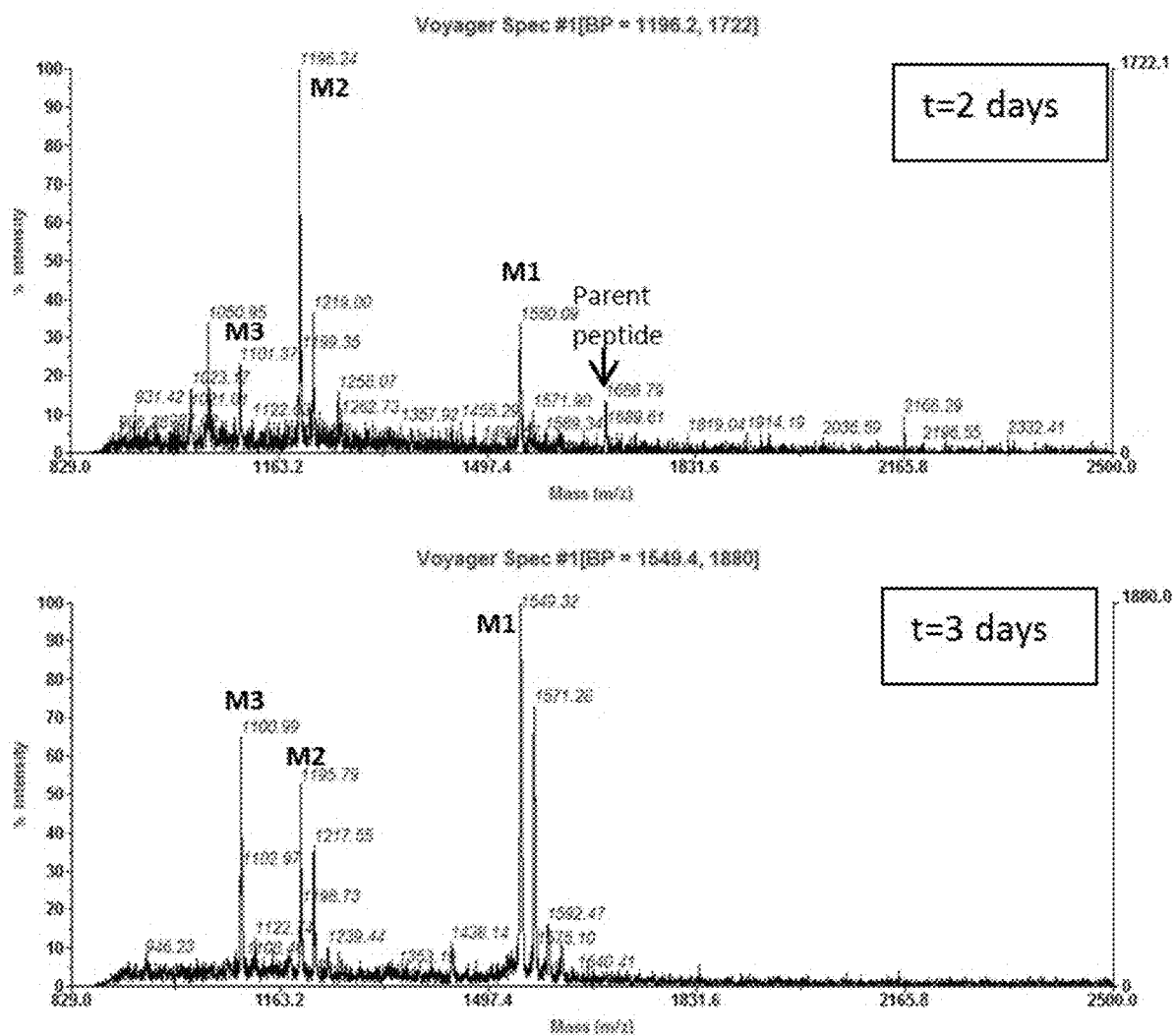

FIG. 7 Mass spectrometric output showing the mass spectra of Ac-06-34-18(TMB)-NH2 after exposure to 35% rat plasma, at to, 1 day, 2 days and 3 days (method #1). Mass accuracies vary somewhat due to interfering ions and low concentrations of fragments; however identification of discrete proteolytic fragments is possible.

Figure 8:
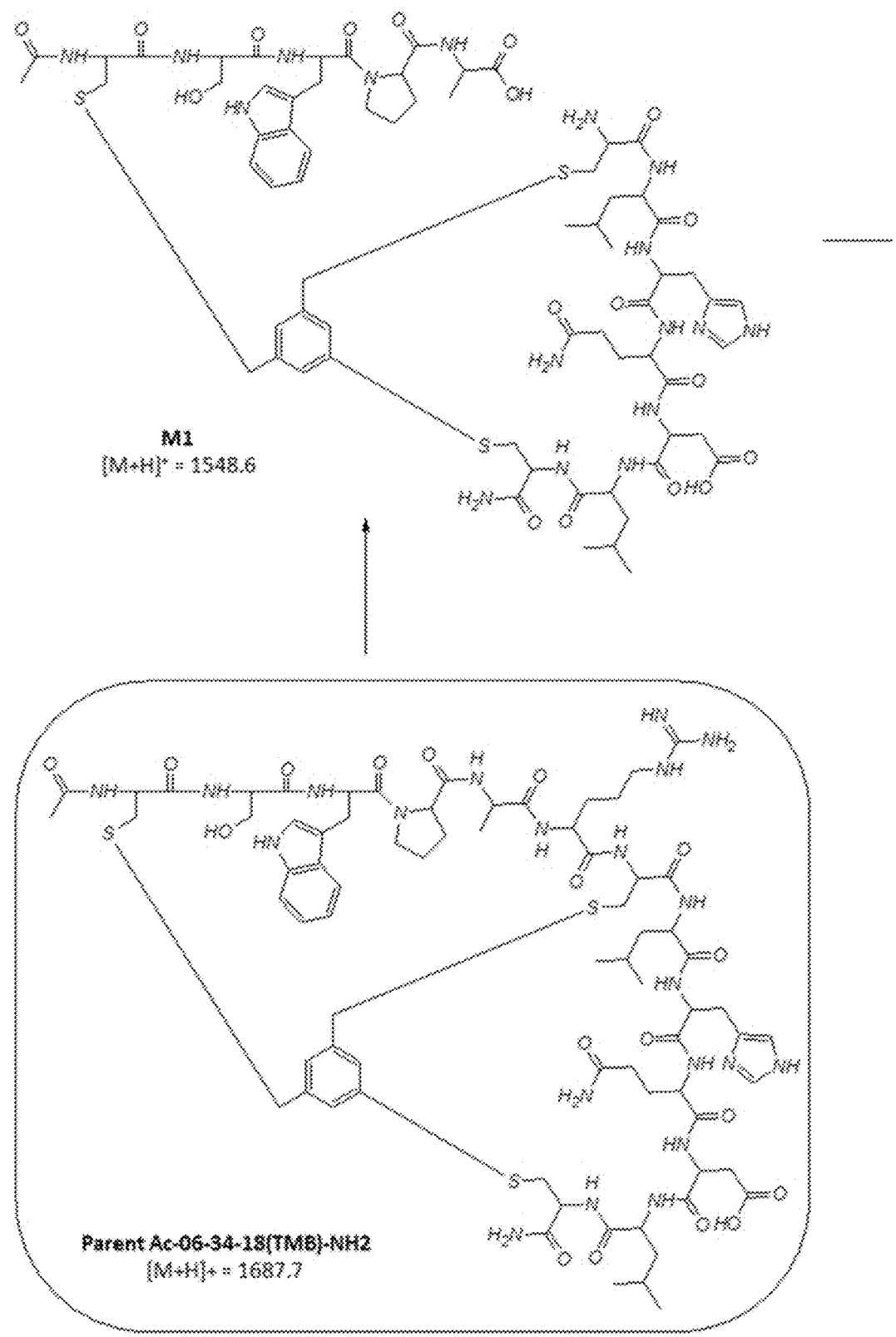
Figure 8:
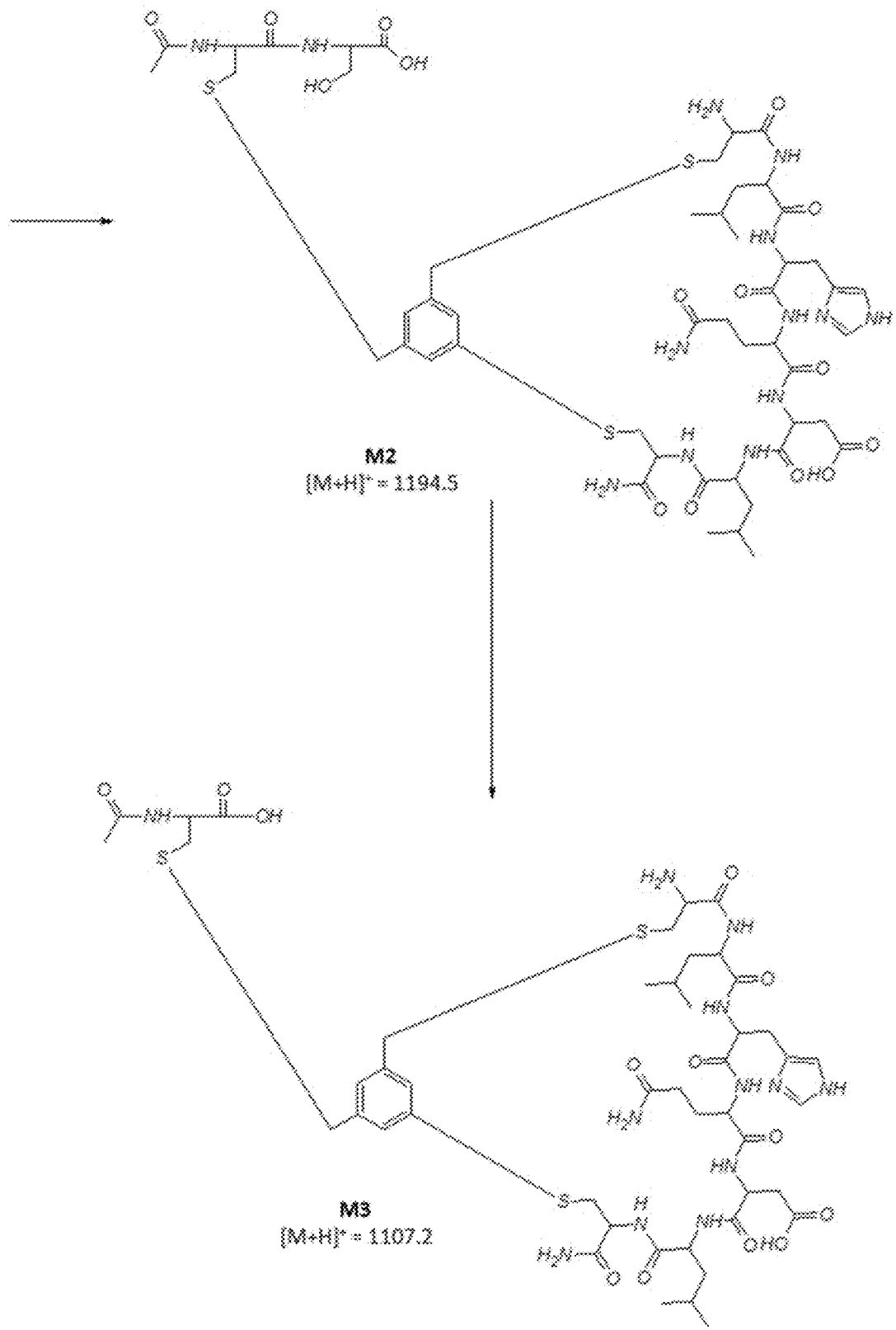

FIG. 8 Chemical structures of metabolites M1, M2, M3 of Ac-06-34-18(TMB)-NH2 identified after exposure to rat plasma.

Figure 9:
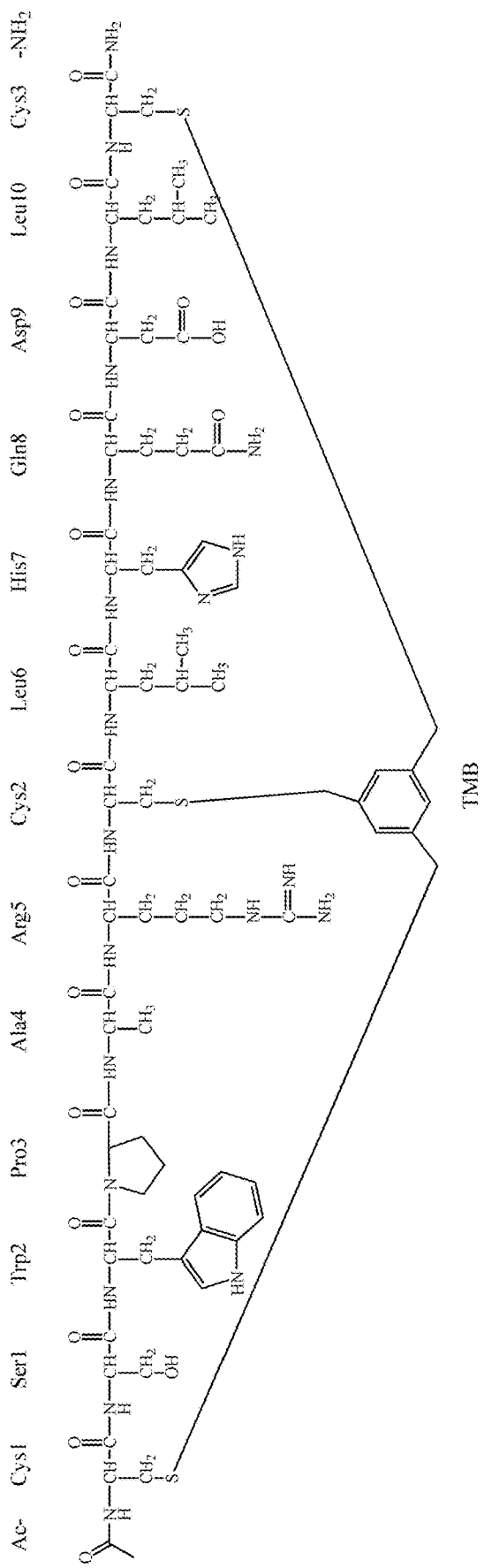

FIG. 9 Chemical structure of the Ac-06-34-18(TMB)-NH2 lead (SEQ ID NO: 7)

Figure 10:
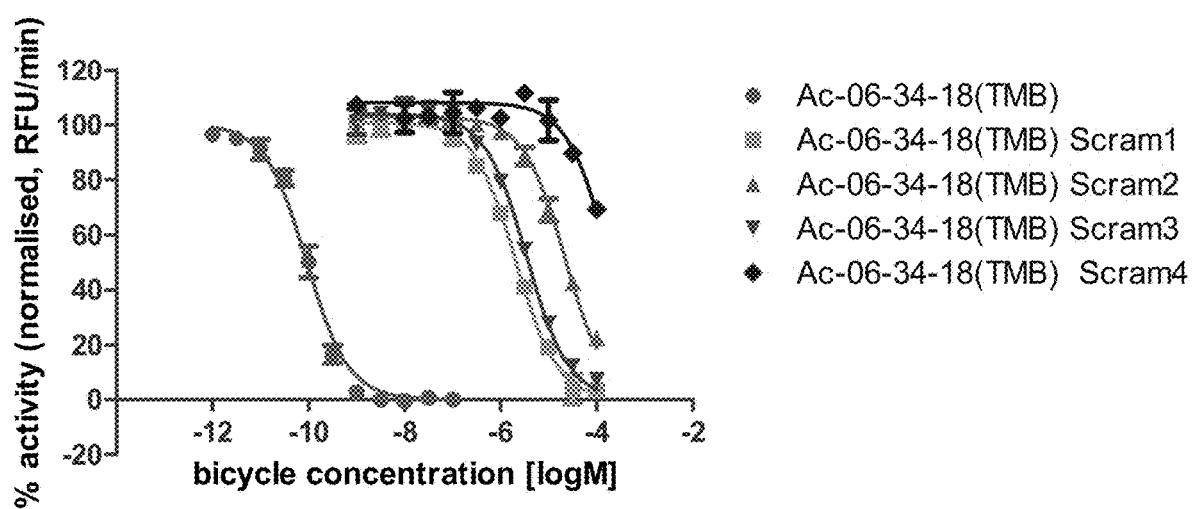

FIG. 10 Enzyme inhibition assay of Kallikrein by the Ac-06-34-18(TMB)-NH2 lead and its 1$^{st}$ loop scrambled derivatives. A dramatic reduction in affinity is observed, underlining the importance of the integrity of the WPAR pharmacophore.

Figure 11:
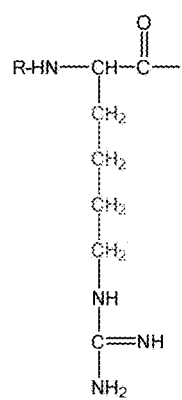
Figure 11:
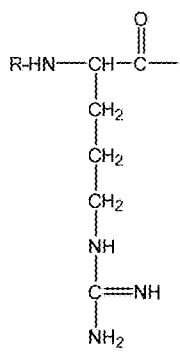
Figure 11:
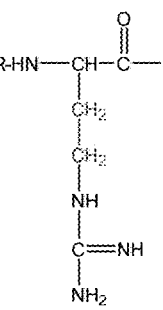
Figure 11:
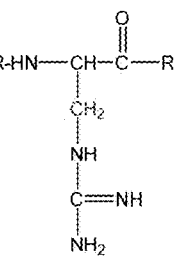
Figure 11:
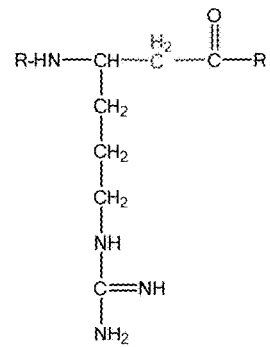
Figure 11:
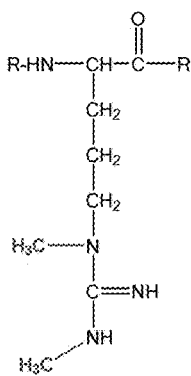
Figure 11:
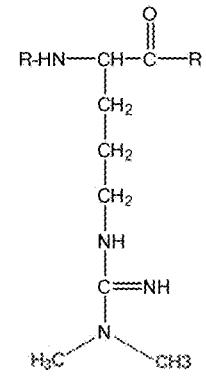
Figure 11:
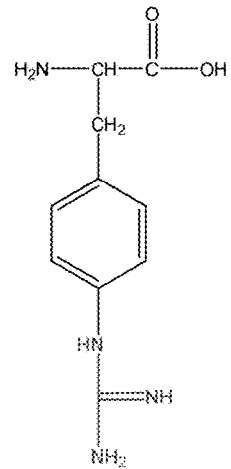

FIG. 11 Chemical structures of arginine and its analogues.

Figure 12:
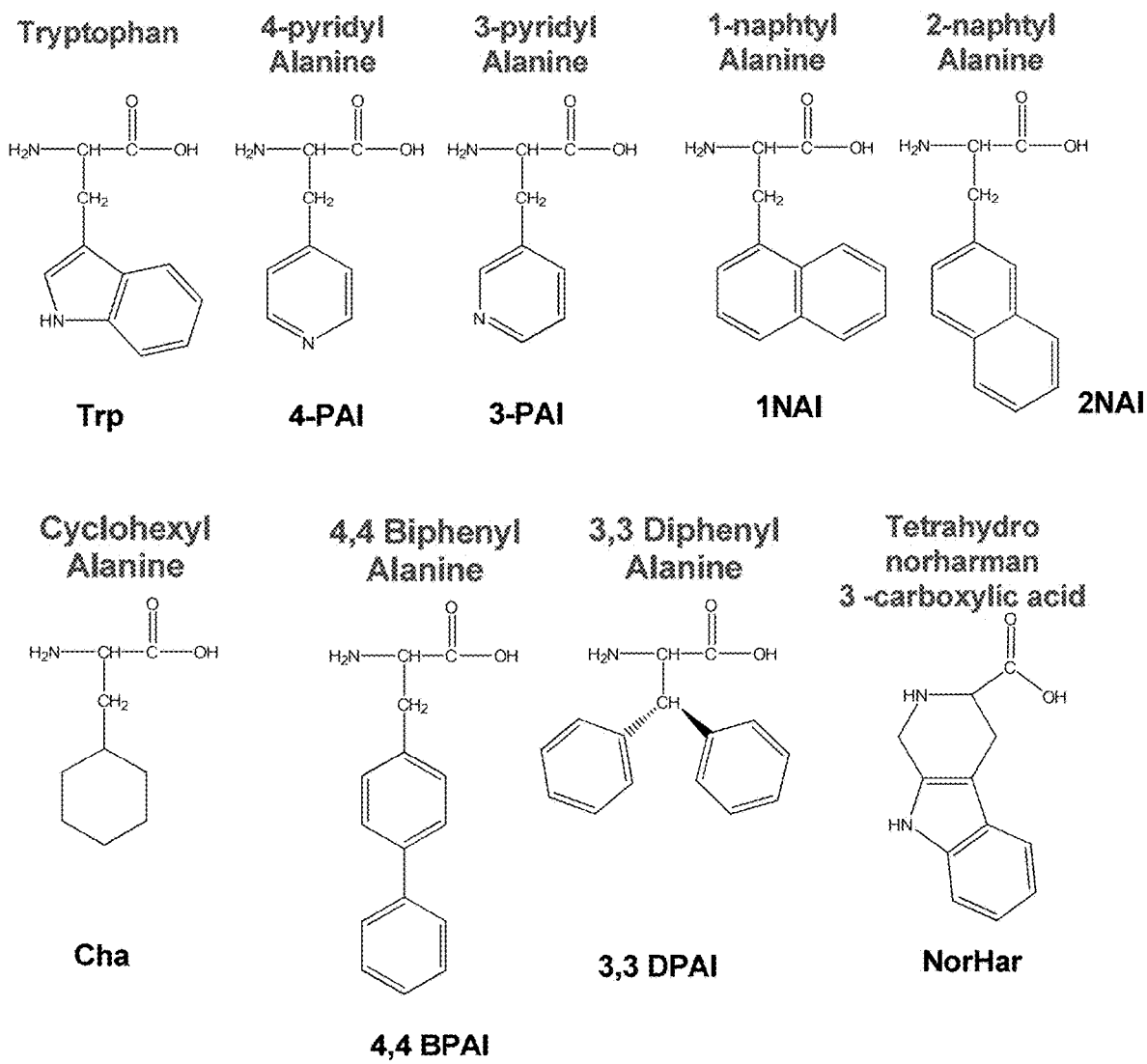

FIG. 12 Chemical structures of Trp and potential hydrophobic analogues

Figure 13:
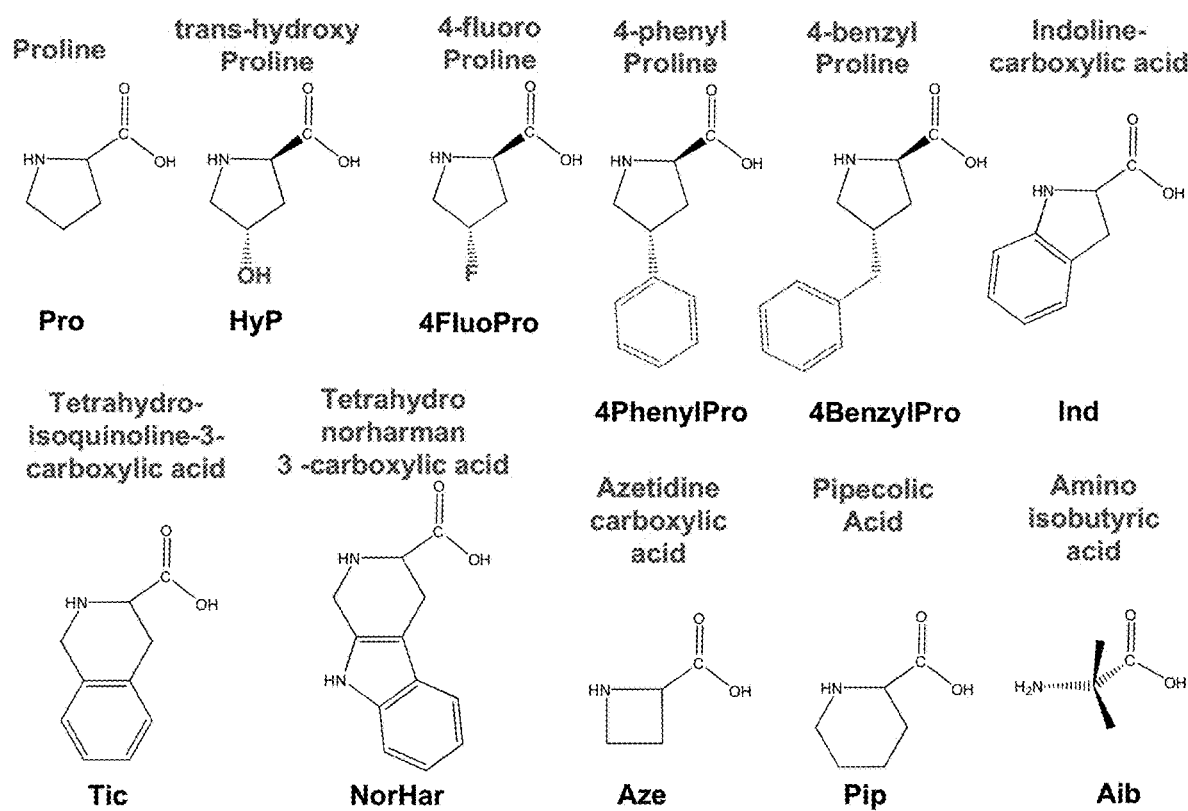

FIG. 13 Chemical structures of Pro and potential constrained analogues

Figure 14:
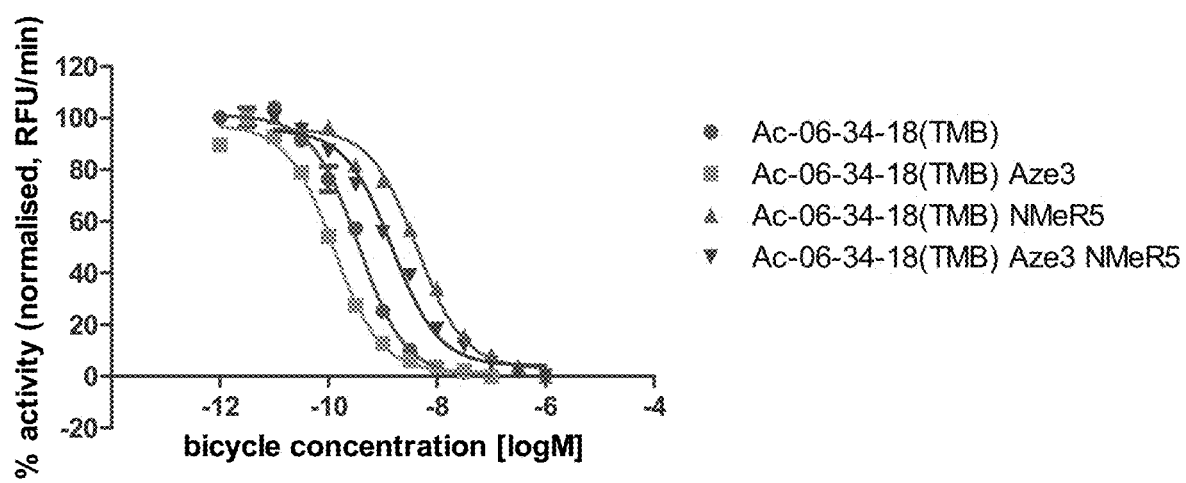

FIG. 14 Comparative Kallikrein inhibition by Aze3, NMeArg5 and doubly modified Ac-06-34-18(TMB)-NH2.

Figure 15:
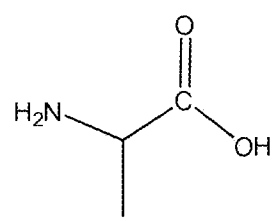
Figure 15:
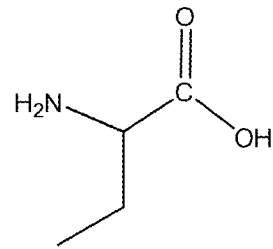
Figure 15:
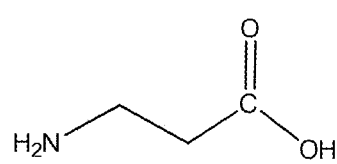
Figure 15:
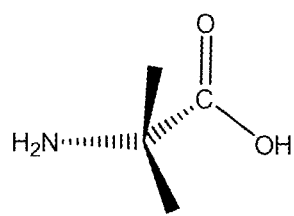
Figure 15:
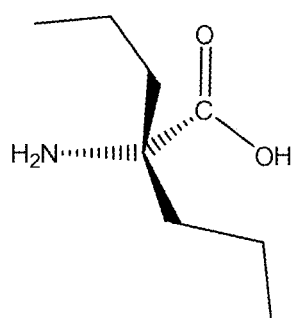
Figure 15:
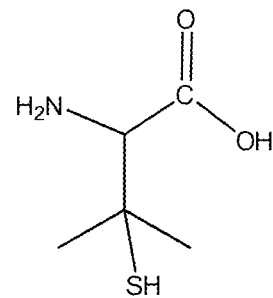

FIG. 15 Chemical structures of Alanine and derivatives thereof

Figure 16:
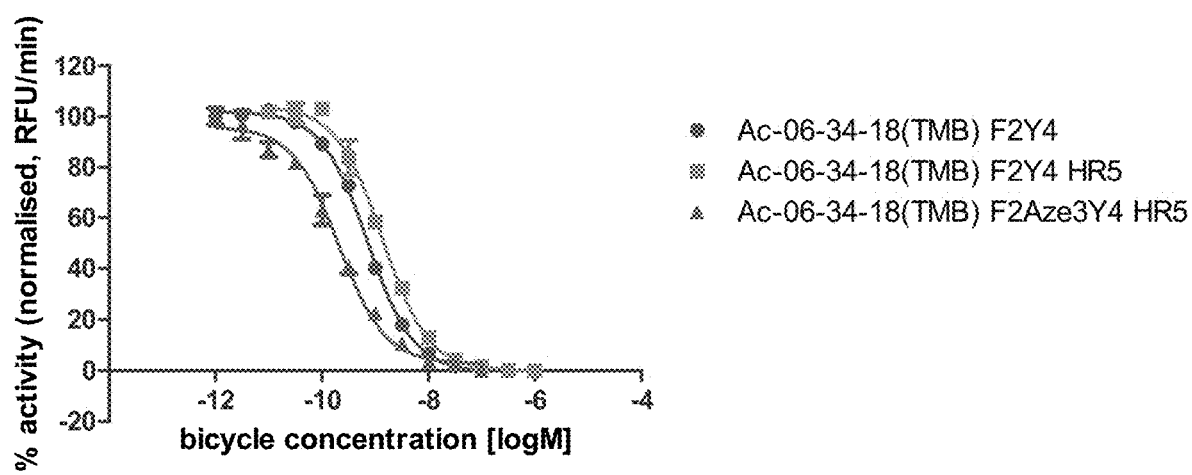

FIG. 16 Comparative Kallikrein inhibition by F2Y4, F2Y4 HR5 and doubly modified Ac-06-34-18(TMB)-NH2.

Figure 17:
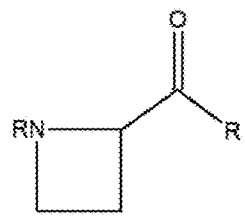
Figure 17:
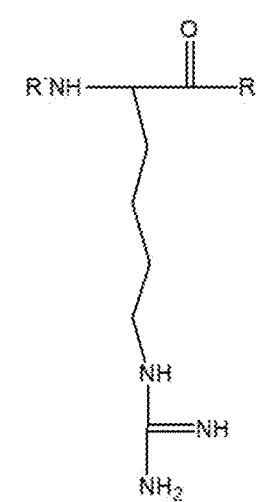
Figure 17:
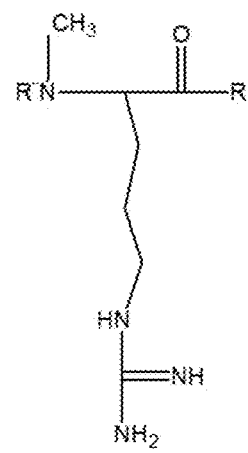
Figure 17:
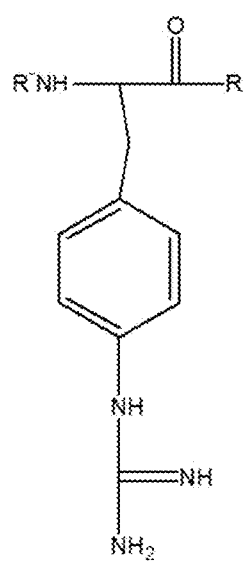

FIG. 17 Chemical structures of Loop1 modifications in Ac-(06-34-18) that impart favorable rat plasma stability and/or potency enhancement (Aze3 in place of Pro3, 4GuanPhe in place of Arg5, HArg in place of Arg5, NMe-Arg5 in place of Arg5).

Figure 18A:
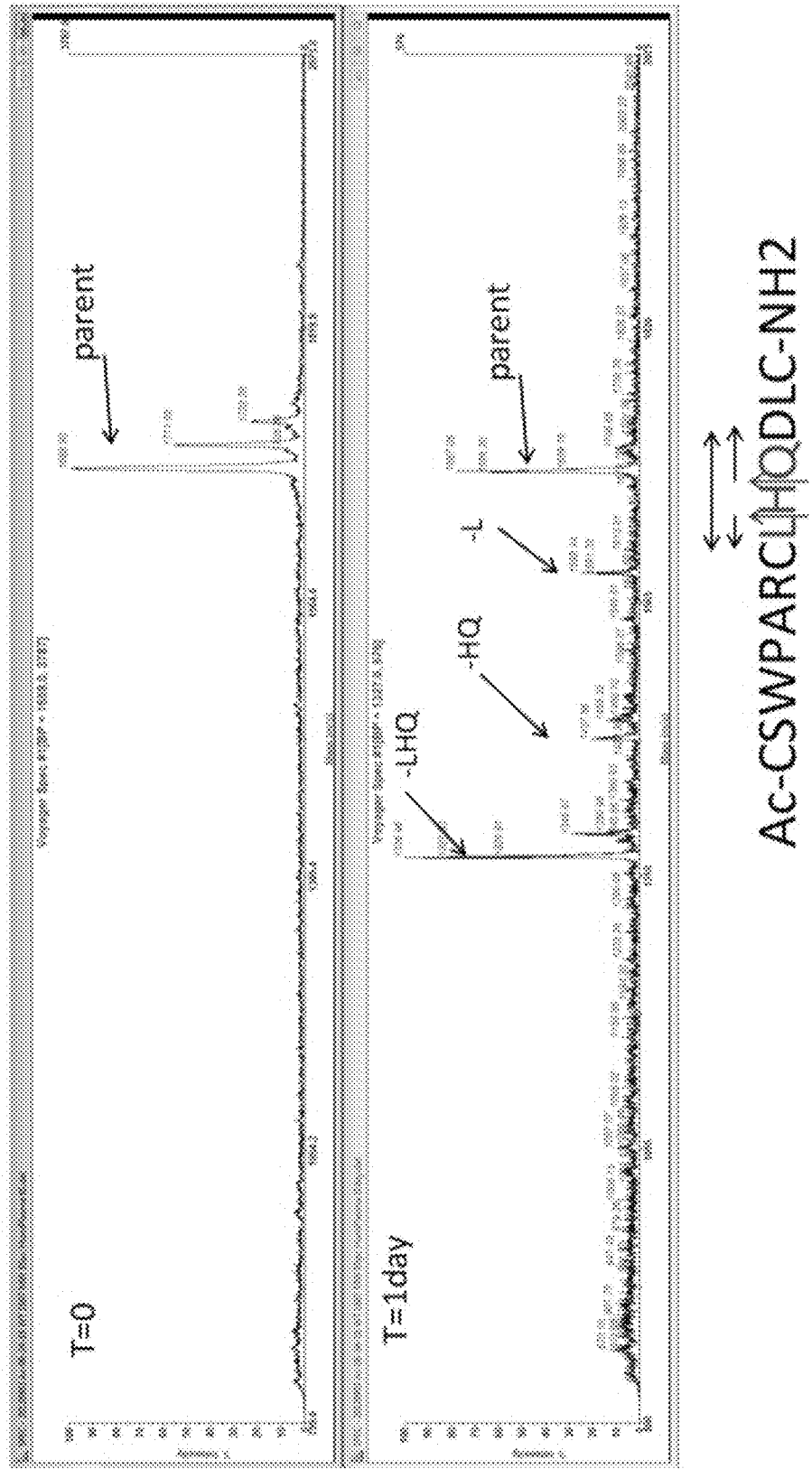

FIG. 18a Wildtype peptide (SEQ ID NO: 7) is subjected to human plasma. Note the appearance of fragments with His7-Gln8, Leu6, and Leu6-His7-Gln8 removed. Due to the nature of MALDI-TOF, the intensity of the signals is not quantitative. The possible hydrolysis sites in the sequence are indicated with the arrows in the diagram, with the direction of subsequent degradation indicated by the horizontal arrows above the sequence.

Figure 18B:
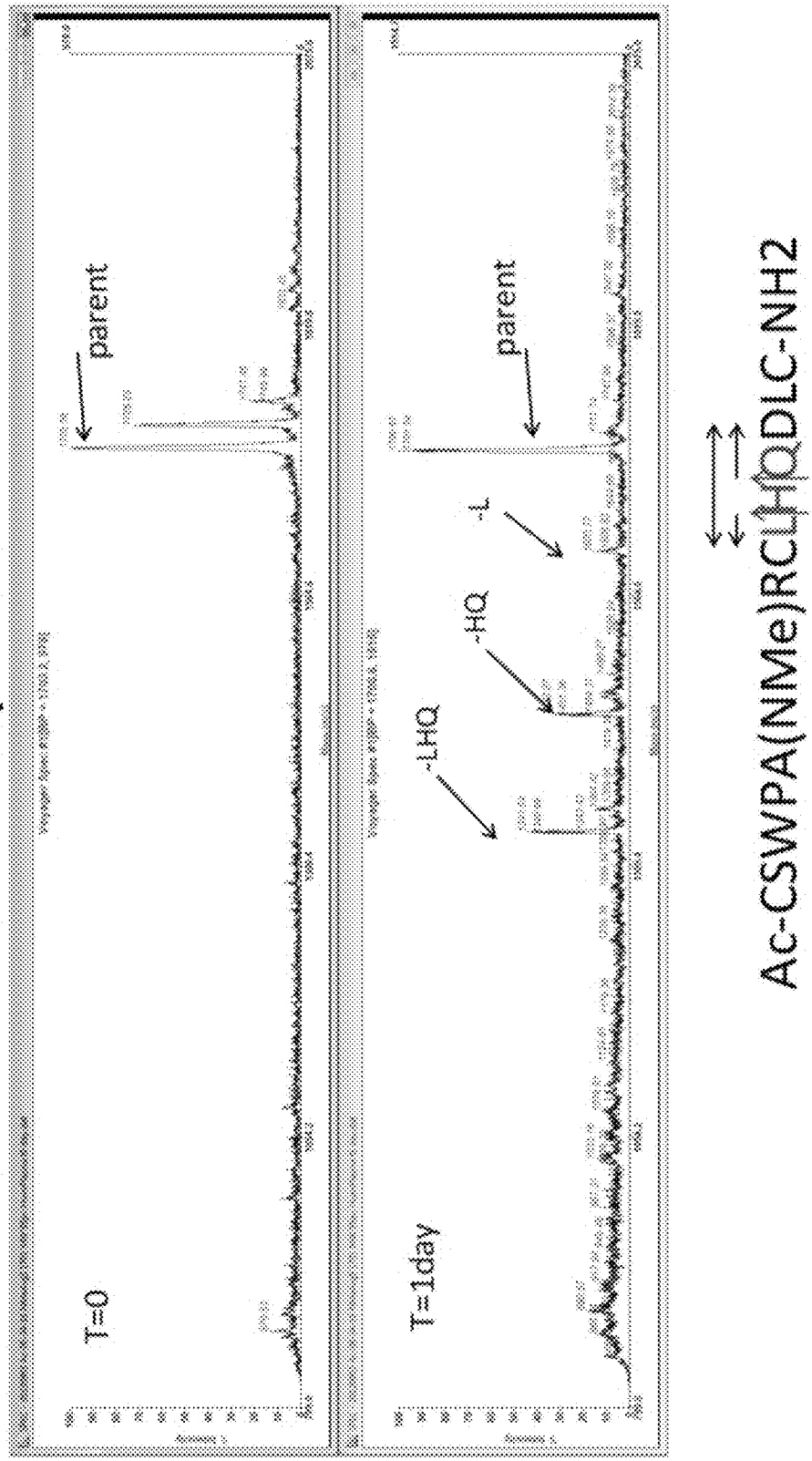

FIG. 18b Arg5 N-methylated 06-34-18 (SEQ ID NO: 223) is subjected to human plasma. This peptide has enhanced stability in rat plasma. In human plasma, however, the peptide is not stable, as exemplified by the appearance of fragments lacking His7-Gln8, Leu6, and Leu6-His7-Gln8 in Loop2. Due to the nature of MALDI-TOF, the intensity of the signals is not quantitative.

Figure 19A:
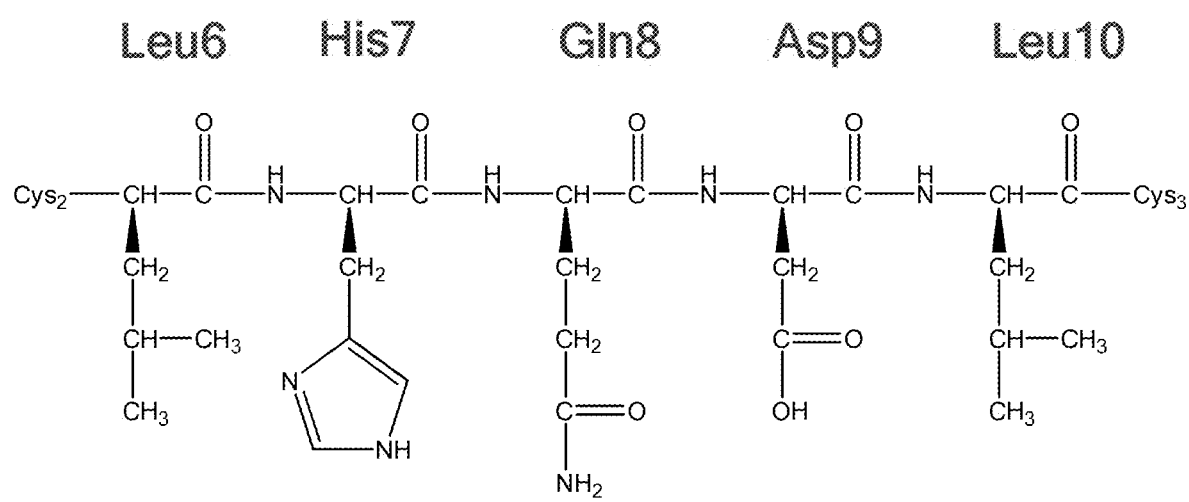

FIG. 19a Chemical Structure of Loop 2 of 06-34-18 (SEQ ID NO: 198)

Figure 19B:
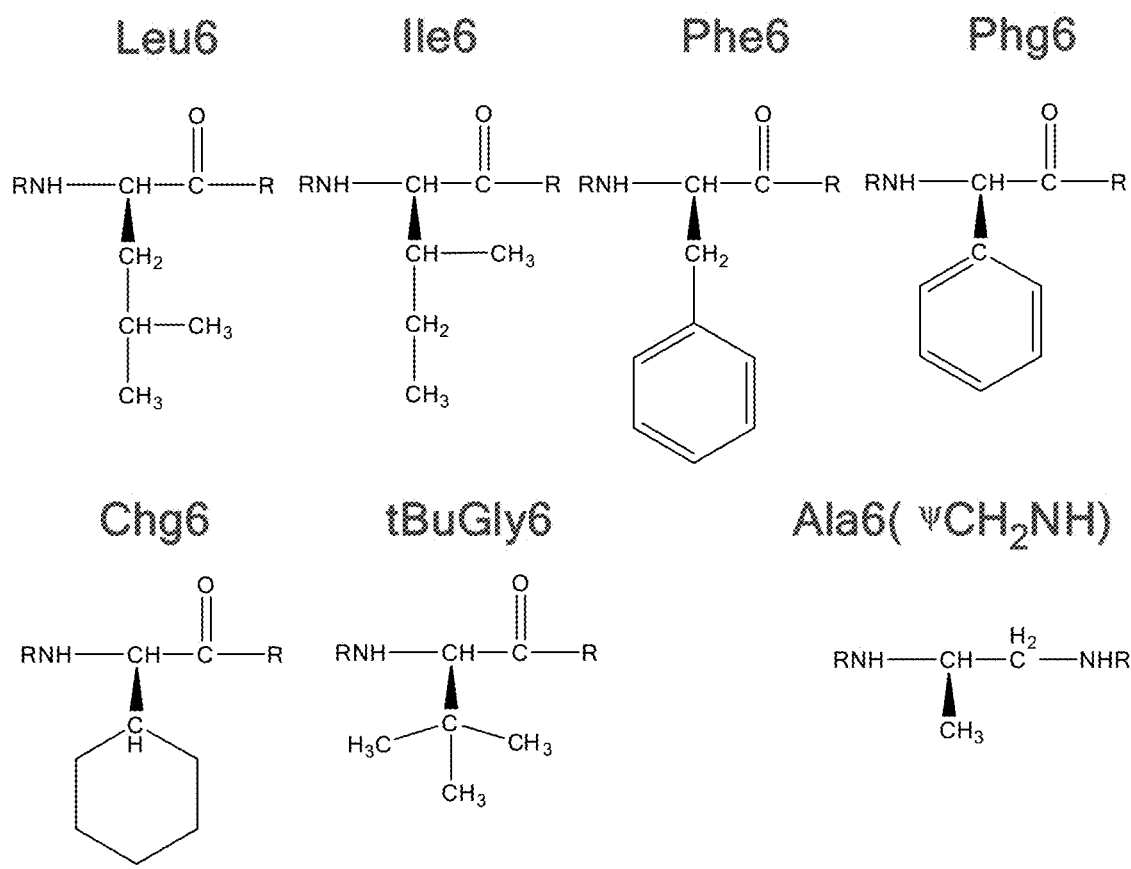

FIG. 19b Summary of structures employed at position 6 in Loop 2. The non-standard amino acid acronyms are defined in the Methods and Table 7.

Figure 19C:
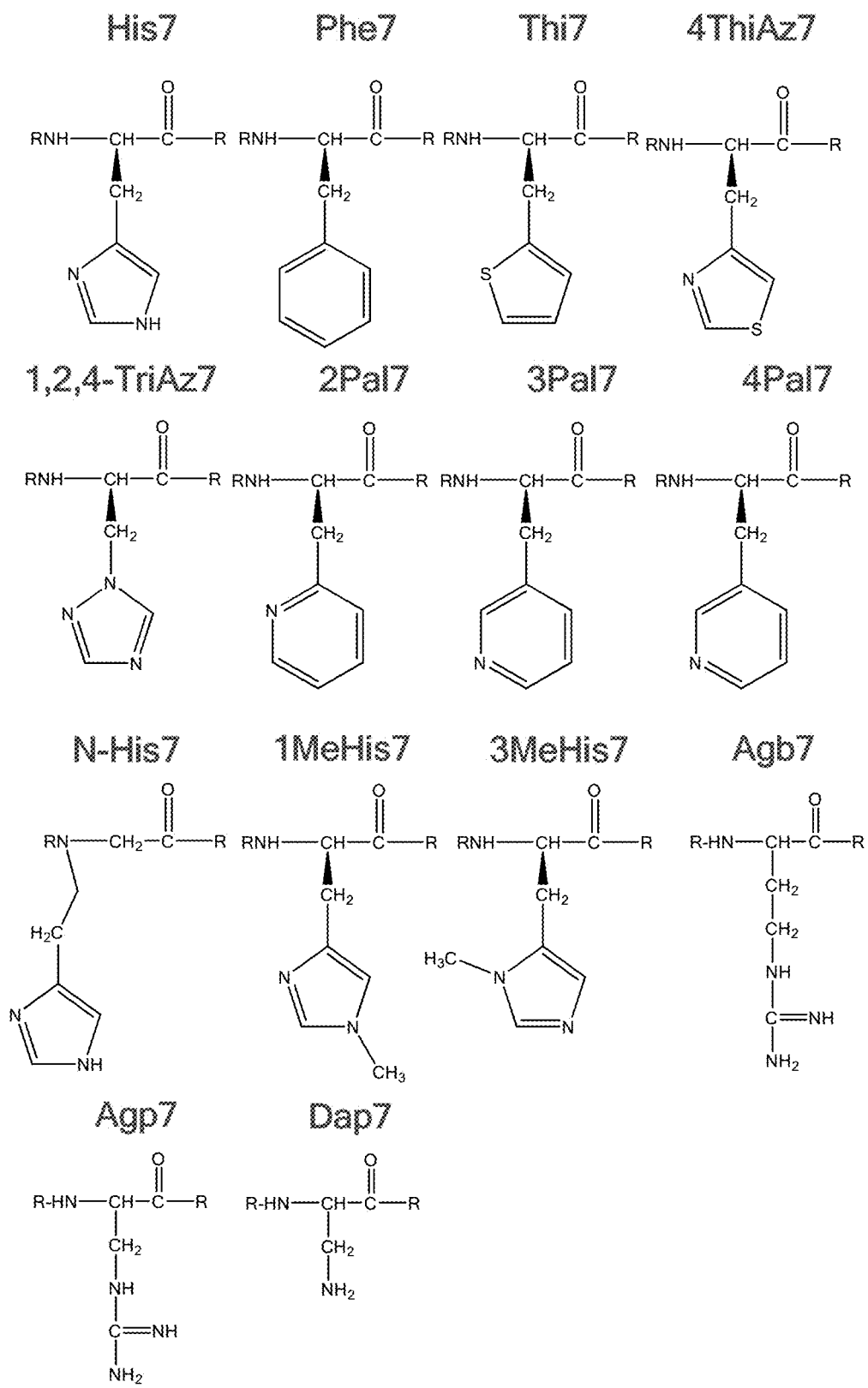

FIG. 19c Summary of structures employed at position 7 in Loop 2. The non-standard amino acid acronyms are defined in the Methods and Table 7.

Figure 19D:
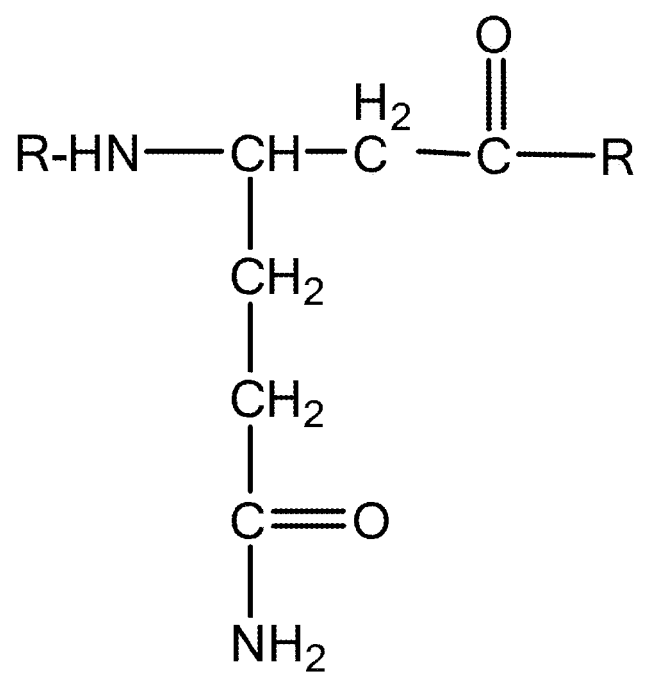

FIG. 19d Summary of structures employed at position 8 in Loop 2. The non-standard amino acid acronyms are defined in the Methods and Table 7.

Figure 20A:
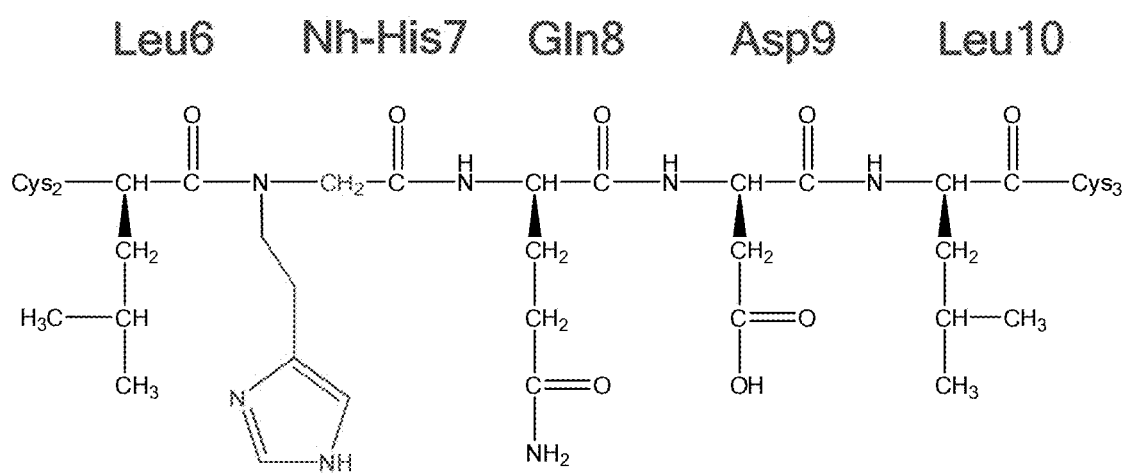

FIG. 20a Structure of N-His Peptoid within Loop 2 of 06-34-18 (SEQ ID NO: 199). A homohistidine side chain was introduced on the Nα, while Cα loses its chiral center.

Figure 20B:
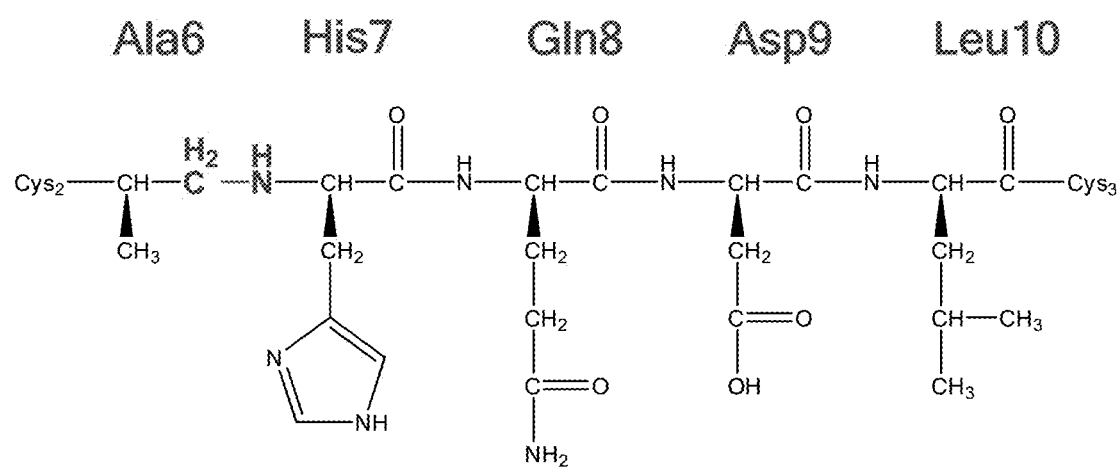

FIG. 20b Structure of the reduced amide between position 6 and 7 in Loop 2 of 06-34-18 (SEQ ID NO: 200). The methylene in place of the carbonyl removes the scissile peptide bond.

Figure 21A:
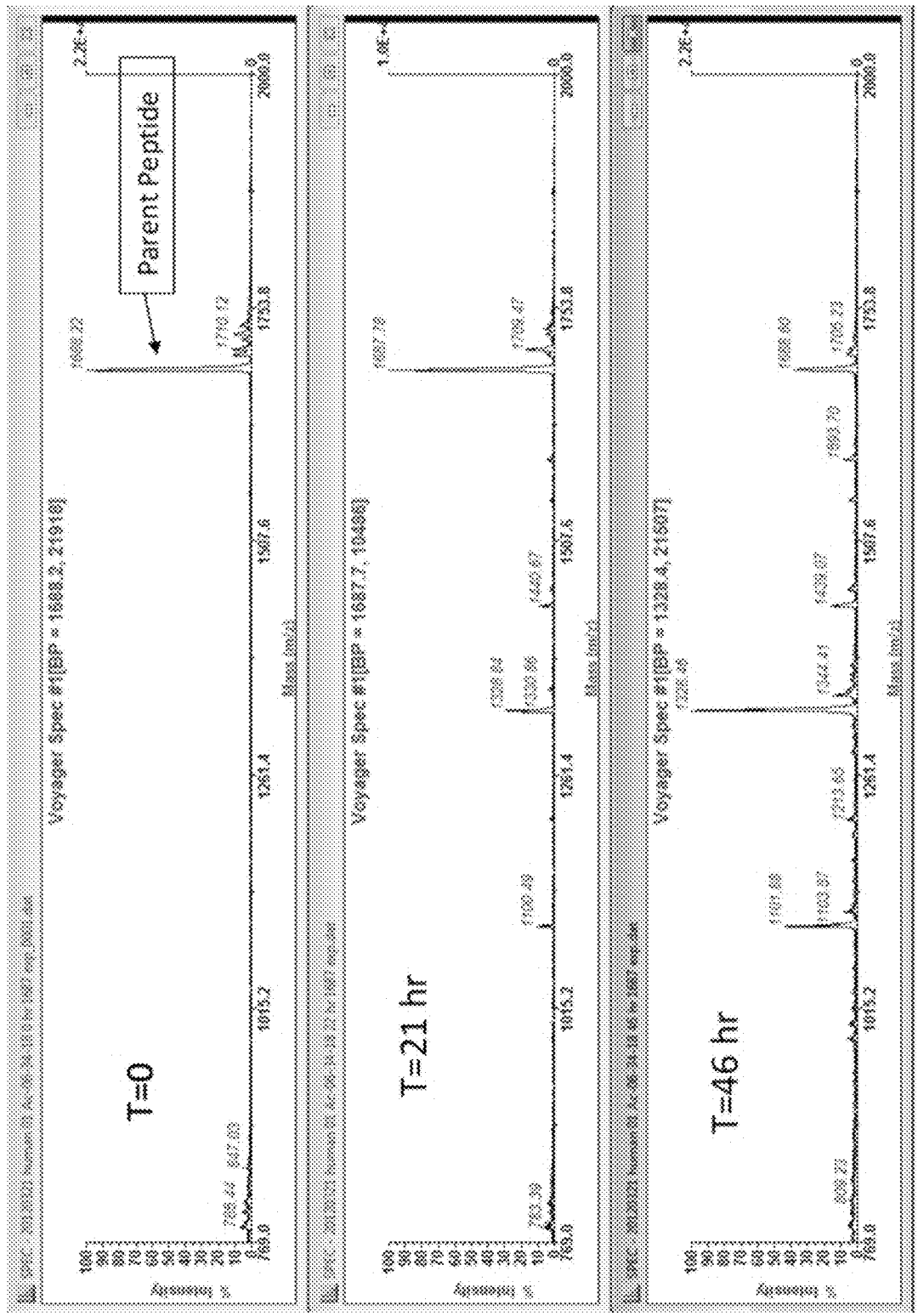

FIG. 21a Comparative stability of wildtype (06-34-18) at t=0, 21 and 46 hrs in human plasma.

Figure 21B:
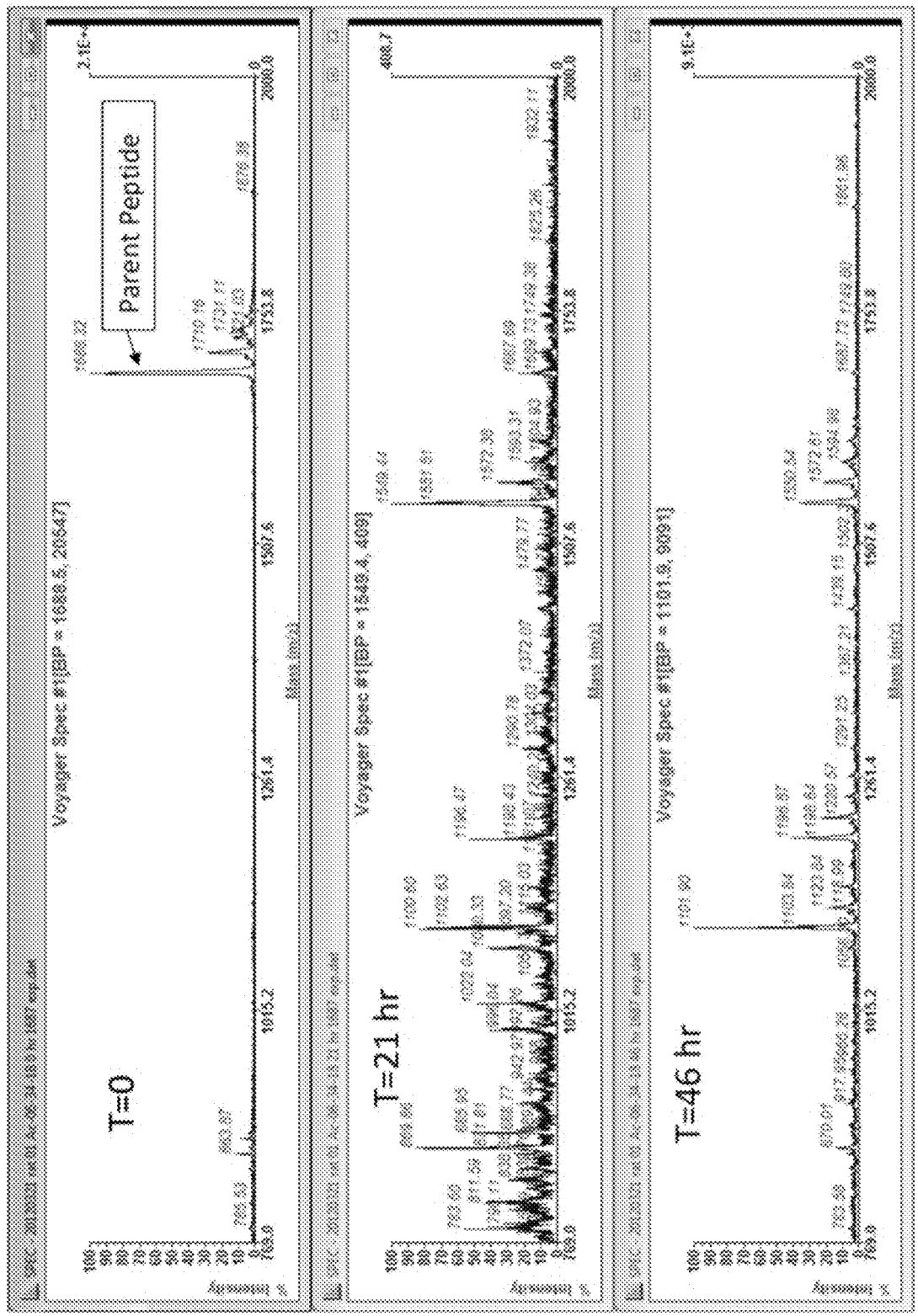

FIG. 21b Comparative stability of wildtype (06-34-18) at t=0, 21 and 46 hrs in rat plasma.

Figure 21C:
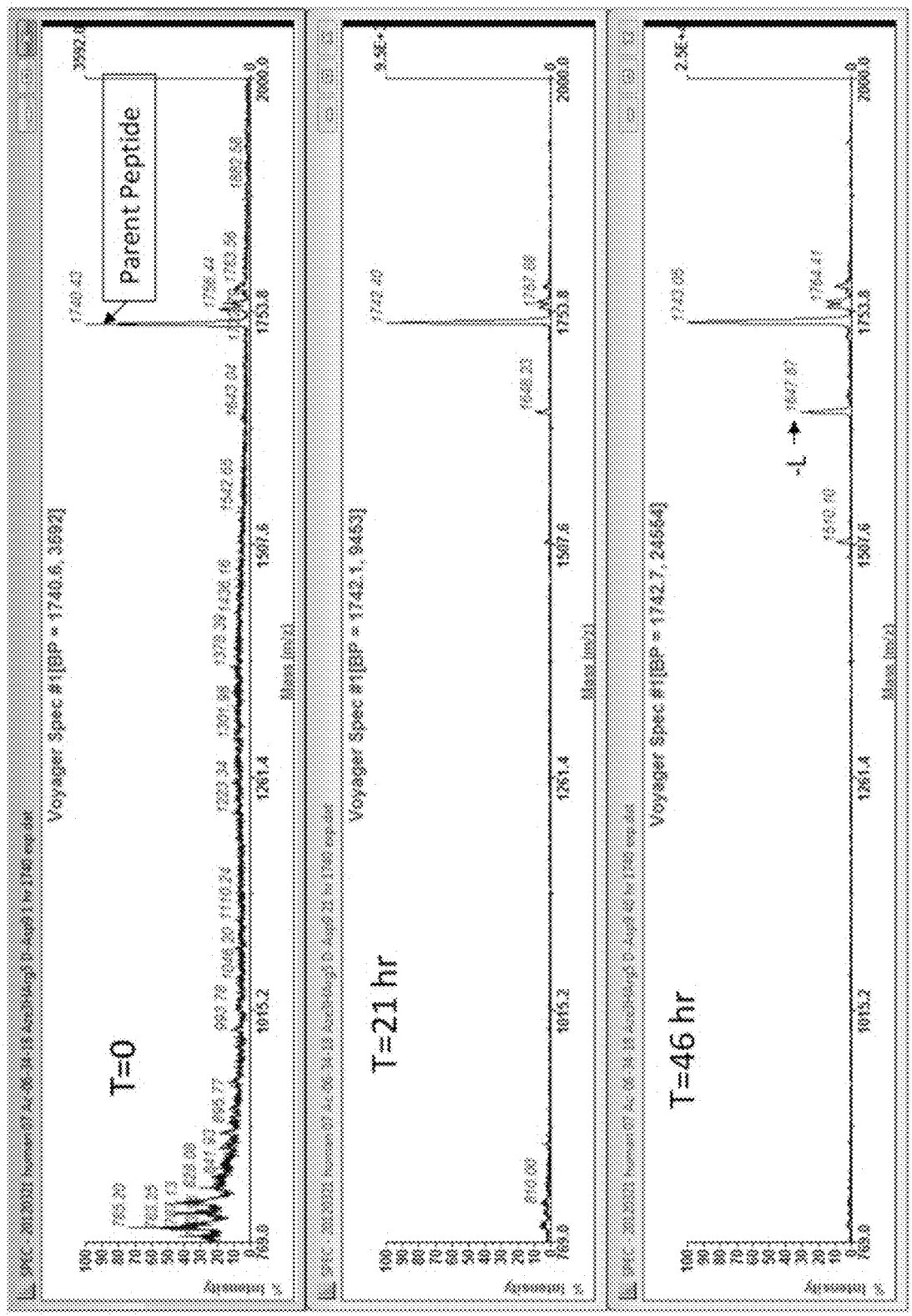

FIG. 21c Comparative stability of (06-34-18) Phe2 Aze3 Tyr4 HArg5 D-Asp9 (SEQ ID NO: 224) at t=0, 21 and 46 hrs in human plasma.

Figure 21D:
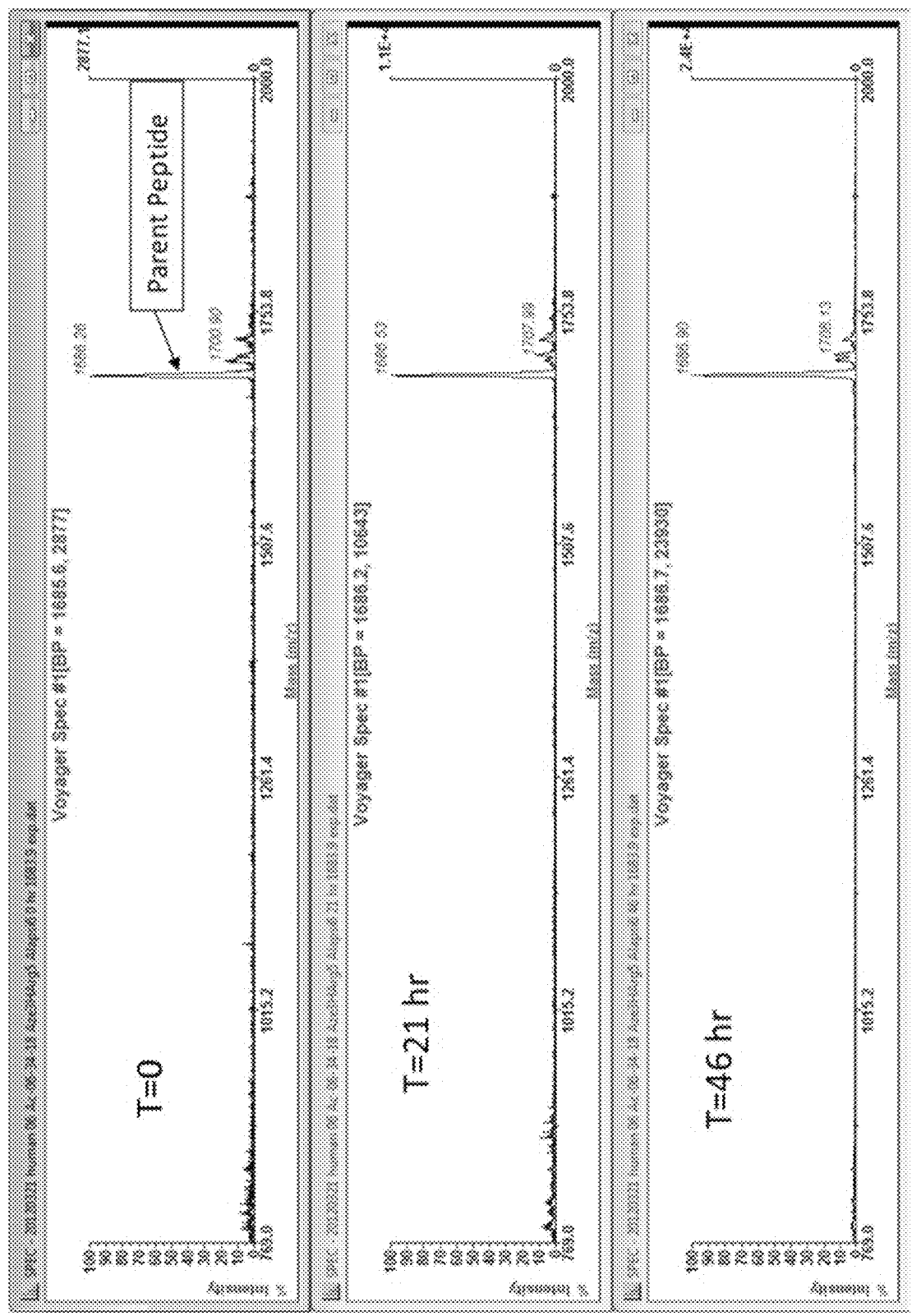

FIG. 21d Comparative stability of Ac-(06-34-18) Phe2 Aze3 Tyr4 HArg5 Ala(ψCH2NH)6 (SEQ ID NO: 201) at t=0, 21 and 46 hrs in human plasma.

Figure 21E:
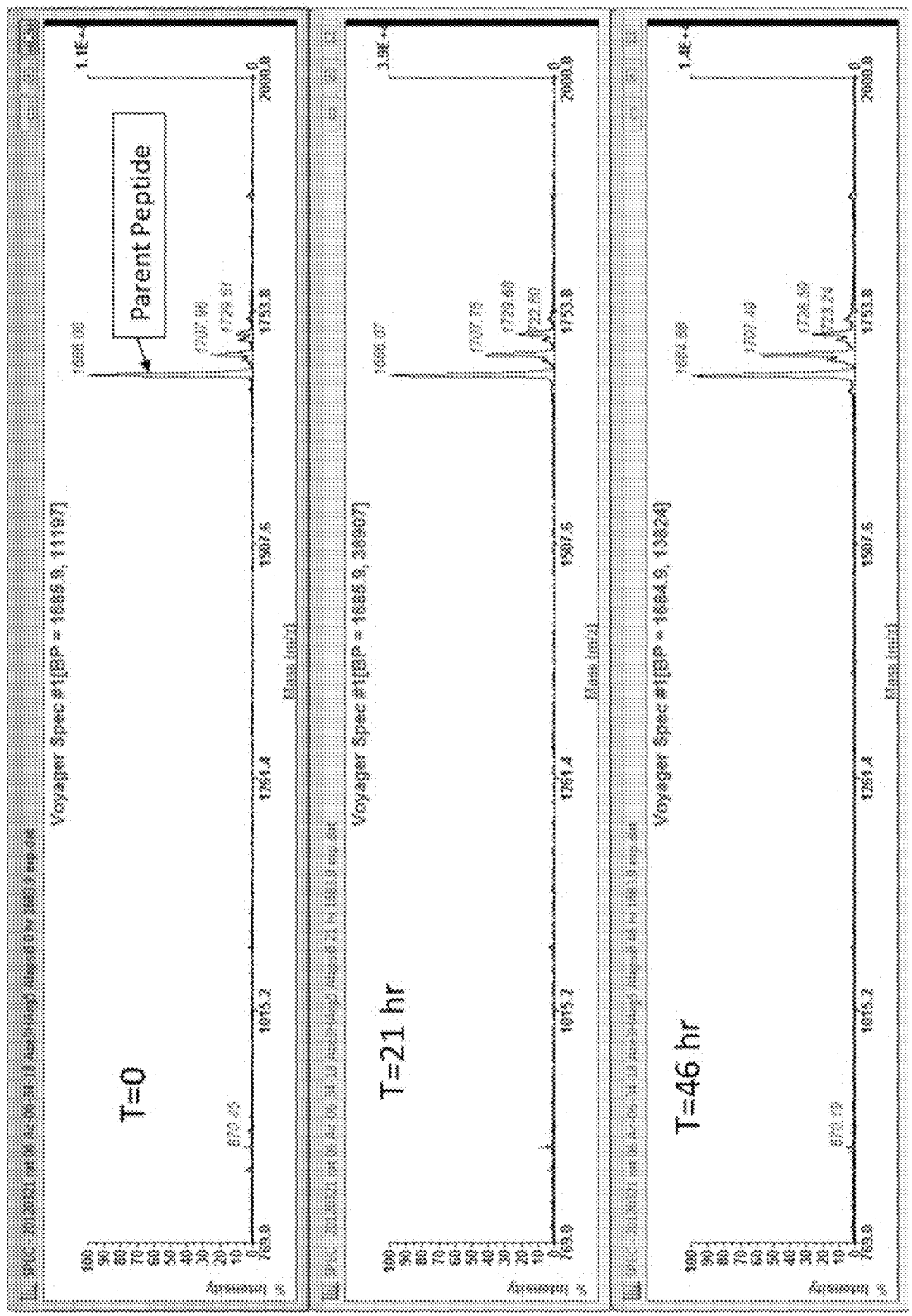

FIG. 21e Comparative stability of Ac-(06-34-18) Phe2 Aze3 Tyr4 HArg5 Ala(ψCH2NH)6 (SEQ ID NO: 201) at t=0, 21 and 46 hrs in rat plasma.

Figure 22:
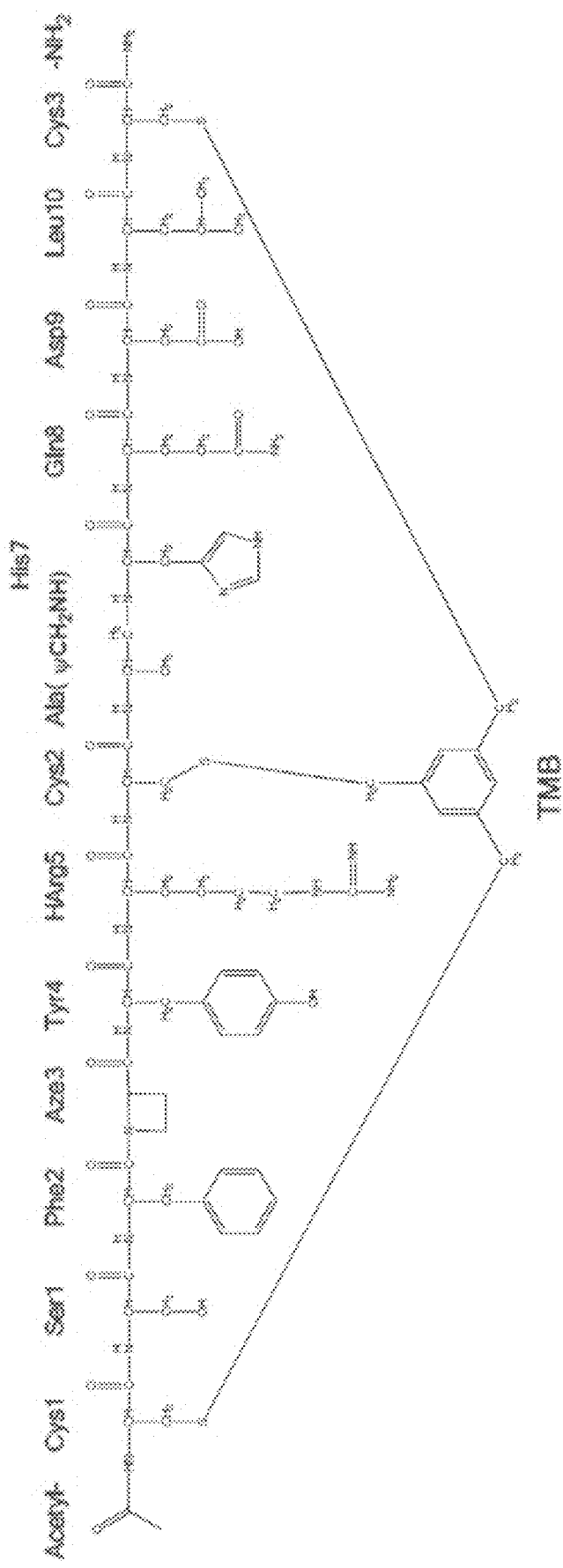

FIG. 22 Full chemical structure of Ac-(06-34-18) Phe2 Aze3 Tyr4 HArg5 Ala(ψCH2NH)6 (SEQ ID NO: 201). All amino acids are in the L-enantiomeric form.

Figure 23:
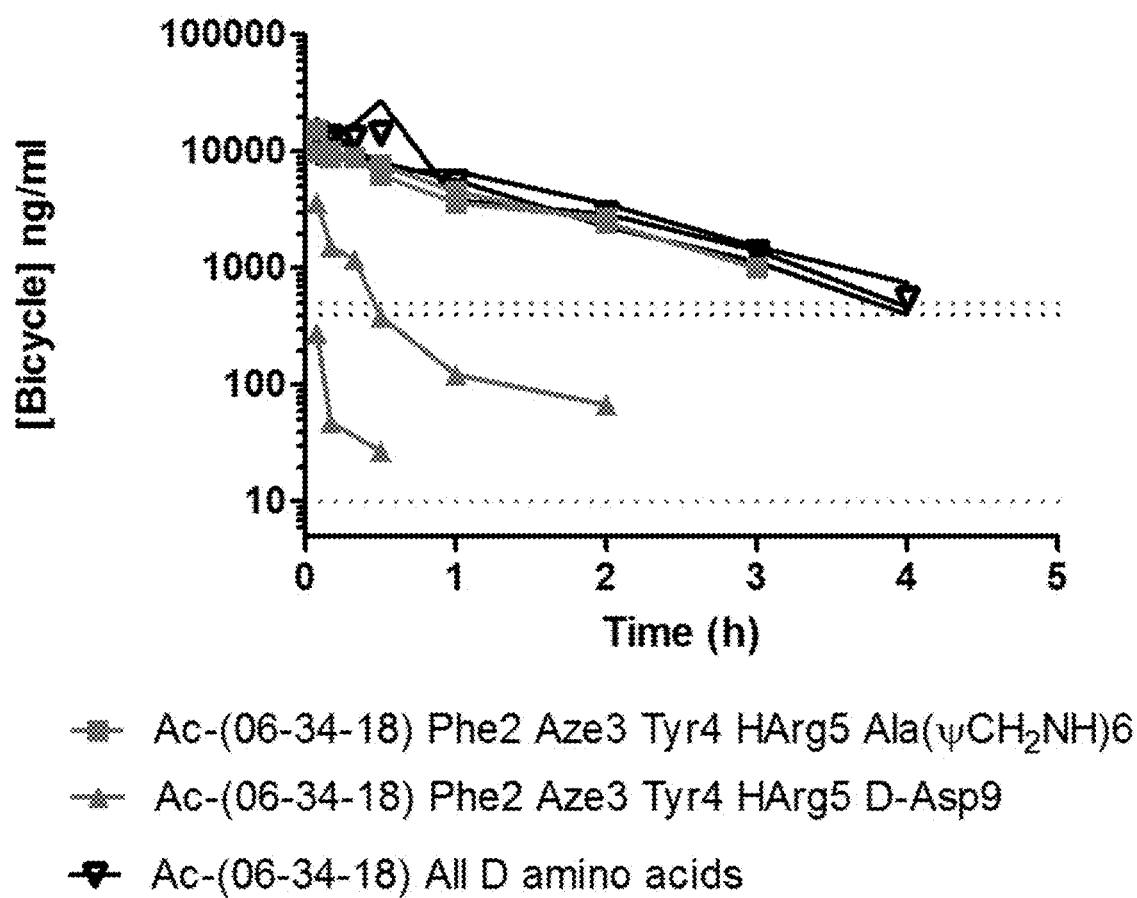

FIG. 23 Rat pharmacokinetic analysis of peptides Ac-(06-34-18) Phe2 Aze3 Tyr4 HArg5 Ala(ψCH2NH)6 (SEQ ID NO: 201) and Ac-(06-34-18) Phe2 Aze3 Tyr4 HArg5 D-Asp9 (SEQ ID NO: 224) compared to the proteolytically stable but pharmacologically inert all-D enantiomer of Ac-(06-34-18). Note the clearance of Ac-(06-34-18) Phe2 Aze3 Tyr4 HArg5 Ala(ψCH2NH)6 (SEQ ID NO: 201) is closely ressembling that of the D amino acid control peptide "Ac-(06-34-18) all D". The horizontal dotted lines indicate the limit of quantification for each of the respective peptides.

Figure 24:
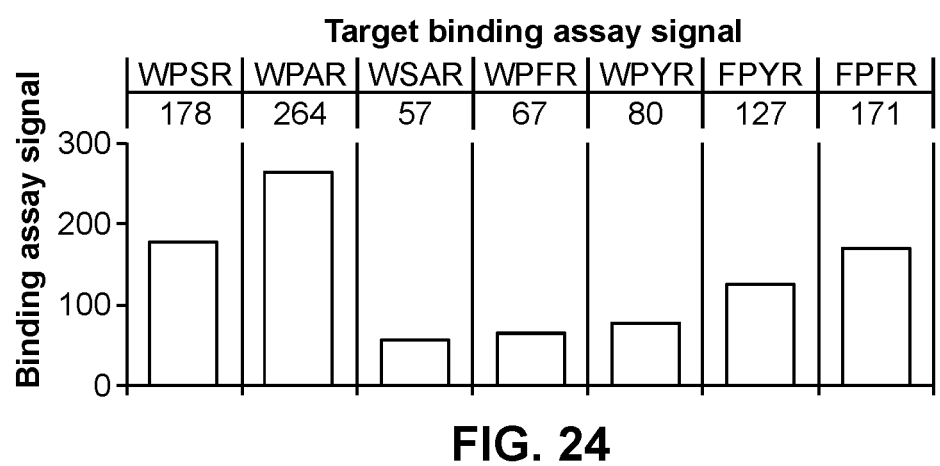

FIG. 24 Human plasma Kallikrein binding of particular motifs at positions 2, 3, 4 & 5 (with positions 1, 6, 7, 8, 9 &10 fixed to those of 06-34-03).

DETAILED DESCRIPTION OF THE INVENTION

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

A peptide ligand, as referred to herein, refers to a peptide covalently bound to a molecular scaffold. Typically, such peptides comprise two or more reactive groups which are capable of forming covalent bonds to the scaffold, and a sequence subtended between said reactive groups which is referred to as the loop sequence, since it forms a loop when the peptide is bound to the scaffold. In the present case, the peptides comprise at least three reactive groups, and form at least two loops on the scaffold.

The reactive groups are groups capable of forming a covalent bond with the molecular scaffold. Typically, the reactive groups are present on amino acid side chains on the peptide. Examples are amino-containing groups such as cysteine, lysine and selenocysteine.

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore be multispecific. For example, they bind to two targets, and are dual specific. The binding may be independent, which would mean that the binding sites for the targets on the peptide are not structurally hindered by the binding of one or other of the targets. In this case both targets can be bound independently. More generally it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific as a result of modulation of loop length.

If the ligands are truly bispecific, in one embodiment at least one of the target specificities of the ligands will be common amongst the ligands selected, and the level of that specificity can be modulated by the methods disclosed herein. Second or further specificities need not be shared, and need not be the subject of the procedures set forth herein.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. It is not a cross-linker, in that it does not merely replace a disulphide bond; instead, it provides two or more attachment points for the peptide. Suitably, the molecular scaffold comprises at least three attachment points for the peptide, referred to as scaffold reactive groups. These groups are capable of reacting to the reactive groups on the peptide to form a covalent bond. Preferred structures for molecular scaffolds are described below.

Screening for binding activity (or any other desired activity) is conducted according to methods well known in the art, for instance from phage display technology. For example, targets immobilised to a solid phase can be used to identify and isolate binding members of a repertoire. Screening allows selection of members of a repertoire according to desired characteristics.

The term library refers to a mixture of heterogeneous polypeptides or nucleic acids. The library is composed of members, which are not identical. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Under some conditions, each individual organism or cell contains only one or a limited number of library members.

In one embodiment, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

In one embodiment, a library of nucleic acids encodes a repertoire of polypeptides. Each nucleic acid member of the library typically has a sequence related to one or more other members of the library. By related sequence is meant an amino acid sequence having at least 50% identity, for example at least 60% identity, for example at least 70% identity, for example at least 80% identity, for example at least 90% identity, for example at least 95% identity, for example at least 98% identity, for example at least 99% identity to at least one other member of the library. Identity can be judged across a contiguous segment of at least 3 amino acids, for example at least 4, 5, 6, 7, 8, 9 or 10 amino acids, for example least 12 amino acids, for example least 14 amino acids, for example least 16 amino acids, for example least 17 amino acids or the full length of the reference sequence.

A repertoire is a collection of variants, in this case polypeptide variants, which differ in their sequence. Typically, the location and nature of the reactive groups will not vary, but the sequences forming the loops between them can be randomised. Repertoires differ in size, but should be considered to comprise at least $10^2$ members. Repertoires of $10^{11}$ or more members can be constructed.

A set of polypeptide ligands, as used herein, refers to a plurality of polypeptide ligands which can be subjected to selection in the methods described. Potentially, a set can be a repertoire, but it may also be a small collection of polypeptides, from at least 2 up to 10, 20, 50, 100 or more.

A group of polypeptide ligands, as used herein, refers to two or more ligands. In one embodiment, a group of ligands comprises only ligands which share at least one target specificity. Typically, a group will consist of from at least 2, 3, 4, 5, 6, 7, 8, 9 or 10, 20, 50, 100 or more ligands. In one embodiment, a group consists of 2 ligands.

(A) Construction of Peptide Ligands
(i) Molecular Scaffold

Molecular scaffolds are described in, for example, WO2009098450 and references cited therein, particularly WO2004077062 and WO2006078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer.

In one embodiment the molecular scaffold is a compound of known toxicity, for example of low toxicity. Examples of suitable compounds include cholesterols, nucleotides, steroids, or existing drugs such as tamazepam.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-Tris(bromomethyl)benzene ('TBMB'), or a derivative thereof.

In one embodiment, the molecular scaffold is 2,4,6-Tris (bromomethyl)mesitylene. It is similar to 1,3,5-Tris(bromomethyl)benzene but contains additionally three methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

(ii) Polypeptide

The reactive groups of the polypeptides can be provided by side chains of natural or non-natural amino acids. The reactive groups of the polypeptides can be selected from thiol groups, amino groups, carboxyl groups, guanidinium groups, phenolic groups or hydroxyl groups. The reactive groups of the polypeptides can be selected from azide, keto-carbonyl, alkyne, vinyl, or aryl halide groups. The reactive groups of the polypeptides for linking to a molecular scaffold can be the amino or carboxy termini of the polypeptide.

In some embodiments each of the reactive groups of the polypeptide for linking to a molecular scaffold are of the same type. For example, each reactive group may be a cysteine residue. Further details are provided in WO2009098450.

In some embodiments the reactive groups for linking to a molecular scaffold may comprise two or more different types, or may comprise three or more different types. For example, the reactive groups may comprise two cysteine residues and one lysine residue, or may comprise one cysteine residue, one lysine residue and one N-terminal amine.

Cysteine can be employed because it has the advantage that its reactivity is most different from all other amino acids. Scaffold reactive groups that could be used on the molecular scaffold to react with thiol groups of cysteines are alkyl halides (or also named halogenoalkanes or haloalkanes). Examples are bromomethylbenzene (the scaffold reactive group exemplified by TBMB) or iodoacetamide. Other scaffold reactive groups that are used to couple selectively compounds to cysteines in proteins are maleimides. Examples of maleimides which may be used as molecular scaffolds in the invention include: tris-(2-maleimidoethyl)amine, tris-(2-maleimidoethyl)benzene, tris-(maleimido)benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Lysines (and primary amines of the N-terminus of peptides) are also suited as reactive groups to modify peptides on phage by linking to a molecular scaffold. However, they are more abundant in phage proteins than cysteines and there is a higher risk that phage particles might become cross-linked or that they might lose their infectivity. Nevertheless, it has been found that lysines are especially useful in intramolecular reactions (e.g when a molecular scaffold is already linked to the phage peptide) to form a second or consecutive linkage with the molecular scaffold. In this case the molecular scaffold reacts preferentially with lysines of the displayed peptide (in particular lysines that are in close proximity). Scaffold reactive groups that react selectively with primary amines are succinimides, aldehydes or alkyl halides. In the bromomethyl group that is used in a number of the accompanying examples, the electrons of the benzene ring can stabilize the cationic transition state. This particular aryl halide is therefore 100-1000 times more reactive than alkyl halides. Examples of succinimides for use as molecular scaffold include tris-(succinimidyl aminotriacetate), 1,3, 5-Benzenetriacetic acid. Examples of aldehydes for use as molecular scaffold include Triformylmethane. Examples of alkyl halides for use as molecular scaffold include 1,3,5-Tris(bromomethyl)-2,4,6-trimethylbenzene, 1,3,5-Tris(bromomethyl) benzene, 1,3,5-Tris(bromomethyl)-2,4,6-triethylbenzene.

The amino acids with reactive groups for linking to a molecular scaffold may be located at any suitable positions within the polypeptide. In order to influence the particular structures or loops created, the positions of the amino acids having the reactive groups may be varied by the skilled operator, e.g. by manipulation of the nucleic acid encoding the polypeptide in order to mutate the polypeptide produced. By such means, loop length can be manipulated in accordance with the present teaching.

For example, the polypeptide can comprise the sequence $AC(X)_nC(X)_mCG$ (SEQ ID NO: 10), wherein X stands for a random natural amino acid, A for alanine, C for cysteine and G for glycine and n and m, which may be the same or different, are numbers between 3 and 6.

(iii) Reactive Groups of the Polypeptide

The molecular scaffold of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group. Again, details may be found in WO2009098450.

Examples of reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

The polypeptides of the invention contain at least three reactive groups. Said polypeptides can also contain four or more reactive groups. The more reactive groups are used, the more loops can be formed in the molecular scaffold.

In a preferred embodiment, polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the polypeptide with the molecular core. If only one product isomer can be formed, the assignment of the nucleic acid to the product isomer is clearly defined. If multiple product isomers are formed, the nucleic acid cannot give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment of the invention, polypeptides with four reactive groups are generated. Reaction of said polypeptides with a molecular scaffold/molecular core having a tetrahedral symmetry generates two product isomers. Even though the two different product isomers are encoded by one and the same nucleic acid, the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the polypeptide of the invention are reacted with molecular linkers wherein said linkers are capable to react with a molecular scaffold so that the linker will intervene between the molecular scaffold and the polypeptide in the final bonded state.

In some embodiments, amino acids of the members of the libraries or sets of polypeptides can be replaced by any natural or non-natural amino acid. Excluded from these exchangeable amino acids are the ones harbouring functional groups for cross-linking the polypeptides to a molecular core, such that the loop sequences alone are exchangeable. The exchangeable polypeptide sequences have either random sequences, constant sequences or sequences with random and constant amino acids. The amino acids with reactive groups are either located in defined positions within the polypeptide, since the position of these amino acids determines loop size.

In one embodiment, an polypeptide with three reactive groups has the sequence $(X)_lY(X)_mY(X)_nY(X)_o$ (SEQ ID NO: 215), wherein Y represents an amino acid with a reactive group, X represents a random amino acid, m and n are numbers between 3 and 6 defining the length of intervening polypeptide segments, which may be the same or different, and l and o are numbers between 0 and 20 defining the length of flanking polypeptide segments.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase. Further details can be found in WO2009098450 or Heinis, et al., *Nat Chem Biol* 2009, 5 (7), 502-7.

(iv) Combination of Loops to Form Multispecific Molecules

Loops from peptide ligands, or repertoires of peptide ligands, are advantageously combined by sequencing and de novo synthesis of a polypeptide incorporating the combined loops. Alternatively, nucleic acids encoding such polypeptides can be synthesised.

Where repertoires are to be combined, particularly single loop repertoires, the nucleic acids encoding the repertoires are advantageously digested and re-ligated, to form a novel repertoire having different combinations of loops from the constituent repertoires. Phage vectors can include polylinkers and other sites for restriction enzymes which can provide unique points for cutting and relegation the vectors, to create the desired multispecific peptide ligands. Methods for manipulating phage libraries are well known in respect of antibodies, and can be applied in the present case also.

(v) Attachment of Effector Groups and Functional Groups

Effector and/or functional groups can be attached, for example, to the N or C termini of the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further preferred embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox is protein of *Drosophila* (Antennapedia), e.g. as described in Chen and Harrison, Biochemical Society Transactions (2007) Volume 35, part 4, p 821 "Cell-penetrating peptides in drug development: enabling intracellular targets" and "Intracellular delivery of large molecules and small peptides by cell penetrating peptides" by Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J Biol. Chem. Volume 269 p 10444 "The third helix of the Antennapedia homeodomain translocates through biological membranes"), the 18 amino acid 'model amphipathic peptide' (Oehlke et al (1998) Biochim Biophys Acts Volume 1414 p 127 "Cellular uptake of an alpha-helical amphipathic model peptide with the potential to deliver polar compounds into the cell interior non-endocytically") and arginine rich regions of the HIV TAT protein. Non peptidic approaches include the use of small molecule mimics or SMOCs that can be easily attached to biomolecules (Okuyama et al (2007) Nature Methods Volume 4 p 153 'Small-molecule mimics of an a-helix for efficient transport of proteins into cells'. Other chemical strategies to add guanidinium groups to molecules also enhance cell penetration (Elson-Scwab et al (2007) J Biol Chem Volume 282 p 13585 "Guanidinylated Neomcyin Delivers Large Bioactive Cargo into cells through a heparin Sulphate Dependent Pathway"). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a t half-life of a day or more. In a further embodiment still, it will be in the range 12 to 26 hours.

Functional groups include drugs, such as cytotoxic agents for cancer therapy. These include Alkylating agents such as Cisplatin and carboplatin, as well as oxaliplatin, mechlorethamine, cyclophosphamide, chlorambucil, ifosfamide; Anti-metabolites including purine analogs azathioprine and mercaptopurine)) or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include Antitumour antibiotics which include the immunosuppressant dactinomycin (which is used in kidney transplantations), doxorubicin, epirubicin, bleomycin and others.

Possible effector groups also include enzymes, for instance such as carboxypeptidase G2 for use in enzyme/prodrug therapy, where the peptide ligand replaces antibodies in ADEPT.

(vi) Synthesis

It should be noted that once a polypeptide of interest is isolated or identified according to the present invention, then its subsequent synthesis may be simplified wherever possible. Thus, groups or sets of polypeptides need not be produced by recombinant DNA techniques. For example, the sequence of polypeptides of interest may be determined, and they may be manufactured synthetically by standard techniques followed by reaction with a molecular scaffold in vitro. When this is performed, standard chemistry may be used since there is no longer any need to preserve the functionality or integrity of the genetically encoded carrier particle, such as phage. This enables the rapid large scale preparation of soluble material for further downstream experiments or validation. In this regard, large scale preparation of the candidates or leads identified by the methods of the present invention could be accomplished using conventional chemistry such as that disclosed in Timmerman et al.

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis, rather than on the phage.

Optionally amino acid residues in the polypeptide of interest may be substituted when manufacturing a conjugate or complex e.g. after the initial isolation/identification step.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard protein chemistry may be used to introduce an activatable N- or C-terminus. Alternatively additions may be made by fragment condensation or native chemical ligation e.g. as described in (Dawson P E, Muir T W, Clark-Lewis I, Kent, S B H. 1994. Synthesis of Proteins by Native Chemical Ligation. Science 266:776-779), or by enzymes, for example using subtiligase as described in (Subtiligase: a tool for semisynthesis of proteins Chang T K, Jackson D Y, Burnier J P, Wells J A Proc Natl Acad Sci USA. 1994 Dec. 20; 91(26):12544-8 or in Bioorganic & Medicinal Chemistry Letters Tags for labelling protein N-termini with subtiligase for proteomics Volume 18, Issue 22, 15 Nov. 2008, Pages 6000-6003 Tags for labeling protein N-termini with subtiligase for proteomics; Hikari A. I. Yoshihara, Sami Mahrus and James A. Wells).

Alternatively, the peptides may be extended or modified by further conjugation through disulphide bonds. This has the additional advantage of allowing the first and second peptide to dissociate from each other once within the reducing environment of the cell. In this case, the molecular scaffold (eg. TBMB) could be added during the chemical synthesis of the first peptide so as to react with the three cysteine groups; a further cysteine could then be appended to the N-terminus of the first peptide, so that this cysteine only reacted with a free cysteine of the second peptide.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

(vii) Peptide Modification

To develop the bicyclic peptides (Bicycles; peptides conjugated to molecular scaffolds) into a suitable drug-like molecule, whether that be for injection, inhalation, nasal, ocular, oral or topical administration, a number of properties need considered. The following at least need to be designed into a given lead Bicycle:

protease stability, whether this concerns Bicycle stability to plasma proteases, epithelial ("membrane-anchored") proteases, gastric and intestinal proteases, lung surface proteases, intracellular proteases and the like. Protease stability should be maintained between different species such that a Bicycle lead candidate can be developed in animal models as well as administered with confidence to humans.

replacement of oxidation-sensitive residues, such as tryptophan and methionine with oxidation-resistant analogues in order to improve the pharmaceutical stability profile of the molecule a desirable solubility profile, which is a function of the proportion of charged and hydrophilic versus hydrophobic residues, which is important for formulation and absorption purposes correct balance of charged versus hydrophobic residues, as hydrophobic residues influence the degree of plasma protein binding and thus the concentration of the free available fraction in plasma, while charged residues (in particular arginines) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic residues may reduce irritation at the injection site (were the peptide drug administered subcutaneously).

a tailored half-life, depending on the clinical indication and treatment regimen. It may be prudent to develop an unmodified molecule for short exposure in an acute illness management setting, or develop a bicyclic peptide with chemical modifications that enhance the plasma half-life, and hence be optimal for the management of more chronic disease states.

Approaches to stabilise therapeutic peptide candidates against proteolytic degradation are numerous, and overlap with the peptidomimetics field (for reviews see Gentilucci et al, Curr. Pharmaceutical Design, (2010), 16, 3185-203, and Nestor et al, Curr. Medicinal Chem (2009), 16, 4399-418). These include Cyclisation of peptide N- and C-terminal capping, usually N-terminal acetylation and C-terminal amidation.

Alanine scans, to reveal and potentially remove the proteolytic attack site(s).

D-amino acid replacement, to probe the steric requirements of the amino acid side chain, to increase proteolytic stability by steric hindrance and by a propensity of D-amino acids to stabilise β-turn conformations (Tugyi et a/(2005) PNAS, 102(2), 413-418).

N-methyl/N-alkyl amino acid replacement, to impart proteolytic protection by direct modification of the scissile amide bond (Fiacco et al, Chembiochem. (2008), 9(14), 2200-3). N-methylation also has strong effect on the torsional angles of the peptide bond, and is believed to aid in cell penetration & oral availability (Biron et al (2008), Angew. Chem. Int. Ed., 47, 2595-99)

Incorporation of non-natural amino acids, i.e. by employing
- Isosteric/isoelectronic side chains that are not recognised by proteases, yet have no effect on target potency
- Constrained amino acid side chains, such that proteolytic hydrolysis of the nearby peptide bond is conformationally and sterically impeded. In particular, these concern proline analogues, bulky sidechains, Cα-disubstituted derivatives (where the simplest derivative is Aib, $H_2N-C(CH_3)_2-COOH$), and cyclo amino acids, a simple derivative being amino-cyclopropylcarboxylic acid).

Peptide bond surrogates, and examples include
- N-alkylation (see above, i.e. CO—NR)
- Reduced peptide bonds (CH2-NH—)
- Peptoids (N-alkyl amino acids, NR—$CH_2$—CO)
- Thio-amides (CS—NH)
- Azapeptides (CO—NH—NR)
- Trans-alkene (RHC=C—)
- Retro-inverso (NH—CO)
- Urea surrogates (NH—CO—NHR)

Peptide backbone length modulation
  i.e. $β^{2/3}$-amino acids, (NH—CR—$CH_2$—CO, NH—$CH_2$—CHR—CO), Substitutions on the alpha-carbon on amino acids, which constrains backbone conformations, the simplest derivative being Aminoisobutyric acid (Aib).

It should be explicitly noted that some of these modifications may also serve to deliberately improve the potency of the peptide against the target, or, for example to identify potent substitutes for the oxidation-sensitive amino acids (Trp and Met). It should also be noted that the Bicycle lead Ac-06-34-18(TMB)-NH2 already harbours two modifications that impart resistance to proteolytic degradation, these being N/C-terminal capping, and (bi)cyclisation.

(B) Repertoires, Sets and Groups of Polypeptide Ligands
(i) Construction of Libraries Libraries intended for selection may be constructed using techniques known in the art, for example as set forth in WO2004/077062, or biological systems, including phage vector systems as described herein. Other vector systems are known in the art, and include other phage (for instance, phage lambda), bacterial plasmid expression vectors, eukaryotic cell-based expression vectors, including yeast vectors, and the like. For example, see WO2009098450 or Heinis, et al., *Nat Chem Biol* 2009, 5 (7), 502-7.

Non-biological systems such as those set forth in WO2004/077062 are based on conventional chemical screening approaches. They are simple, but lack the power of biological systems since it is impossible, or at least impracticably onerous, to screen large libraries of peptide ligands. However, they are useful where, for instance, only a small number of peptide ligands needs to be screened. Screening by such individual assays, however, may be time-consuming and the number of unique molecules that can be tested for binding to a specific target generally does not exceed $10^6$ chemical entities.

In contrast, biological screening or selection methods generally allow the sampling of a much larger number of different molecules. Thus biological methods can be used in application of the invention. In biological procedures, molecules are assayed in a single reaction vessel and the ones with favourable properties (i.e. binding) are physically separated from inactive molecules. Selection strategies are available that allow to generate and assay simultaneously more than $10^{13}$ individual compounds. Examples for powerful affinity selection techniques are phage display, ribosome display, mRNA display, yeast display, bacterial display or RNA/DNA aptamer methods. These biological in vitro selection methods have in common that ligand repertoires are encoded by DNA or RNA. They allow the propagation and the identification of selected ligands by sequencing. Phage display technology has for example been used for the isolation of antibodies with very high binding affinities to virtually any target.

When using a biological system, once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected before mutagenesis and additional rounds of selection are performed.

Mutagenesis of nucleic acid sequences encoding structurally optimised polypeptides is carried out by standard molecular methods. Of particular use is the polymerase chain reaction, or PCR, (Mullis and Faloona (1987) Methods Enzymol., 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

Alternatively, given the short chain lengths of the polypeptides according to the invention, the variants can be synthesised de novo and inserted into suitable expression vectors. Peptide synthesis can be carried out by standard techniques known in the art, as described above. Automated peptide synthesisers are widely available, such as the Applied Biosystems ABI 433 (Applied Biosystems, Foster City, Calif., USA)

(ii) Genetically Encoded Diversity

In one embodiment, the polypeptides of interest are genetically encoded. This offers the advantage of enhanced diversity together with ease of handling. An example of a genetically polypeptide library is a mRNA display library. Another example is a replicable genetic display package (rgdp) library such as a phage display library. In one embodiment, the polypeptides of interest are genetically encoded as a phage display library.

Thus, in one embodiment the complex of the invention comprises a replicable genetic display package (rgdp) such as a phage particle. In these embodiments, the nucleic acid can be comprised by the phage genome. In these embodiments, the polypeptide can be comprised by the phage coat.

In some embodiments, the invention may be used to produce a genetically encoded combinatorial library of polypeptides which are generated by translating a number of nucleic acids into corresponding polypeptides and linking molecules of said molecular scaffold to said polypeptides.

The genetically encoded combinatorial library of polypeptides may be generated by phage display, yeast display, ribosome display, bacterial display or mRNA display.

Techniques and methodology for performing phage display can be found in WO2009098450.

In one embodiment, screening may be performed by contacting a library, set or group of polypeptide ligands with a target and isolating one or more member(s) that bind to said target.

In another embodiment, individual members of said library, set or group are contacted with a target in a screen and members of said library that bind to said target are identified.

In another embodiment, members of said library, set or group are simultaneously contacted with a target and members that bind to said target are selected.

The target(s) may be a peptide, a protein, a polysaccharide, a lipid, a DNA or a RNA.

The target may be a receptor, a receptor ligand, an enzyme, a hormone or a cytokine.

The target may be a prokaryotic protein, a eukaryotic protein, or an archeal protein. More specifically the target ligand may be a mammalian protein or an insect protein or a bacterial protein or a fungal protein or a viral protein.

The target ligand may be an enzyme, such as a protease.

It should be noted that the invention also embraces polypeptide ligands isolated from a screen according to the invention. In one embodiment the screening method(s) of the invention further comprise the step of: manufacturing a quantity of the polypeptide isolated as capable of binding to said targets.

The invention also relates to peptide ligands having more than two loops. For example, tricyclic polypeptides joined to a molecular scaffold can be created by joining the N- and C-termini of a bicyclic polypeptide joined to a molecular scaffold according to the present invention. In this manner, the joined N and C termini create a third loop, making a tricyclic polypeptide. This embodiment need not be carried out on phage, but can be carried out on a polypeptide-molecular scaffold conjugate as described herein. Joining the N- and C-termini is a matter of routine peptide chemistry. In case any guidance is needed, the C-terminus may be activated and/or the N- and C-termini may be extended for example to add a cysteine to each end and then join them by disulphide bonding. Alternatively the joining may be accomplished by use of a linker region incorporated into the N/C termini. Alternatively the N and C termini may be joined by a conventional peptide bond. Alternatively any other suitable means for joining the N and C termini may be employed, for example N—C-cyclization could be done by standard techniques, for example as disclosed in Linde et al. Peptide Science 90, 671-682 (2008) "Structure-activity relationship and metabolic stability studies of backbone cyclization and N-methylation of melanocortin peptides", or as in Hess et al. J. Med. Chem. 51, 1026-1034 (2008) "backbone cyclic peptidomimetic melanocortin-4 receptor agonist as a novel orally administered drug lead for treating obesity". One advantage of such tricyclic molecules is the avoidance of proteolytic degradation of the free ends, in particular by exoprotease action. Another advantage of a tricyclic polypeptide of this nature is that the third loop may be utilised for generally applicable functions such as BSA binding, cell entry or transportation effects, tagging or any other such use. It will be noted that this third loop will not typically be available for selection (because it is not produced on the phage but only on the polypeptide-molecular scaffold conjugate) and so its use for other such biological functions still advantageously leaves both loops 1 and 2 for selection/creation of specificity.

(iii) Phage Purification

Any suitable means for purification of the phage may be used. Standard techniques may be applied in the present invention. For example, phage may be purified by filtration or by precipitation such as PEG precipitation; phage particles may be produced and purified by polyethylene-glycol (PEG) precipitation as described previously. Details can be found in WO2009098450.

In case further guidance is needed, reference is made to Jespers et al (Protein Engineering Design and Selection 2004 17(10):709-713. Selection of optical biosensors from chemisynthetic antibody libraries.) In one embodiment phage may be purified as taught therein. The text of this publication is specifically incorporated herein by reference for the method of phage purification; in particular reference is made to the materials and methods section starting part way down the right-column at page 709 of Jespers et al.

Moreover, the phage may be purified as published by Marks et al J. Mol. Biol vol 222 pp 581-597, which is specifically incorporated herein by reference for the particular description of how the phage production/purification is carried out.

(iv) Reaction Chemistry

The present invention makes use of chemical conditions for the modification of polypeptides which advantageously retain the function and integrity of the genetically encoded element of the product. Specifically, when the genetically encoded element is a polypeptide displayed on the surface of a phage encoding it, the chemistry advantageously does not compromise the biological integrity of the phage. In general, conditions are set out in WO2009098450.

(C) Use of Polypeptide Ligands According to the Invention

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The peptide ligands of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Methods for the testing of systemic lupus erythematosus (SLE) in susceptible mice are known in the art (Knight et al. (1978) J Exp. Med., 147: 1653; Reinersten et al. (1978) New Eng. J: Med., 299: 515). Myasthenia Gravis (MG) is tested in SJL/J female mice by inducing the disease with soluble AchR protein from another species (Lindstrom et al. (1988) Adv. Inzn7unol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J; Immunol., 138: 179).

Generally, the present peptide ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

According to a further aspect of the invention, there is provided a method of preventing, suppressing or treating inflammatory states, allergic hypersensitivity, cancer, bacterial or viral infection, ophthalmic disorders and autoimmune disorders which comprises administering to a patient in need thereof a peptide ligand as defined herein.

Examples of suitable "ophthalmic disorders" (including exudative and/or inflammatory ophthalmic disorders, disorders related to impaired retinal vessel permeability and/or integrity, disorders related to retinal microvessel rupture leading to focal hemorrhages, back of the eye diseases, retinal diseases and front of the eye diseases) include but are not limited to: age related macular degeneration (ARMD), exudative macular degeneration (also known as "wet" or neovascular age-related macular degeneration (wet-AMD), macular oedema, aged disciform macular degeneration, cystoid macular oedema, palpebral oedema, retinal oedema, diabetic retinopathy, acute macular neuroretinopathy, central serous chorioretinopathy, chorioretinopathy, choroidal neovascularization, neovascular maculopathy, neovascular glaucoma, obstructive arterial and venous retinopathies (e.g. retinal venous occlusion or retinal arterial occlusion), central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, macular oedema occurring as a result of aetiologies such as disease (e.g. diabetic macular oedema), eye injury or eye surgery; retinal ischemia or degeneration produced for example by injury, trauma or tumours, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, thygeson keratitis, progressive mooren's ulcer, an ocular inflammatory disease caused by bacterial or viral infection, and by an ophthalmic operation, an ocular inflammatory disease caused by a physical injury to the eye, a symptom caused by an ocular inflammatory disease including itching, flare, oedema and ulcer, erythema, erythema exsudativum multiforme, erythema nodosum, erythema annulare, scleroedema, dermatitis, angioneurotic oedema, laryngeal oedema, glottic oedema, subglottic laryngitis, bronchitis, rhinitis, pharyngitis, sinusitis, laryngitis or otitis media.

References herein to "back-of-eye diseases" include diseases affecting among other the retina, macular, fovea in the posterior region of the eye. Examples of suitable "back-of-eye diseases" include but are not limited to: macular oedema such as clinical macular oedema or angiographic cystoid macular oedema arising from various aetiologies such as diabetes, exudative macular degeneration and macular oedema arising from laser treatment of the retina, age-related macular degeneration, retinopathy of prematurity (also known as retrolental fibroplasia), retinal ischemia and choroidal neovascularization, retinal diseases (diabetic retinopathy, diabetic retinal oedema, retinal detachment, senile macular degeneration due to sub-retinal neovascularization, myopic retinopathy); inflammatory diseases; uveitis associated with neoplasms such as retinoblastoma or pseudoglioma; neovascularization following vitrectomy; vascular diseases (retinal ischemia, choroidal vascular insufficiency, choroidal thrombosis, retinopathies resulting from carotid artery ischemia); and neovascularization of the optic nerve.

References herein to "front-of-eye diseases" refers to diseases affecting predominantly the tissues at the front-of-eye, such as the cornea, iris, ciliary body, conjunctiva etc. Examples of suitable "front-of-eye diseases" include but are not limited to: corneal neovascularization (due to inflammation, transplantation, developmental hypoplasia of the iris, corneal diseases or opacifications with an exudative or inflammatory component, neovascularization due to penetration of the eye or contusive ocular injury; chronic uveitis; anterior uveitis; inflammatory conditions resulting from surgeries such as LASIK, LASEK, refractive surgery, IOL implantation; irreversible corneal oedema as a complication of cataract surgery; oedema as a result of insult or trauma (physical, chemical, pharmacological, etc); inflammation; conjunctivitis (e.g. persistent allergic, giant papillary, seasonal intermittent allergic, perennial allergic, toxic, conjunctivitis caused by infection by bacteria, viruses or *Chlamydia*); keratoconjunctivitis (vernal, atopic, sicca); iridocyclitis; iritis; scleritis; episcleritis; infectious keratitis; superficial punctuate keratitis; keratoconus; posterior polymorphous dystrophy; Fuch's dystrophies (corneal and endothelial); aphakic and pseudophakic bullous keratopathy; corneal oedema; scleral disease; ocular cicatrcial pemphigoid; pars planitis; Posner Schlossman syndrome; Behcet's disease; Vogt-Koyanagi-Harada syndrome; hypersensitivity reactions; ocular surface disorders; conjunctival oedema; toxoplasmosis chorioretinitis; inflammatory pseudotumor of the orbit; chemosis; conjunctival venous congestion; periorbital cellulitis; acute dacryocystitis; non-specific vasculitis; sarcoidosis; and cytomegalovirus infection.

Examples of suitable "disorders associated with excessive vascular permeability and/or edema in the eye", e.g. in the retina or vitreous, include, but are not limited to, age-related macular degeneration (AMD), retinal edema, retinal hemorrhage, vitreous hemorrhage, macular edema (ME), diabetic macular edema (DME), proliferative diabetic retinopathy (PDR) and non-proliferative diabetic retinopathy (DR), radiation retinopathy, telangiectasis, central serous retinopathy, and retinal vein occlusions. Retinal edema is the accumulation of fluid in the intraretinal space. DME is the result of retinal microvascular changes that occur in patients with diabetes. This compromise of the blood-retinal barrier leads to the leakage of plasma constituents into the surrounding retina, resulting in retinal edema. Other disorders of the retina include retinal vein occlusions (e.g. branch or central vein occlusions), radiation retinopathy, sickle cell retinopathy, retinopathy of prematurity, Von Hippie Lindau disease, posterior uveitis, chronic retinal detachment, Irvine Gass Syndrome, Eals disease, retinitis, and/or choroiditis.

(D) Mutation of Polypeptides

The desired diversity is typically generated by varying the selected molecule at one or more positions. The positions to be changed are selected, such that libraries are constructed for each individual position in the loop sequences. Where appropriate, one or more positions may be omitted from the selection procedure, for instance if it becomes apparent that those positions are not available for mutation without loss of activity.

The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The same techniques could be used in the context of the present invention. For example, the H3 region of a human tetanus toxoid-binding Fab has been randomised to create a range of new binding specificities (Barbas et al. (1992) Proc. Natl. Acad. Sci. USA, 89: 4457). Random or semi-random H3 and L3 regions have been appended to germ line V gene segments to produce large libraries with mutated framework regions (Hoogenboom- & Winter (1992) R Mol. Biol., 227: 381; Barbas et al. (1992) Proc. Natl. Acad. Sci. USA, 89: 4457; Nissim et al. (1994) EMBO J, 13: 692; Griffiths et al. (1994) EMBO J, 13: 3245; De Kruif et al. (1995) J. Mol. Biol., 248: 97). Such diversification has been extended to include some or all of the other antigen binding loops (Crameri et al. (1996) Nature Med., 2: 100; Riechmann et al. (1995) BiolTechnology, 13: 475; Morphosys, WO97/08320, supra).

However, since the polypeptides used in the present invention are much smaller than antibodies, the preferred method is to synthesise mutant polypeptides de novo. Mutagenesis of structured polypeptides is described above, in connection with library construction.

The invention is further described below with reference to the following examples.

EXAMPLES

Materials and Methods
Cloning of Phage Libraries

Phage libraries were generated according to Heinis et al., *Nat Chem Biol* 2009, 5 (7), 502-7). In Heinis et al, the genes encoding a semi-random peptide with the sequence Xaa-Cys-(Xaa)$_3$-Cys-(Xaa)$_3$- (SEQ ID NO: 216), the linker Gly-Gly-Ser-Gly (SEQ ID NO: 11) and the two disulfide-free domains D1 and D2 (Kather, et al., *J Mol Biol* 2005, 354 (3), 666-78) were cloned in the correct orientation into the phage vector fd0D12 to obtain 'library 3×3'. The genes encoding the peptide repertoire and the two gene 3 domains were step-wise created in two consecutive PCR reactions. First, the genes of D1 and D2 were PCR amplified with the two primer prepcr (5'-GGCGGTTCTGGCGCTGAAACTGTT-GAAAGTAG-3') (SEQ ID NO: 12) and sfi2fo

```
                                        (SEQ ID NO: 13)
(5'-GAAGCCATGGCCCCCGAGGCCCCGGACGGAGCATTGACAGG-3';
``` restriction site is underlined) using the vector fdg3p0ss21 (Kather, et al., *J Mol Biol* 2005, 354 (3), 666-78) as a template. Second, the DNA encoding the random peptides was appended in a PCR reaction using the primer sficx3ba:

```
                                        (SEQ ID NO: 14)
5'-TATGCGGCCCAGCCGGCCATGGCANNKTGTNNKNNKNNKTGCNNKNNK

NNKNNKTGTNNKGGGCGGTTCTGGCGCTG-3'
```

(restriction site is underlined), and sfi2fo. The ligation of 55 and 11 μg of SfiI-digested fd0D12 plasmid and PCR product yielded 5.6×10$^8$ colonies on 10 20×20 cm chloramphenicol (30 μg/ml) 2YT plates. Colonies were scraped off the plates with 2YT media, supplemented with 15% glycerol and stored at −80° C. Construction of the libraries described herein employed the same technique to generate the semi-random peptide Pro-Ala-Met-Ala-Cys-(Xaa)$_3$-Cys-(Xaa)$_3$-Cys (SEQ ID NO: 15) for a 3×3 library for example, and therefore replaced the sficx3ba primer sequence with:

```
                                        (SEQ ID NO: 16)
5'-TATGCGGCCCAGCCGGCCATGGCATGTNNKNNKNNKTGCNNKNNKNNK

KTGTGGCGGTTCTGGCGCTG-3'.
```

Libraries with other loop lengths were generated following the same methodology.

Phage Selections

Glycerol stocks of phage libraries were diluted to $OD_{600}$=0.1 in 500 ml 2YT/chloramphenicol (30 μg/ml) cultures and phage were produced at 30° C. over night (15-16 hrs). Phage were purified and chemically modified as described in Heinis, et al., Nat Chem Biol 2009, 5 (7), 502-7 Biotinylated hPK (3 μg) (IHPKA, from human plasma, Innovative Research, Novi, Mich., USA) was incubated with 50 μl pre-washed magnetic streptavidin beads (Dynal, M-280 from Invitrogen, Paisley, UK) for 10 minutes at RT. Beads were washed 3 times prior to blocking with 0.5 ml washing buffer (10 mM Tris-Cl, pH 7.4, 150 mM NaCl, 10 mM $MgCl_2$, 1 mM $CaCl_2$) containing 1% BSA and 0.1% Tween 20 for 30 minutes at RT with rotation. Chemically modified phage (typically 10$^{10}$-10$^{11}$ t.u. dissolved in 2 ml washing buffer) were concomitantly blocked by addition of 1 ml washing buffer containing 3% BSA and 0.3% Tween 20. Blocked beads were then mixed with the blocked chemically modified phage and incubated for 30 minutes on a rotating wheel at RT. Beads were washed 8 times with washing buffer containing 0.1% Tween 20 and twice with washing buffer before incubation with 100 μl of 50 mM glycine, pH 2.2 for 5 minutes. Eluted phage were transferred to 50 μl of 1 M Tris-Cl, pH 8 for neutralization, incubated with 30 ml TG1 cells at $OD_{600}$=0.4 for 90 minutes at 37° C. and the cells were plated on large 2YT/chloramphenicol plates. One or two additional rounds of panning were performed using the same procedures. In the second round of selection, neutravidin-coated magnetic beads were used to prevent the enrichment of streptavidin-specific peptides. The neutravidin beads were prepared by reacting 0.8 mg neutravidin (Pierce, Rockford, Ill., USA) with 0.5 ml tosyl-activated magnetic beads (Dynal, M-280 from Invitrogen, Paisley, UK) according to the supplier's instructions.

Cloning and Expression of Human, Monkey and Rat PK

The catalytic domain of human, monkey and rat PK was expressed in mammalian cells as an inactive precursor having a pro-peptide connected N-terminally via a proTEV cleavage site to the catalytic domain. The expression vector was cloned and the protein expressed, activated and purified as described as follows. Synthetic genes coding for a PK signal sequence, a polyhistidine tag, a proTEV cleavage site, mature catalytic domain of PK and a stop codon were purchased from Geneart (Regensburg, Germany) (Supplementary materials). Plasmid DNA containing the synthetic genes for human, monkey (*Macaca mulatta*) and rat PK was prepared and the gene transferred into the pEXPR-IBA42 mammalian expression vector (IBA Biotechnology, Göttingen, Germany) using the restriction enzyme pair XhoI and HindIII (Fermentas, Vilnius, Latvia) and T4 DNA ligase (Fermentas). The ligated plasmids were transformed into XL-1 blue electrocompetent cells (Stratagene, Santa Clara, USA) and plated onto 2YT agar plates containing ampicillin (10 μg/ml). DNA from the three expression vectors (termed mPK, rPK and hPK) was produced and the correct sequences confirmed by DNA sequencing (Macrogen, Seoul, South Korea).

The three orthologous plasma Kallikreins were expressed in mammalian cells as follows. 50 ml of suspension-adapted HEK-293 cells were grown in serum-free ExCell 293 medium (SAFC Biosciences, St. Louis, Mo.) in the presence of 4 mM glutamine and the histone deacetylase inhibitor valproic acid (3.75 mM) in an orbitally shaken 100 ml flask at 180 rpm in an ISF-4-W incubator (Kühner AG, Birsfelden, Switzerland) at 37° C. in the presence of 5% $CO_2$. The embryonic kidney (HEK-293) cells at high cell density (20×10$^6$ cells/ml) (Backliwal, et al/. *Biotechnol Bioeng* 2008, 99 (3), 721-7) were transfected with the three plasmids (300 μg/ml) using linear polyethylenimine (PEI, Polysciences, Eppenheim, Germany). At the end of the 7-day production phase, cells were harvested by centrifugation at 2'500 rpm for 15 min at 4° C. Any additional cell debris was removed from the medium by filtration through 0.45 μm PES membranes (Filter-top 250 ml low protein binding TPP). The polyhistidine-tagged protein was purified by Ni-affinity chromatography using Ni-NTA resin, washing buffer (500 mM NaCl, 25 mM $Na_2HPO_4$, pH7.4) and elution buffer (500 mM NaCl, 25 mM Na$_2$HPO$_4$, pH 7.4, 500 mM imidazole). The protein was partially activated with (50 units) proTEV (Promega, Madison, Wis., USA) and additionally purified by Ni-affinity chromatography and gel filtration (PD10 column, 150 mM NaCl, 0.5 mM EDTA, 50 mM HEPES, pH 7).

Development of Polypeptides with Improved Binding Activity

Randomisation of Individual Positions

Library construction: In order to map the amino-acids in the Kallikrein binding bicyclic peptides a set of small libraries was constructed. For a bicycle comprised of 2 loops of 5 residues, 10 separate libraries were generated each with randomisation at a particular codon in the peptide sequence. Oligonucleotides were designed for each library in order to mutate the phage genome DNA by site-directed mutagenesis. The mutagenesis incorporated randomisation of the codon of interest (change to NNS), and removal of a unique ApaL1 restriction site from the template genome sequence. The mutagenesis product was purified using QIAgen QIAquick PCR purification kit with elution into ultrapure water. Each library was used to separately transform TG1 E coli by electroporation with a BioRad Micropulser machine (Ec1 program) and 1 mm BioRad cuvette. After 1 hour recovery at 37 C in 1 ml SOC media, the library transformants were grown overnight in 25 ml 2TY broth containing antibiotic to selectively grow library transformants only. The bacteria were harvested by centrifugation and the library phage DNA was purified from the E coli using a QIAgen Plasmid Plus Midi kit and eluted in distilled water. The purified DNA was digested with ApaL1 for 2 hours in New England Biolabs buffer 4 to remove the parent material. After digestion, the DNA was repurified using QIAgen PCR purification kit (as above) and used to transform TG1 (electroporation; as described above). Following the 1 hour recovery in SOC, transformants were plated on LB-agar plates containing selective antibiotic and colonies allowed to grow overnight at 37 C.

Assay of binding of individual clones: Library transformant colonies were picked at random and grown as individual cultures in 2TY broth containing selective antibiotic. The picked colonies were DNA-sequenced using a QIAgen PyroM ark Q96 DNA sequencer to reveal the amino-acid substitution present in each clone. Where isolated, a clone of each unique substitution was assayed for human plasma Kallikrein binding as follows. The phage-containing supernatant was harvested from the culture and phage were cyclised with tris bromomethyl benzene (TBMB) based on the methods of Heinis et al (Nature Chemical Biology vol. 5 pp 502-507 (2009)). The purified phage from this process were assayed for binding to biotinylated human plasma Kallikrein using a homogeneous plate-based binding assay; assay read-out measured on a BMG Labtech Pherastar FS plate reader. The quantitative binding data from triplicate assay samples was averaged (mean) and expressed as signal:background (where background was a sample assayed with no target material). The signal:background was expressed as a % of the parallel parent sample. Error bars denote standard deviation of the mean. Assays shown are representative of at least 2 independent experiments. The assay data was correlated with the peptide sequences. Substitutions marked in grey were not tested (a clone was not isolated from the random library sampling). A sample of a non-binding (arbitrary) bicycle was assayed in parallel to illustrate the assay baseline.

Randomisation of Peptide Domains

Library construction: Small phage libraries were generated according to the methods of Heinis et al as described in 'Cloning of phage libraries' above. The sficx3ba primer was modified such that the bicycle-encoding portion was based on a parent 5×5 bicycle (5×5: two 5-residue loops) DNA sequence with only 4-6 codons randomized to NNS. The randomized codons were those encoding the peptide domain/motif of interest.

Assay of binding of individual clones: Library transformant colonies, or selection output colonies, were picked and grown as individual cultures in 2TY broth containing selective antibiotic. The picked colonies were DNA-sequenced using a QIAgen PyroMark Q96 DNA sequencer to reveal the amino-acid substitution present in each clone, and were assayed for human plasma Kallikrein binding as follows. The phage-containing supernatant was harvested from the culture and phage were cyclised with tris bromomethyl benzene (TBMB) based on the methods of Heinis et al (Nature Chemical Biology vol. 5 pp 502-507 (2009)). The purified phage from this process were assayed for binding to biotinylated human plasma Kallikrein using a homogeneous plate-based binding assay; assay read-out measured on a BMG Labtech Pherastar FS plate reader. The quantitative binding data from duplicate assay samples was averaged (mean) and expressed as signal:background. Assay data shown is representative of at least 2 independent experiments. The assay data was correlated with the peptide sequences.

Synthesis and Purification of Bicyclic Peptides

Peptide sequences are shown in Tables 4 to 6. The core peptide sequences were Ac-$\underline{C_1}$S$_1$W$_2$P3A$_4$R$_5$$\underline{C_2}$L$_6$H$_7$Q$_8$D$_9$L$_{10}$$\underline{C_3}$—NH$_2$ (SEQ ID NO: 7) (denoted as Ac-(06-34-18)(TMB)- NH2) and Ac-$\underline{C_1}$S$_1$F$_2$P$_3$Y$_4$R$_5$$\underline{C_2}$L$_6$H$_7$Q$_8$D$_9$L$_{10}$$\underline{C_3}$—NH$_2$ (SEQ ID NO: 8) (denoted as Ac-(06-34- 18)(TMB)-NH2 Phe2 Tyr4).

Peptide synthesis was based on Fmoc chemistry, using a Symphony peptide synthesiser manufactured by Peptide Instruments. Standard Fmoc-amino acids were employed (Sigma, Merck), with the following side chain protecting groups: Arg(Pbf); Asn(Trt); Asp(OtBu); Cys(Trt); Glu(OtBu); Gln(Trt); His(Trt); Lys(Boc); Ser(tBu); Thr(tBu); Trp(Boc), Tyr(tBu) (Sigma). The coupling reagent was HCTU (Pepceuticals), diisopropylethylamine (DIPEA, Sigma) was employed as a base, and deprotection was achieved with 20% piperidine in DMF (AGTC). Syntheses were performed at 100 umole scale using 0.37 mmole/gr Fmoc-Rink amide AM resin (AGTC), Fmoc-amino acids were utilised at a four-fold excess, and base was at a four-fold excess with respect to the amino acids. Amino acids were dissolved at 0.2 M in DMF, HCTU at 0.4 M in DMF, and DIPEA at 1.6 M in N-methylpyrrolidone (Alfa Aesar). Coupling times were generally 30 minutes, and deprotection times 2×2.5 minutes. Fmoc-N-methylglycine (Fmoc-Sar-OH, Merck) was coupled for 1 hr, and deprotection and coupling times for the following residue were 20 min and 1 hr, respectively. After synthesis, the resin was washed with dichloromethane, and dried. Cleavage of side-chain protecting groups and from the support was effected using 10 mL of 95:2.5:2.5:2.5 v/v/v/w TFA/H$_2$O/iPr3SiH/dithiothreitol for 3 hours. Following cleavage, the spent resin was removed by filtration, and the filtrate was added to 35 mL of diethylether that had been cooled at −80 deg C. Peptide pellet was centrifuged, the etheric supernatant discarded, and the peptide pellet washed with cold ether two more times. Peptides were then resolubilised in 5-10 mL acetonitrile-water and lyophilised. A small sample was removed for analysis of purity of the crude product by mass spectrometry (MALDI-TOF, Voyager DE from Applied Biosystems). Following lyophilisation, peptide powders were taken up in 10 mL 6 M guanidinium hydrochloride in $H_2O$, supplemented with 0.5 mL of 1 M dithiothreitrol, and loaded onto a C8 Luna preparative HPLC column (Phenomenex). Solvents ($H_2O$, acetonitrile) were acidified with 0.1% heptafluorobutyric acid. The gradient ranged from 30-70% acetonitrile in 15 minutes, at a flowrate of 15/20 mL/min, using a Gilson preparative HPLC system. Fractions containing pure linear peptide material (as identified by MALDI) were combined, and modified with trisbromomethylbenzene (TBMB, Sigma). For this, linear peptide was diluted with $H_2O$ up to ~35 mL, ~500 uL of 100 mM TBMB in acetonitrile was added, and the reaction was initiated with 5 mL of 1 M NH4HCO3 in $H_2O$ (pH 8). The reaction was allowed to proceed for ~30-60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20 deg C. for storage.

Non-natural amino acids were acquired from the sources set forth in Table 7.

Bulky or hindered amino acids (NMe-Ser, NMe-Trp, NorHar, 4PhenylPro, Agb, Agp, NMe-Arg, Pen, Tic, Aib, Hyp, NMe-Ala, NMe-Cys, 4,4-BPAl, 3,3-DPA, Dpg, 1NAl, 2NAl, Aze, 4BenzylPro, Ind) were usually coupled for 1 hours (20 min deprotection), and 6 hrs for the residue that followed (20 min deprotection). HCTU was used as a coupling reagent as before. Scale was usually at 50 umole.

Synthesis of Peptoids, Reduced Amide Bonds and α-N-Methylated Peptides

Peptoids (i.e. N-His7) were synthesised according to the scheme developed by Zuckermann et al. (Ronald N. Zuckermann, Janice M. Kerr, Stephen B. H. Kent, Walter H. Moos, Efficient method for the preparation of peptoids [oligo(N-substituted glycines)] by submonomer solid-phase synthesis Journal of the American Chemical Society, (1992), 114(26), 10646-10647).

Reduced amide pseudo peptide bonds were synthesised according to the scheme in Sasaki Y, Coy D H., Solid phase synthesis of peptides containing the CH2NH peptide bond isostere, Peptides. 1987 January-February; 8(1):119-21.

N-methylated peptides (NMe-His, NMe-Gln) were synthesised using a modified form of the Mitsunobu reaction, according to a scheme described in Nature Protocols, "Synthesis of N-methylated cyclic peptides", by Chatterjee et al, 7(3) 2012, pp 432. All other N-methylated amino acids (NMe-Leu, NMe-Asp) were obtained as Fmoc precursors from commercial sources.

Enzyme Assays

Functional enzyme assays were conducted in 10 mM Tris HCl, 150 mM NaCl, 10 mM MgCl2, 1 mM $CaCl_2$) and 1 mg/mL BSA (all Sigma UK) pH7.4 at 25° C. in solid black 96 well plates. Briefly 26.5 pM human plasma Kallikrein (purchased from Stratech, UK) or 500 pM rat plasma Kallikrein (expressed and purified in house) were incubated in the absence or presence of increasing concentrations of test peptide for 15 minutes before addition of the fluorogenic substrate Z-PheArg-AMC (Enzo Lifesciences UK) to a final assay concentration of 100 μM in 4% DMSO. Release of AMC was measured using a Pherastar FS (BMG Labtech), excitation 360 nm, emission 460 nm. The rate of the linear phase of the reaction, typically 5 to 45 minutes, was calculated in MARS data analysis software (BMG labtech). The rate was then used to calculate the IC50 and Ki in Prism (GraphPad). A four parameter inhibition non-linear regression equation was used to calculate the IC50. The One site—fit Ki equation used to calculate the Ki, constraining the Ki to the Km for the substrate which is 150 μM. All Ki/IC50 values are the mean of at least two independent experiments, and at least three for peptides with Ki values lower than 1 nM.

Peptides were dissolved as the TFA-salts in their powder form, and stock solutions were usually prepared in water. All solutions were centrifuged and filtered (20 μm syringe filters) prior absorption measurement at 280 nm. Extinction coefficients were calculated based on the Trp/Tyr content of the peptide, and that of TMB (the TMB core, when contained in a peptide, has an ε of ~300 $M^{-1}$ $cm^{-1}$). For peptides containing non-natural amino acids with suspected chromophoric properties (i.e. NorHar, 4PhenylPro, 3Pal, 4Pal, Tic, 4GuanPhe, 4,4-BPAl, 3,3-DPA, 1NAl, 2NAl, 4Benzyl-Pro, Ind) concentrations were determined by weighing the powder and dissolving the peptide in a defined quantity of water. These were prepared independently, twice, for peptides with a Ki to Kallikrein at 1 nM or less.

Plasma Stability Profiling

Three methods were employed to assess the stability of bicycles (peptides conjugated to molecular scaffolds) in plasma.

Method #1:

A rapid plasma stability profiling assay was developed that employed mass spectrometric detection (MALDI-TOF, Voyager DE, Applied Biosystems) of the parent mass, until the time when the parent peptide mass was no longer observable. Specifically, 200 uM of peptide was incubated in the presence of 35% rat or human plasma (Sera labs, using citrate as anticoagulant) at 37 deg C., which was supplemented with 1×PBS (derived from a 10×PBS Stock, Sigma). At various time points (i.e. t=0, 3, 24 hrs, henceafter daily up to 10 days), 2 uL of sample was added to 18 uL of 30 mM ammonium bicarbonate in a 1:1 mixture of acetonitrile:$H_2O$. Samples were frozen at −80 deg C. until the time of analysis. For mass spectrometric analysis that determines the approximate detection window of the peptide, the acetonitrile:$H_2O$-diluted sample of a given time point was spotted directly (0.7 uL) onto the MALDI plate. Matrix (alpha-cyanocinnamic acid, Sigma, prepared as a saturated solution in 1:1 acetonitrile:water containing 0.1% trifluoroacetic acid) was layered over the sample (1 uL). At a similar laser intensity setting on the MALDI TOF, the time could then be determined until parent peptide was no longer detectable. It should be noted that this is a qualitative assay serves to detect relative changes in plasma stability.

Method #2:

To obtain stability data more rapidly, peptides were also assessed in 95% plasma. Here, PBS was omitted, and a 1 mM peptide stock (in DMSO) was directly diluted into plasma (i.e. 2.5 uL stock into 47.5 uL plasma), giving a final concentration of 50 uM. 5 uL samples were taken at appropriate time points and frozen at −80 deg C. For analysis, the samples were defrosted, mixed with 15 uL of 1:1 acetonitrile:methanol, and centrifuged at 13 k for 5 min. 5 uL of the peptide-containing supernatant was aspirated and mixed with 30 mM ammonium bicarbonate in a 1:1 mixture of acetonitrile:$H_2O$. 1 uL of this was then spotted on the MALDI plate and analysed as described above. As above, it should be noted that this is a qualitative assay serves to detect relative changes in plasma stability.

Method #3:

To obtain plasma stability quantitatively, peptide stock solutions (1 mM in DMSO) were shipped to Biofocus, UK, who performed the analysis. Peptides were diluted to 100 uM with water, and diluted 1:20 in plasma (5 uM final concentration, with the plasma at 95%), sampled as appropriate, precipitated as above, and quantified using a Waters Xevo TQ-MS.

Example 1: Identification of Preferred Residues for Binding Activity

From the examples of 5×5 peptides shown in Table 4 it is possible to identify amino acids that are conserved between peptides with binding activity. To determine which residues were preferred for binding activity, representatives from two of the identified families of peptides were studied further. These were peptides 06-34, which comprises a CXWPARC (SEQ ID NO: 17) motif in the first loop of the bicycle, and peptide 06-56, which comprises a CGGxxNCR (SEQ ID NO: 18) motif across both loops of the bicycle. For each peptide sequence, a set of 10 phage libraries was created in which 9 of the loop residues were kept constant and the other residue was randomised so that any amino-acid could be expressed in the library at that position. (See 'Randomisation of individual positions—Library construction' in Methods above.) For each library a set of 20 randomly selected phage clones were screened for binding to human Kallikrein in a phage binding assay to identify the critical residues for target binding. (See 'Randomisation of individual positions—Assay of binding of individual clones' in Methods above.) The data from this experiment are shown in FIGS. 4-6.

For peptide 06-34 (FIG. 4), it is clear that Arg1 of the bicycle can be replaced with a variety of different amino-acids and binding to human plasma Kallikrein is retained or enhanced. By contrast, replacement of residues 2, 3, 4, 5 (Trp2, Pro3, Ala4, Arg5) by most amino acids greatly reduced the signal seen in an assay that was set up with a stringent cut-off for high affinity binders. Val6 can be replaced by many different amino-acids and binding activity is retained or enhanced. Replacement of other residues in the second loop indicated that only Leu10 could be replaced by a variety of different amino-acids whilst retaining activity. Positions 7, 8, and 9 have limited capacity for substitution and no substitutions were identified that enhanced binding.

For peptide 06-56 (FIGS. 5 and 6) it is clear that glycines at position 1 and 2 are the greatly preferred residues for binding to plasma Kallikrein as are arginine, tryptophan and threonine at positions 6, 8, and 9. Glutamine at position 4 and threonine at position 10 can be replaced by a variety of residues whilst retaining good binding activity. The three remaining residues—proline at position 1, asparagine at position 5 and threonine at position 7 have limited capacity for substitution.

Analysis of Amino-Acid Replacements

From the preceding analysis it is apparent that for 06-34, position one and position six can be replaced by a variety of amino-acids and still retain binding activity equal or greater than that of the parent peptide. To evaluate whether these observations would hold with isolated synthetic peptides, a set of peptides was designed according to the findings in FIG. 4, where Arg1 was replaced by a serine, and where Val6 was substituted by either threonine, methionine or leucine. Peptides employing the various combinations of these substitutions were also synthesised. These substitutions produced a greater binding signal in the assay (Table 5).

All of the variant synthetic peptides had approximately equivalent or enhanced activity against human plasma Kallikrein in enzyme inhibition assays compared to the 06-34 parent peptide, indicating that this type of analysis could be used to fine-tune target binding affinities, and suggesting a route to identifying lead peptide candidates of very high potencies.

The peptides were also tested against rat plasma Kallikrein in isolated enzyme assays. Substitution of Arg1 to Ser1 had a marginal impact on activity against rat Kallikrein, whereas substitutions of Val6 to threonine, methionine or leucine generated peptides with markedly increased potency against rat plasma Kallikrein. Activity to human Kallikrein was fully retained. Thus, by determining positions amenable to substitutions, peptides with desirable properties, such as target orthologue cross-reactivity, can be identified.

To demonstrate the possibility of replacing these two positions with non-natural amino acids so as to have the capacity to introduce functionalities or properties that are not present in the parent peptide, Arg1 and Val6 in 06-34-03 were replaced with either alanine or N-methylglycine (sarcosine), or with N-methyl serine on position 1, and evaluated for binding. Remarkably, as shown in Table 6, positions 1/6 are amenable to removal of the side chain altogether, as the R1A/V6A (06-34-03 Ala1,6) peptides retained full potency compared to the parent. Replacement of residues 1,6 with N-methylglycine (06-34-03 NMeGly1,6) caused a reduction in potency, however the binding affinity remained in the low nanomolar range. Introduction of an N-methyl-serine at position 1 causes a ten-fold loss in potency, but binding remains in the picomolar range. Thus, certain positions in the bicycle can be identified that allow changes in the peptide backbone structure or side chains, which could allow for deliberate enhancement of protease stability, enhanced solubility, reduced aggregation potential, and introduction of orthologous functional groups.

Example 2: Detailed Analysis of WPAR Domain

The WPAR (SEQ ID NO: 19) motif identified from Example 1 was analysed in the context of the 06-34-03 peptide, in order to identify alternatives or improvements to the WPAR motif. A library was constructed where positions 1, 6, 7, 8, 9 &10 of 06-34-03 were fixed and positions 2, 3, 4 & 5 were randomised (see 'Randomisation of peptide domains—Library construction' in Methods above). Selections against human plasma Kallikrein were performed at a variety of stringencies (see Phage selections' in Methods above). All output sequences were identified and analysed for target binding (see 'Randomisation of peptide domains—Assay of binding of individual clones' in Methods above). Table 17 lists each unique sequence, its relative abundance in the selection output (frequency), and a rank number according to target binding strength.

Table 17 shows that WPAR (SEQ ID NO: 19) motif confers the best binding to human plasma Kallikrein, although other Kallikrein binding sequences are retrieved from selections in high abundance. These include, but are not restricted to: WPSR (SEQ ID NO: 20), WPAR (SEQ ID NO: 19), WSAR (SEQ ID NO: 21), WPFR (SEQ ID NO: 22), WPYR (SEQ ID NO: 23), FPFR (SEQ ID NO: 24), & FPFR (SEQ ID NO: 24). The most effective and abundant motifs at positions 2, 3, 4 & 5 can be summarised as: w/F PxK/R Table 18(A) shows that WPAR (SEQ ID NO: 19) & WPSR (SEQ ID NO: 20) were most abundant in the more stringent selection outputs; FPFR (SEQ ID NO: 24) & FPYR (SEQ ID NO: 25) were abundant in the lower stringency selection outputs. This would indicate that WPAR-like sequences are stronger binders than FPFR-like sequences. Analysis of each motif (within the 06-34-03 context) in the target binding assay (FIG. 24), reveals that WPAR (SEQ ID NO: 19) at positions 2, 3, 4 & 5 of the 06-34-03 sequence is the optimal sequence for Kallikrein binding.

Example 3: Optimisation of the Sequence Outside the WPAR Pharmacophore

Figure 1:
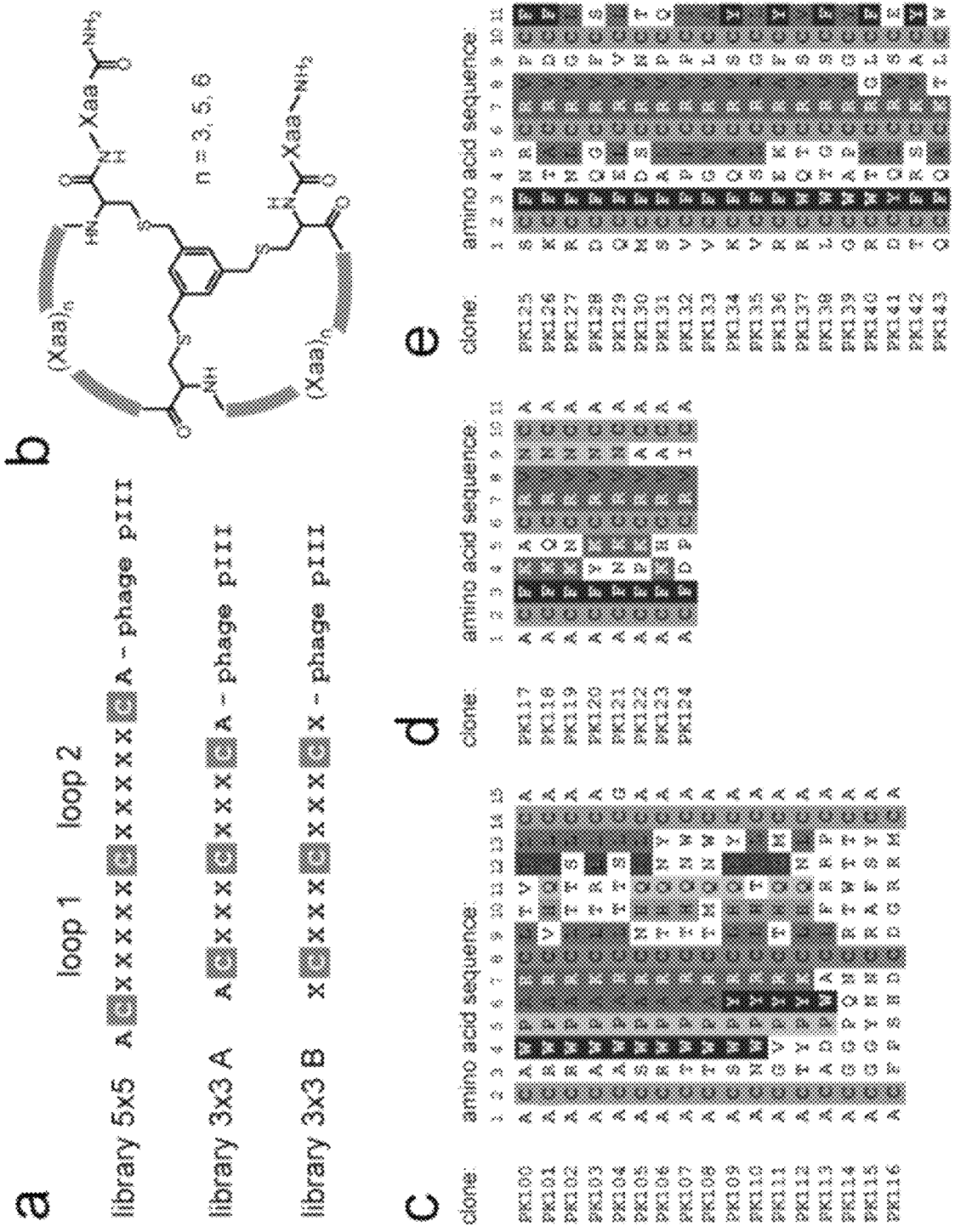
FIG. 1 Phage selection of bicyclic peptides. (a) Bicyclic peptide phage libraries. Random amino acids are indicated as 'X', alanine as 'A' and the constant three cysteine residues as 'C'. (b) Format of chemically synthesized bicyclic peptide structures having loops of 3, 5 or 6 amino acids. The structures are generated by linking linear peptides via three cysteine side chains to tris-(bromomethly)benzene (TBMB). Amino acids that vary in the bicyclic peptides are indicated with 'Xaa'. (c-e) Sequences of bicyclic peptides isolated from library 5×5 (c), library 3×3 A (d) and library 3×3 B (e). Similarities in amino acids are highlighted by shading. ACXXXCXXXCA (SEQ ID NO: 177); ACXXXCXXXCA (SEQ ID NO: 178); XCXXXCXXXCX (SEQ ID NO: 216); PK100 (SEQ ID NO: 33); PK101 (SEQ ID NO: 34); PK102 (SEQ ID NO: 36); PK103 (SEQ ID NO: 48); PK104 (SEQ ID NO: 46); PK105 (SEQ ID NO: 35); PK106 (SEQ ID NO: 37); PK107 (SEQ ID NO: 38); PK108 (SEQ ID NO: 44). PK 109 (SEQ ID NO: 42); PK110 (SEQ ID NO: 41); PK111 (SEQ ID NO: 43); PK112 (SEQ ID NO: 47); PK113 (SEQ ID NO: 45); PK114 (SEQ ID NO: 40); PK115 (SEQ ID NO: 49); PK116 (SEQ ID NO: 39); PK117 (SEQ ID NO: 209); PK118 (SEQ ID NO: 207); PK119 (SEQ ID NO: 205); PK120 (SEQ ID NO: 208); PK121 (SEQ ID NO: 206)

The WPAR (SEQ ID NO: 19) motif and its variants have been studied within the context of peptide 06-34-03. FIG. 1 demonstrates that some positions outside of the WPAR (SEQ ID NO: 19) motif can maintain Kallikrein binding when substituted for other residues. In order to study the non-WPAR determinants of Kallikrein binding, a phage library was generated with a fixed-WPAR sequence and all other positions randomised (CxWPARCxxxxxC) (SEQ ID NO: 26) as described in 'Randomisation of peptide domains—Library construction' in Methods above.

80 random library members were isolated directly from the library pool (no selection) and assayed for binding to Kallikrein at both high and low stringency (see 'Randomisation of peptide domains—Assay of binding of individual clones' in Methods above). These library members, which contain random sequences outside the WPAR, showed little or no binding to human plasma Kallikrein (data not shown), indicating that the presence of a WPAR motif alone is not sufficient to retain measurable Kallikrein binding: the rest of the bicycle sequence must also contribute or influence the interaction.

Selections against human plasma Kallikrein were performed with this library in order to study the non-WPAR determinants of Kallikrein binding, and to isolate the optimal WPAR-containing peptide sequence. Over 150 selection output sequences were isolated and screened for binding to human plasma Kallikrein (as described in Methods above). The sequences were ranked in order of Kallikrein binding and the top 50 sequences were aligned in Table 19. Table 19 shows that the residue at position 1 does not affect Kallikrein binding, but a strong consensus for Histidine is seen at position 7 (which supports findings in Example 1 above). The peptide 06-34-03—derived from the work in Example 1—is one of the best sequences. The composition of the second loop shows clear trends which confer strong Kallikrein binding when with a WPAR motif.

The best WPAR-containing binders to human plasma Kallikrein have the trend:

(SEQ ID NO: 27)
C X W P A R C $^T/_L$ H $^Q/_T$ D L C

H7, D9 and L10 are heavily conserved in WPAR-containing Kallikrein binding sequences.

Two motifs in within the second bicycle loop (positions 6-10) were identified:

1.
(SEQ ID NO: 28)
C X W P A R C T H $^Q/_T$ D L C (positions 6, 7 & 10: "THxxL" (SEQ ID NO: 219))

2.
(SEQ ID NO: 218)
C X W P A R C $^T/_L$ H $^Q/_T$ D L C (positions 7, 8, & 10: "xHxDL" (SEQ ID NO: 220))

Over 120 identified human plasma Kallikrein binders (selection output sequences) were grouped 2 different ways, according to their derivation from motifs "THxxL" (SEQ ID NO: 219) or "xHxDL" (SEQ ID NO: 220). For all groups, the average Kallikrein binding assay signal for output sequences was noted as a measure of Kallikrein binding for a given group (Table 20).

The Kallikrein binding assay data shown in Table 20 demonstrates that 'THxxL' (SEQ ID NO: 219) and 'xHxDL' (SEQ ID NO: 220) motifs result in the best Kallikrein binding when in a bicyclic peptide with a WPAR motif. The combination of the 2 motifs, 'THxDL' (SEQ ID NO: 29), gives the highest binding to human plasma Kallikrein and includes the 'THQDL' (SEQ ID NO: 30) second loop sequence of the 06-34-03 peptide.

Example 4: Systematic Analysis of Plasma Stability

For a Kallikrein-inhibiting bicycle, it is pertinent to obtain an adequate protease stability profile, such that it has a low protease-driven clearance in plasma or other relevant environments. In a rapid comparative plasma stability assay (methods section, method #1) that observed the progressive disappearance of parent peptide in rat plasma, it was found that the N-terminal alanine (which is present at the time of selections and was originally included in synthetic peptides of lead sequences) is rapidly removed across all bicycle sequences tested by both rat and human plasma. This degradation was avoided by synthesising a lead candidate lacking both N- and C-terminal alanines. To remove potential recognition points for amino- and carboxypeptidases, the free amino-terminus that now resides on Cys 1 of the lead candidate is capped with acetic anhydride during peptide synthesis, leading to a molecule that is N-terminally acetylated. In an equal measure, the C-terminal cysteine is synthesised as the amide so as to remove a potential recognition point for carboxypeptidasese. Thus, bicyclic lead candidates have the following generic sequence: Ac-C$_1$AA$_1$AA$_2$AA$_n$C$_2$AA$_{n+1}$AA$_{n+2}$AA$_{n+3}$C$_3$(TMB)-NH2, where "Ac" refers to N-terminal acetylation, "—NH2" refers to C-terminal amidation, where "C$_1$, C$_2$, C$_3$" refers to the first, second and third cysteine in the sequence, where "AA$_1$" to "AA$_n$" refers to the position of the amino acid (whose nature "AA" is defined by the selections described above), and where "(TMB)" indicates that the peptide sequence has been cyclised with TBMB or any other suitable reactive scaffold.

Due to the high affinity of Ac-06-34-18(TMB)-NH2 to both human (Ki=0.17 nM) and rat Kallikrein (IC50=1.7 nM), we chose this Bicycle for lead development (FIG. 9, Table 1, Tabe 5). Using the same rapid plasma stability profiling assay described above, Ac-06-34-18(TMB)-NH2 had an observability window of about 2 days (methods section, method #1), which equates to a rat plasma half-life of ~2 hrs (as determined quantitatively by LC/MS, see below, table 23, method #3).

In an effort to identify the proteolytic recognition site(s) in Ac-06-34-18(TMB)-NH2, the peptide was sampled in 35% rat plasma over time (method #1), and each sample was analysed for the progressive appearance of peptide fragments using MALDI-TOF mass spectrometry. The parent mass of Ac-06-34-18(TMB)-NH2 is 1687 Da. Over time (FIG. 7, 8), fragments appear of the masses 1548.6 (M1), 1194.5 (M2), and 1107.2 (M3). From the sequence of Ac-06-34-18(TMB)-NH2 (Ac-C$_1$S$_1$W$_2$P$_3$A$_4$R$_5$C$_2$L$_6$H$_7$Q$_8$D$_9$L$_{10}$C$_3$—NH2) (SEQ ID NO: 7), it can be calculated that the peak of M1 corresponds to Ac-06-34-18(TMB)-NH2 lacking Arg5 (—R5). This appears to be the initial proteolytic event, which is followed by removal of the 4-amino acid segment WPAR (SEQ ID NO: 19) in Ac-06-34-18(TMB)-NH2 (M2, -WPAR), and finally the entire first loop of Ac-06-34-18(TMB)-NH2 is excised (M3, -SWPAR) (FIG. 8). From this data, it is evident that Arg5 of Ac-06-34-18(TMB)-NH2 is the main rat plasma protease recognition site that is responsible the degradation of the Bicycle.

Alanine Substitutions and Scrambling of First Loop:

Having identified Arg5 in constituting the recognition site for rat plasma proteases, a campaign of chemical synthesis of Ac-06-34-18(TMB)-NH2 derivatives was undertaken with the aim of identifying candidates with higher plasma proteolytic stability. Crucially, such modifications should not affect the potency against human or rat Kallikrein. An initial exploration regarding the role of the WPAR (SEQ ID NO: 19) sequence/pharmacophore (FIG. 9, 10) was performed by replacing $W_2P_3$ with $A_2A_3$ or $A_2Q_3$ and by scrambling parts or the entire first loop of the bicycle. Table 8 below shows the sequences and the respective affinities against Kallikrein.

From these data it is clear that concomitant removal of $W_2P_3$ dramatically reduces binding to Kallikrein by a factor of ~100000, effectively rendering the molecule pharmacologically inert. The importance of the correct sequence of the amino acids is underlined by the four scrambled peptides (Scram 1-4), as all of them display a substantial reduction in affinity towards Kallikrein (FIG. 10). Curiously, all peptides have a roughly identical rat plasma stability profile (between 1 to 2 days, method #1), indicating that plasma protease recognition relies on the presence of the arginine (producing a degradation pattern similar to FIG. 7), and not on its position within the sequence.

Next, five derivatives of Ac-06-34-18(TMB)-NH2 were generated where $W_2$, $P_3$, $A_4$, $R_5$, and $C_2$ were replaced with their respective D-enantiomeric counterparts (Table 9).

From the data it is clear that D-amino acid replacement of $A_4$, $R_5$, and $C_2$ increase peptide stability towards plasma proteases. As Arg5 excision by rat plasma proteases appears to be the first event in peptide degradation, the initial hydrolysis of peptide bonds will occur on the N- and/or C-terminal side of Arg5. It is plausible that replacing the amino acids to either side of Arg5 with their D-enantiomers blocks adjacent peptide bond hydrolysis through steric hindrance. Indeed, this is an effect that has been observed previously (Tugyi et al (2005) PNAS, 102(2), 413-418).

The detrimental effect of D-amino acid substitution on affinities to Kallikrein is striking in all cases; losses in potencies range from 300- (D-Arg5) to 45000-fold (D-Trp2). This underlines the importance of the correct three-dimensional display of these sidechains to the Kallikrein bicycle binding pocket. Equally striking is the effect of D-Ala4: here, changing the orientation of a single methyl group (being the Ala side chain) reduces the affinity 7000-fold.

N-Methylations:

Next, residues in the first loop were systematically replaced with their N-methyl counterparts. N-methylation serves as a straightforward protection of the peptide bond itself; however, due to the absence of the amide hydrogen, addition of steric bulk (the methyl group) and changes in preferred torsional angles, losses in potencies are expected. Table 10 summarises the data.

N-methylation of amino acids in loop 1 displays an altogether less drastic detrimental effect on potency. In particular, N-methylation of Arg5 still yields a single digit nanomolar binder (20-fold reduction in affinity compared to wildtype peptide), and its rat plasma stability exceeds the assay time (fragmentation of the peptide in the MS was not observable), making this an attractive improved lead candidate. As with the D-amino acid substitutions, N-methylation of residues adjacent to Arg5 imparts enhanced stability to the peptide, presumably through steric interference affecting protease-catalysed hydrolysis of peptide bonds N and/or C-terminal to Arg5. Of note, Ser1 can be N-methylated without a significant loss in potency, indicating that the integrity of the peptide backbone in this position is not essential for binding.

Arginine Substitutions:

Given the importance of Arg5 in recognition by rat plasma proteases, a set of arginine analogues were tested in the Ac-06-34-18(TMB)-NH2 lead. The chemical structures are shown in FIG. 11, and the potency versus stability data is shown in Table 11.

Strikingly, all arginine analogues increase the stability of the peptide beyond the assay window time, confirming the importance of the integrity of Arg5 in plasma protease recognition. Increasing (HomoArg) or decreasing the length of the side chain (Agb, Agp) both decrease affinity, however the HomoArg analogue still yields a very good binder (Ki=2.1 nM), with enhanced stability. Lengthening the amino acid backbone by one methylene group in Arg5 (a so-called beta-amino acid) while retaining the same side chain (β-homoArg5) also yields a binder with enhanced stability, however at the price of a more significant reduction in affinity (Ki=8.2 nM). Replacing the aliphatic part of the Arg side chain with a phenyl ring yields a resonance stabilised, bulkier and rigidified guanidyl-containing side chain (4GuanPhe). Of all the Arg analogues tested, 4GuanPhe had the greatest affinity (2-fold reduction compared to wildtype), at an enhanced plasma stability. Interestingly, the guanidylphenyl group is structurally close to the known small molecule Kallikrein inhibitor benzamidine (Stürzebecher et al (1994), *Novel plasma Kallikrein inhibitors of the benzamidine type*. Braz J Med Biol Res. 27(8): 1929-34; Tang et al (2005), *Expression, crystallization, and three-dimensional structure of the catalytic domain of human plasma Kallikrein*. J. Biol. Chem. 280: 41077-89). Furthermore, derivatised Phenylguanidines have been employed as selective inhibitors of another serine protease, uPA (Sperl et al, (4-*aminomethyl*)*phenylguanidine derivatives as nonpeptidic highly selective inhibitors of human urokinase* (2000) Proc Natl Acad Sci USA. 97(10):5113-8.). Thus, Ac-06-34-18(TMB)-NH2 containing 4GuanPhe5 can be viewed as a small molecule inhibitor, whose selectivity is imparted by the surrounding Bicyclic peptide. This can comprise a principle for other bicycle-based inhibitors, where a known small molecule inhibitor of low selectivity is "grafted" onto a Bicycle in the correct position, leading to a molecule of superior potency and selectivity.

Modification of the Arg guanidyl group itself, either by methylation (SDMA, NDMA), removal of the positive charge (Cit, where the guanidyl group is replaced by the isosteric but uncharged urea group) or deletion of the Arg altogether (Δ Arg) has strongly detrimental effects on Kallikrein binding potency. Thus, the integrity and presence of the guanidyl group is crucial, while the nature of the sidechain connecting to the guanidyl group or backbone at Arg5 is not. Of note, Arg5 may also be replaced by lysine, however again at reduced affinities (see WPAK (SEQ ID NO: 221) peptide).

In summary, data this far indicates that Ac-06-34-18 (TMB)-NH2 employing either HomoArg, NMeArg or 4GuanPhe as arginine replacements could constitute plasma stability enhanced candidates with high affinities.

Example 5: Improving the Potency of a Lead Candidate Through Non-Natural Modifications and Combination with Plasma-Stability Enhancing Modifications Improving the potency of a given bicyclic candidate can be feasibly achieved through several mechanisms. These have been partially addressed in Example 4, and can be rewritten as follows:
1. Incorporating hydrophobic moieties that exploit the hydrophobic effect and lead to lower off rates, such that higher affinities are achieved.
2. Incorporating charged groups that exploit long-range ionic interactions, leading to faster on rates and to higher affinities (see for example Schreiber et al, Rapid, electrostatically assisted association of proteins (1996), Nature Struct. Biol. 3, 427-31)
3. Incorporating additional constraint into the peptide, by i.e.
   Constraining side chains of amino acids correctly such that loss in entropy is minimal upon target binding
   Constraining the torsional angles of the backbone such that loss in entropy is minimal upon target binding
   Introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Tryptophan and Hydrophobic Analogue Substitutions:

Initially, a range of hydrophobic amino acids were substituted into the Trp2 site to identify candidates that could replace the oxidation sensitive tryptophan, and to identify candidates that could increase potencies (addressing the first point above). The side chains of these amino acids are shown in FIG. 12, and affinity data is summarised in Table 12 below.

As expected, none of the modifications increase plasma stability. 2-Naphtylalanine is most closely related to Trp2 and displays a potency slightly weaker than wildtype, making this a good, oxidation-resistant replacement for Trp2. Interestingly, 3,3-DPA2 has a structure that is very dissimilar to Trp, yet the corresponding peptide retains high potency. This may indicate that the Trp contacting pocket on Kallikrein could be exploited for higher affinity binding by identifying a correctly designed hydrophobic entity.

Proline Analogues:

Next, we were interested in determining the role of Pro3 in the WPAR pharmacophore in Ac-06-34-18(TMB)-NH2. 4-hydroxy- or 4-fluoro-trans (L)-proline (HyP3, 4FluoPro3) were chosen for their known property in inducing additional rigidity and helicity on the peptide backbone (FIG. 13, Table 13). Additionally, the presence of the hydroxyl on HyP probes the solvent accessibility of the proline side chain. Ki's of the respective derivatives were almost identical to that of wildtype, indicating that any effects on the peptide backbone are negligible, but also demonstrating that the side chain is accessible. To elaborate this further, two additional derivatives of Ac-06-34-18(TMB)-NH2 were tested, which contained bulky extension on the γ-carbon of the Pro3 sidechain (4Phenyl-Pro, 4Benzyl-Pro). The former displayed a striking preservation of potency, while the latter was severely impacted, demonstrating that the Pro side chain is accessible, but limited to distinct modifications only. Despite the steric bulk in these modifications, plasma stability was identical to that of wildtype. Thus, these modifications do not improve selectivity against other proteases.

To probe the effect of proline ring size on binding, the highly constrained 4-membered Pro analogue azetidine carboxylic acid (Aze), and the more flexible 6-membered ring (pipecolic acid, Pip) were substituted for Pro3. Ac-06-34-18(TMB)-NH2 Aze3 binds Kallikrein with the highest affinity of all derivatives so far, surpassing that of wildtype by a factor of 3 (FIG. 14, Table 13). There appears to be an inverse relationship between ring size and Ki, which would suggest that conformational constraint at position 3 of Ac-06-34-18(TMB)-NH2 is key to a tightly binding molecule.

The flexibility of the proline side chain in tolerating large bulky groups is underlined by the bi/tricyclic proline analogues Tic, NorHar and Ind (FIG. 13). Particularly for the latter two cases, affinities are still well in the one digit nanomolar range.

Finally, we sought to probe the requirement for the ring structure at Pro3 altogether. To this end, we chose aminoisobutyric acid (Aib, FIG. 15, Table 13), which, due to its double methyl substitution at the alpha carbon, has a strong structural effect on the neighbouring amino acids in inducing α or $3_{10}$ helicity (Toniolo et al (1993), Biopolymers 33, 1061-72; Karle et al (1990), Biochemistry 29, 6747-56). Remarkably, this non-natural non-cyclic amino acid is well tolerated in place of Pro3, at a Ki of 1.2 nM. Thus, the role of Pro3 in the WPAR pharmacophore is to introduce a constraint onto the peptide backbone. This constraint can be enhanced by employing a proline analogue with reduced ring size (see Aze3). Conversely, the proline ring can be replaced relatively efficiently with non-cyclic but structure-inducing amino acids, such as Aib.

Miscellaneous Analogues:

In table 10, it was shown that Ser1 in loop 1 of Ac-06-34-18(TMB)-NH2 could be N-methylated with very minor impact on potency (0.5 versus 0.17 nM Ki in WT). We sought to determine whether this location tolerated a large double substitution on Cα at position 1. To this end, Ser1 was replaced with Dpg (dipropylglycine) (FIG. 15). The affinity of this peptide to Kallikrein is at 1.1 nM, indicating that position 1 is very flexible in accommodating virtually any bulky residue. Thus, this position in loop 1 could be exploited for deliberate inclusion of desirable chemical functionalities or groups, including solubilising amino acids, radio labels, dye labels, linkers, conjugation sites et cetera.

Several alanine analogues were also tested at position 4. As already seen with the N-methyl and D-alanines (Table 10, 9), Ala4 is highly sensitive to the steric orientation at Cα, or to modification on the backbone itself. Two more derivatives of this class underline this, as elongation of the peptide backbone at Ala4 (β-Ala4) dramatically reduces affinity (~20 μM). As expected from D-Ala4, Aib4 reduces affinity to almost the same extent (289 nM, FIG. 15 and Table 14). Remarkably, extension of the Ala sidechain by one methylene (Aba4) appears to enhance the affinity to Kallikrein.

Finally, the central cysteine (Cys2) was replaced with a bulkier and more constrained analogue, penicillamine (Pen, FIG. 15) in the hope of increasing proteolytic stability due to reduced spatial access to the neighbouring Arg5 protease recognition point. Indeed, rat plasma stability was slightly enhanced, however potency dropped significantly, underlining the importance of the full integrity of this structural scaffold-connecting residue.

Combination of Plasma Stability Enhancing and Potency Enhancing Non-Natural Amino Acids into a Single Bicycle Lead Non-natural substitutions in Ac-06-34-18(TMB)-NH2 that retained appreciable potency and maximal rat plasma stability (as determined by method #1) were the Arg5 variants homoarginine (HomoArg5), 4-guanidylphenylalanine (4GuanPhe5) and N-methyl arginine (NMeArg5). Non-natural substitutions in Ac-06-34-18(TMB)-NH2 that increased potency compared to the wildtype peptide was the Pro3 analogue azetidine carboxylic acid (Aze3) and the Ala4 analogue 2-aminobutyric acid (Aba4). Thus, Aze3, Aba4 were combined with the protease stability enhancing HomoArg5, 4GuanPhe5 and NMeArg5 to determine whether this would yield peptide candidates with high plasma stability and increased potency.

Table 15 and 16 present the affinities of the various constructs, together with the plasma stabilities.

Firstly, quantitative determination of rat plasma halflives (4th column, Table 15) of arginine analogue containing peptides revealed that Arg5 N-methylation was most potent in protecting the peptide ($t_{1/2}$>20 hrs) followed by HomoArg5 and GuanPhe5. The strong protective effect of Arg N-methylation is perhaps not surprising as it directly prevents hydrolysis of the peptide bond. Upon inclusion of Aze3 in these compounds, the affinity of these peptides could be enhanced in all cases, making Ac-(06-34-18) Aze3 HomoArg5 and Ac-(06-34-18) Aze3 NMeArg5 attractive candidates for further development (Table 15, FIG. 16).

The affinity enhancing effect of Aba4 could not be reproduced in the context of Aze3 and any of the arginine analogues, as Ki values were higher than those observed without Aba4. Thus, the potency enhancing effects of Aze3 are independent of the type of Arginine substitution, while those of Aba4 are likely not.

Finally, the activity towards rat Kallikrein of these peptides is reduced significantly (Table 15). However, these values are relative and not quantitative at this stage as the protein preparation of rat Kallikrein is not trivial and contained impurities.

Example 6: Plasma Stability Enhancement of the Try-Free FPYR Kallikrein Bicycle Lead and Affinity Enhancement by Aze3

From the selection output in Examples 1-4 we discovered several sequences resembling Ac-06-34-18(TMB)-NH2 that had a high abundance, but contained altered WPAR motifs. These were WPSR (SEQ ID NO: 20) and FPYR (SEQ ID NO: 25). The latter in particular is interesting as it lacks the oxidation-sensitive tryptophan.

Bicycles containing WPSR (SEQ ID NO: 20), FPYR (SEQ ID NO: 25), WPYR (SEQ ID NO: 26) and FPAR (SEQ ID NO: 31) were synthesised and compared against the WPAR (SEQ ID NO: 19) parent peptide (Table 21)

As expected, none of the peptides displayed a significantly different plasma stability. The replacement of Trp2 with Phe2 incurs a 40-fold reduction in Ki, underlining the requirement of the bulkier Trp2 side chain. However, this reduction can be compensated by replacing Ala4 with Tyr4 (giving the FPYR (SEQ ID NO: 25) motif), so that the affinity increases again to almost that of the wildtype WPAR (SEQ ID NO: 19) sequence (Ki=0.46 nM). Thus, there is a cooperative interplay between the residues at position 2 and position 4 of the Ac-06-34-18(TMB)-NH2 bicycle. Given the high target binding affinity and lack of Trp2 in Ac-06-34-18(TMB)-NH2 Phe2Tyr4, this candidate was investigated for increasing rat plasma half life employing the approach as described in the example above. Further, we investigated the interplay between Phe2 and Tyr4 by substituting these residues with non-natural amino acid analogues.

Non-Natural Substitutions of Phe2/Tyr4 in Ac-06-34-18 (TMB)-NH2 Phe2Tyr4

We performed a non-exhaustive set of syntheses incorporating replacements on Phe2 or Tyr4 in the Ac-06-34-18 (TMB)-NH2 Phe2Tyr4 lead. Non-natural amino acids were chosen from the same set as in FIG. 12, and affinity data is summarised in Table 22.

Here, substitution with any of the amino acids tested is generally well tolerated, regardless whether the sidechain is a heteroaromatic (3Pal, 4Pal), aromatic and bulky (1Nal, 2Nal, 4,4-BPal) or a cycloaliphatic (Cha) entity. 3Pal is well tolerated at position 2 (Ki=0.91), which is interesting as Pal contains an ionisable group (which could i.e. be exploited for formulation). It appears, however, that the original Phe2/Tyr4 combination remains most potent.

Stabilisation of Ac-06-34-18(TMB)-NH2 Phe2Tyr4 in Rat Plasma and Effect of Azetidine Carboxylic Acid 3 Substitution Ac-06-34-18(TMB)-NH2 Phe2Tyr4 was prepared with the homo-arginine, 4-guanidylphenylalanine and N-methyl-arginine substitutions, in absence and presence of Aze3. HomoArg/4Guanphe are well tolerated, with Ki values almost identical to the parent Phe2Tyr2 peptide (Table 23,), and rat plasma stability was enhanced by a factor of 13 ($t_{1/2}$=12.2 hrs, Table 23, FIG. 16). Moreover, IC50 values for rat Kallikrein are similar to that of parent, indicating this to be an attractive candidate for in vivo studies.

Pro3 to Aze3 substitution in the FPYR (SEQ ID NO: 25) context again yielded peptide candidates with enhanced affinity, indeed a peptide with a Ki less than 1 nM was generated that would likely have a greater half-life than 20 hrs in rat (Ac-(06-34-18) Phe2 Aze3Tyr4 NMeArg5).

Example 7: Improving the Human Plasma Stability of the 06-34-18 Bicycle Lead Candidate Through Single Amino Acid Substitutions in Loop 2

Identification of His7 as a Major Plasma Protease Recognition Site

Rat and human plasma stability of the following loop 1—modified 06-34-18 peptides were determined quantitatively using LC-MS (Method #3, Table 2). It is clear that the chemical modifications (HArg5, 4GuanPhe5, NMe-Arg5) that impart stability to rat plasma proteases are not effective in the proteolytic context of human plasma.

Ac-06-34-18(TMB)-NH2 Phe2 Tyr4 (referred to as wild type peptide) was subsequently subjected to human plasma, and analysed for fragments to appear over time. This was compared to the degradation profile observed in human plasma using the NMe-Arg5 derivative of 06-34-18 (FIGS. 18*a* and 18*b*). Fragmentation was determined according to Method #2.

According to the mass spectrometric information, endoproteolytic hydrolysis occurs on either the N- and/or C-terminal side of His7 in the 06-34-18 sequence, subsequently excising Leu6 (through an exo-proteolytic activity) or His7-Gln8 (through an exo-proteolytic activity) or all three residues together. From the nature of the fragments observed, it is likely that the initial endoproteolytic hydrolysis event occurs on the peptide bond between Leu6 and His7, rather than between His7 and Gln8. Moreover, the same fragmentation pattern is observed if the rat plasma protease recognition point on Arg5 is blocked with N-methylation (FIG. 18*b*), indicating that the proteolytic specificity of human plasma is distinct from that of rat.

Systematic Assessment of the Role of Loop 2 Residues, and Stabilisation Against Plasma Proteases.

Subsequently, the role of each of the loop 2 residues in terms of their effects on human plasma stability and human kallikrein potency was assessed.

Using experimental approaches partially outlined in the background to the invention section, a full loop 2 amino acid scan was performed by
1) replacing each of the loop 2 amino acids with Alanine to remove the side chain that serves as a recognition point for the protease(s)
2) replacing each of the loop 2 amino acids with their D-amino acid enantiomeric counterparts to sterically oppose access by the degradative protease(s)
3) replacing some of the loop 2 amino acids with D-alanine, to sterically oppose access to the peptide bonds by the protease(s)

The potency data for each variant are summarised in Tables 3a, 3b, and 3c, respectively.

1) Alanine Scan of Loop 2 Residues Table 3a shows that modification of His7 with Ala7 appears to reduce proteolytic degradation in the second loop, as -L, -HQ, -LHQ fragments were not detectable. However, proteolytic activity in loop 1 on Arg5 (which was previously observed only with rat plasma) now becomes detectable. Thus it is clear that human plasma proteases are capable of attacking both proteolytic recognition points (Arg5 and His7). Even though Ala7 appears to enhance stability compared to His7 (as in wild-type peptide), its potency is reduced significantly (56-fold), bringing the Kd to 23 nM, which is not sufficiently potent for a therapeutic molecule. The remaining Ala replacements all reduce potencies to varying degrees, without increasing plasma stability however (as judged by the appearance of Loop2 degraded Bicycle Peptide fragments, Table 3a fourth column). Together, this underlines the finding that the side-chain of His7 is the protease recognition point.

2) D-Amino Acid Scan of Loop 2 Residues

Table 3b shows the effect of replacing each of the amino acids with their D-enantiomeric counterparts. This modification leaves the sidechain intact, but projects it in the alternate configuration on Cα. The D-amino acids at any position within loop 2 appear to stabilise loop 2 of the peptide from proteolytic degradation; however, as seen with the Ala7 variant above, specificity switches now to the labile site in loop 1 (Arg5). The switch of hydrolysis to Arg5 made it difficult to quantify the effect of D-amino acid-induced stabilisation in loop2, as this independent process impacts the quantity of remaining parent material (addressed further below). The distal protective effect of D-amino acid substitution has been recognised in the literature and likely functions by sterically reducing or preventing access to the hydrolysable bond (Tugyi et al (2005) PNAS, 102(2), 413-418). However, D-amino acids progressively further away from the putative His7 protease recognition site (i.e. D-Asp9, D-Leu10) also show a smaller quantity of fragments corresponding to an excised Leucine 6, which is adjacent to His7.

Notably, most of the D-amino acid variants display strongly reduced potencies (between 130 to 9000-fold reduction in potency), underlining the 3-dimensional and steric nature of the interaction of peptide with the kallikrein protein. D-Asp9 appears to be the exception, in that an increase in stability is observed, while 4 nM (9-fold reduction compared to WT) potency is maintained. This modification could potentially be a useful stabilising substitution in a candidate therapeutic molecule.

3) D-Alanine Scan of Loop 2 Residues

Table 3c shows the effect of replacing a few select loop 2 amino acids with D-Alanines. Removing the side chains and introducing the steric block on Cα due to the presently introduced methyl group has strongly detrimental effects on potencies. Nonetheless, in two cases low nanomolar affinities are retained (Ac-(06-34-18) D-Ala9, and Ac-(06-34-18) Phe2 Tyr4 D-Ala9). As with D-Asp9, these modifications could potentially be a useful stabilising substitution in a candidate therapeutic molecule.

Replacement of Amino Acid Sidechains on Leu6, His7 and Gln8 with Amino Acid Mimetics Subsequently a campaign of amino acid substitution of Leu6, His7 and Gln8 was undertaken to evaluate the steric, charge, and structural requirements of these residues, and to evaluate their effect on reducing recognition of the His7 site by plasma proteases (a structure of Loop2 is presented in FIG. 19*a*).

General approaches that are suitable were discussed previously in the introductory section.

Substitutions at Position 6 in Loop2 of 06-34-18

At residue Leu6, it was sought to introduce steric bulk at C13 of the amino acid, with the aim of reducing protease access to the scissile bond between Leu6 and His7. The structures tested are shown in FIG. 19*b*. The effect on potency is summarised in Table 24a. Some of the modifications show enhancement of affinities compared to the wildtype peptide, particularly in the context of Ac-(06-34-18) (less so in the context of Ac-(06-34-18) Phe2 Tyr4). Specifically, these are the non-natural amino acids phenylglycine (Phg) and cyclohexylglycine (Chg). All of these modifications appeared to somewhat reduce the proteolytic cleavage in the second loop, but the most potent stabiliser proved to be tert-butylglycine (tBuGly). This peptide, Ac-(06-34-18) Phe2 Tyr4 tBuGly6, showed only removal of Arg5 in the first loop when subjected to human plasma. Together, any of the Chg, Phg, and tBuGly modifications could serve to enhance second loop plasma stability. In addition, we identified two modifications (Chg, Phg) that enhance the potency towards Kallikrein.

Substitutions at Position 7 in Loop2 of 06-34-18

At residue 7, the effect on plasma stability and potency by replacing the histidine side chain was studied employing the following mimics: The pyridylalanines 2Pal, 3Pal, 4Pal are basic ionisable heteroaromatic mimics of the imidazole sidechain. Thienylalanine (Thi), furylalanine (FuAla), ThiAz, 1,2,4 triazolalanine, (1,2,4 Triaz), thiazolylalanine (ThiAz) are 5-membered heteroaromatic uncharged mimics of the imidazole side chain. His1Me/His3Me are N-methyl substituted derivatives of the imidazole side chain. Dap, Agb and Agp represent positive charge replacements of the imidazole side chain, lacking an aromatic sidechain however (FIG. 19*c*). Table 24b summarises the potency data. Strikingly, all peptides display an enhanced stability towards plasma proteases in loop2, visible degradation occurred only in Loop 1 on Arg5. Clearly, a positive charge at position 7 is not sufficient to provide a recognition point for plasma proteases (Dap, Agp, Agb). Conversely, removal of the positive charge while retaining close mimicry of the original imidazole side chain also removes the proteolytic recognition site. Despite the very close mimicry of some of structures to the original imidazole ring, all of the peptide derivatives display a significantly reduced affinity to plasma kallikrein. This indicates that the intact structure of His 7 is required for binding to kallikrein with full potency. Interesting candidates that retained low-nanomolar binding were thiazolylalanine, furylalanine, and His1Me. Interesting putative candidates could be homohistidine, and imidazolylglycine.

Substitutions at Position 8 in Loop2 of 06-34-18

Residue 8 (Gln8) is more distal to the cleavage site that resides between Leu6 and His7. A few substitutions were tested (FIG. 19d and Table 24c). Negatively charged amino acids were introduced at this position so as to encourage a salt bridge to the neighbouring His7, which could reduce recognition of His7 by plasma proteases. An additional Loop2 sequence was tested that was present in the phage selection outputs, which also lacked a histidine 7. This loop 2 sequence was LTTEL (SEQ ID NO: 32) (referred to as Ac-(06-34-18) Phe2 Tyr4 Thr7 Thr8 Glu9). Additionally, a beta amino acid was tested at position 8 (bHGln8, FIG. 19d). A positive charge amino acid was also tested at this position so as to potentially thwart proteolytic recognition of His7 and subsequent degradation. While potencies of these molecules were often <10 nanomolar, the effect on plasma stabilisation was minor. These molecules may warrant further quantitative study to determine their precise effects on plasma stability.

Example 8: Improving the Human Plasma Stability of the 06-34-18 Bicycle Lead Candidate Through Amino Acid Backbone Modifications in Loop 2

Amino acid backbone modification presents a widely recognised means by which the peptide backbone can be protected from protease hydrolysis (for reviews see Gentilucci et al, Curr. Pharmaceutical Design, (2010), 16, 3185-203, and Nestor et al, Curr. Medicinal Chem (2009), 16, 4399-418).

A well-established method in the art is to N-alkylate, for example N-methylate the Nα of amino acids. Table 25a shows the effect of systematic replacement of loop two amide backbones with their Nα-methylated counterparts. In principle, this is a very effective hydrolysis-protective modification, as not only the peptide bond itself is protected from proteolytic hydrolysis, but also as the bulk of the methyl group on the Nα has protective effects on neighbouring peptide bonds. Indeed, strongly protective effects on loop2 proteolysis are observable, however potencies invariably decrease by a factor of 100 or greater. As with D-amino acid replacement, N-alkylation protects the scissile site at His7 even when it is present at Asp9 or Leu10.

Another means by which the peptide backbone can be modified is by N-alkylation of the Nα with an appropriate amino acid side chain (termed peptoid). The homohistidine sidechain was introduced at the Nα of His7, while concomitantly removing the side chain on Cα of His7, yielding an N-alkyl glycine. The structure of this derivative is shown in FIG. 20a (termed N-His7), within the context of the entire second loop of 06-34-18.

In an attempt to modify the structure of the peptide backbone itself, a reduced form of the peptide bond was introduced between Leu6 and His7 (FIG. 20b). Here, Leu6 was replaced by Ala6, and the carbonyl on this residue was reduced to methylene, yielding a linkage that lacks the native peptide bond altogether. This derivative is referred to as "reduced amide" or "pseudo peptide bond", and termed ψCH2NH. Due to the absence of the carbonyl on this position, the peptide cannot be hydrolysed at this position and should infer favourable protease stability characteristics to the peptide.

In the plasma assay, both peptide derivatives (Ac-(06-34-18) Phe2 Tyr4 N-His and Ac-(06-34-18) Phe2 Tyr4 Ala (ψCH$_2$NH)6) displayed significantly enhanced stability in loop2. Fragments observed solely corresponded to degradation in Loop 1, on Arg5. Potency data is summarised in Table 25b. As expected, the N-His derivative showed strongly reduced binding. However, the pseudo amide peptide Ac-(06-34-18) Phe2 Tyr4 Ala(ψCH2NH)6) retained a very good potency at a Kd of 1.5 nM.

Example 9: Generation of Potent, Rat and Human Plasma-Stable, Cross-Reactive Bicyclic Peptide Leads by Selective Chemical Modification in Both Loop 1 and Loop 2

From the preceding two examples, several loop 2 modifications were identified that enhanced protease stability in loop2, while displaying a good potency. Retention of an appropriate potency towards rat plasma kallikrein is desirable for establishing PK/PD in animal models. The comparative rat potency is summarised for suitable loop2 stability-enhanced candidates in Table 26a. Most of the molecules display potencies <100 nM towards rat plasma kallikrein.

In Examples 1-6, methods have been disclosed by which Loop 1 of 06-34-18 can be stabilised against plasma proteases. These advantageous modifications are combined with the plasma stability enhancing modifications in Loop 2 (Examples 7, 8). Several representative candidates were prepared and assessed for human/rat plasma stability, as well as potency towards human/rat plasma kallikrein (Table 26b).

Notably, most of the peptides display, when in combination with the loop 1 modifiers, better potencies towards human and rat kallikrein than peptides with the loop 2 modifiers alone (Table 26a). Most of the potencies are in a range acceptable for therapeutic and PK/PD purposes (see human and rat kallikrein data, Table 26b).

Due to the introduction of HArg5 in place of Arg5 in loop1, and due to the introduction of modifications in loop2 that reduced proteolysis at the His 7 site, the peptides shown in Table 26a and 26b should display enhanced stability in both human and rat plasma.

Plasma stability was assessed comparatively as before using the MALDI TOF assay (Methods #1 and #2), and formation of peptidic hydrolysed fragments was observed over time (for wildtype stability, see FIGS. 18a, 21a, 21b). Compared to wildtype peptide, the multivariant peptides Ac-(06-34-18) Phe2 Aze3 Tyr4 HArg5 Ala(ψCH2NH)6 (human plasma stability: FIG. 21d, rat plasma stability: FIGS. 21 e) and Ac-(06-34-18) Phe2 Aze3 Tyr4 HArg5 D-Asp9 (human plasma stability: FIG. 21c) display a remarkably enhanced stability in both human rat plasma.

Together, this shows that suitable modifications both in Loop 1 and Loop 2 of 06-34-18 can be combined to yield highly potent, cross-reactive, and plasma stable bicyclic peptides, which display a profile suitable for therapeutic purposes.

Example 10: Advantageous In Vivo Pharmacokinetic Properties of Two Lead Peptides, Ac-(06-34-18) Phe2 Aze3 Tyr4 HArg5 Ala(ψCH2NH)6 and Ac-(06-34-18) Phe2 Aze3 Tyr4 HArg5 D-Asp9

Peptides Ac-(06-34-18) Phe2 Aze3 Tyr4 HArg5 Ala (ψCH2NH)6 (which contains the affinity enhancing modifications Aze3 and the plasma protease stability enhancing modifications HArg5 and the plasma protease stability enhancing reduced amide bond between Ala6 and His 7 in Loop2) and Ac-(06-34-18) Phe2 Aze3 Tyr4 HArg5 D-Asp9

(which contains the affinity enhancing modification Aze3 and the plasma protease stability enhancing modifications HArg5 and D-Asp9 in Loop2) were selected for pharmacokinetic assessment in rat. The full chemical structure of Ac-(06-34-18) Phe2 Aze3 Tyr4 HArg5 Ala(ψCH2NH)6 is shown in FIG. 22.

The clearance rates from the rat circulation for both peptides were assessed and compared to a control peptide that was composed of the Ac-(06-34-18)(TMB) sequence whose amino acids were replaced by each of the respective D-enantiomers (the sequence thus being "(Ac-cswpar-clhqdlc-NH2(TMB)). This control peptide has identical atomic and sequence composition, retains similar physico-chemical properties, lacks any potency towards the kallikrein target, and importantly is completely resistant to proteolytic activities. Thus, the clearance from the rat circulation of the all D Ac-06-34-18 control peptide is driven mostly renally, as the proteolytically-driven clearance is absent. Any optimised protease-stabilised and potent kallikrein-inhibiting Bicycle that is based on the 06-34-18 sequence should therefore clear from the rat circulation at a rate similar to the control All-D 06-34-18 peptide.

Peptides were applied as intravenous boli in PBS-buffered solution at 1.02 mg/mL (containing 2.9% DMSO) at 5.2 mg/kg to Sprague Dawley rats, and serial blood samples were taken from each animal via temporary indwelling tall vein cannulae at 5, 10, 20, 30, 60, 120, and 240 minutes post dose, and transferred to EDTA tubes for plasma generation. Data was acquired for peptide "all D Ac-06-34-18" from 3 rats, for "Ac-(06-34-18) Phe2 Aze3 Tyr4 HArg5 Ala (ψCH2NH)6" from two rats, and for "Ac-(06-34-18) Phe2 Aze3 Tyr4 HArg5 D-Asp9" from two rats.

Plasma samples were then treated with 3 volumes of a 1:1 mixture of acetonitrile and methanol, precipitated proteins were removed by centrifugation, and the supernatant was analysed by UPLC-MS/MS.

Quantification for peptide content in the samples was by reference to a calbibration line prepared in control rat plasma. Pharmacokinetic parameters were determined by non-compartmental analysis using the software package PK Solutions 2.0 from Summit Research Services.

The peptide (Ac-(06-34-18) Phe2 Aze3 Tyr4 HArg5 Ala (ψCH2NH)6 displayed an elimination half-life of 48 minutes, while the control All D 06-34-18 peptide cleared at a 54 minute half-life. The volumes of distribution for the two peptides were comparable (Table 27, FIG. 23). Thus, the pharmacologically active (Ac-(06-34-18) Phe2 Aze3 Tyr4 HArg5 Ala(ψCH2NH)6 peptide is as stable as the pharmacologically inert protease stable All D 06-34-18 control peptide, indicating that (Ac-(06-34-18) Phe2 Aze3 Tyr4 HArg5 Ala(ψpCH2NH)6 has favorable properties for further development as a therapeutic (FIG. 23). Peptide Ac-(06-34-18) Phe2 Aze3 Tyr4 HArg5 D-Asp9 cleared more rapidly, however, with an elimination half-life of ~27 minutes.

The intravenous pharmacokinetic parameters for the 3 peptides are summarised in Table 27.

The results underline the enhanced proteolytic stability of peptide Ac-(06-34-18) Phe2 Aze3 Tyr4 HArg5 Ala (ψCH2NH)6 in the in vivo circulation of the rat. The clearance at 5.8 mL/min/kg is very close to the published renal filtration rate in rat (~8-9 mL/min/kg), indicating that plasma protease-driven clearance of this Bicyclic peptide is virtually absent [Jobin J, Bonjour J P, (1985) Am J Physiol.; 248(5 Pt 2):F734-8].

Unless otherwise stated, any methods and materials similar or equivalent to those described herein can be used in the practice or testing of the present invention. Methods, devices, and materials suitable for such uses are described above. All publications cited herein are incorporated herein by reference in their entirety for the purpose of describing and disclosing the methodologies, reagents, and tools reported in the publications that might be used in connection with the invention.

Tables

TABLE 1

Potencies, Rat plasma stability and species cross reactivity of Ac-06-34-18 as disclosed in PCT/EP2012/069898.

| Peptide | Ki (nM) (human kallikrein) | Observable in rat plasma, for days[1] | $t_{1/2}$ (hrs) in rat plasma[2] | Ki (nM) (rat kallikrein) |
|---|---|---|---|---|
| Ac-(06-34-18) wildtype | 0.17 | 2.0 | 2.3 | 1.8 |
| Ac-(06-34-18) HomoArg5 | 2.1 | >10 | 10.7 | 101 |
| Ac-(06-34-18) 4GuanPhe5 | 0.14 | >10 | 2.8 | 3.0 |
| Ac-(06-34-18) NMeArg5 | 3.5 | >10 | >20 | 119.7 |
| Ac-(06-34-18) Aze3 HomoArg5 | 0.14 | >10 | nd | 14.8 |
| Ac-(06-34-18) Aze3 4GuanPhe5 | 0.17 | >10 | nd | nd |
| Ac-(06-34-18) Aze3 NMeArg5 | 1.3 | >10 | nd | 70.2 |
| Ac-(06-34-18) Phe2 Tyr4 wildtype | 0.46 | 2 | 0.9 | 7.6 |
| Ac-(06-34-18) Phe2 Tyr4 HomoArg5 | 0.77 | >10 | 12.2 | 16.2 |
| Ac-(06-34-18) Phe2 Tyr4 4GuanPhe5 | 0.40 | >10 | 5.0 | 0.6 |
| Ac-(06-34-18) Phe2 Tyr4 NMeArg5 | 3.56 | >10 | >20 | 64.3 |
| Ac-(06-34-18) Phe2 Aze3 Tyr4 HomoArg5 | 0.12 | nd | nd | 3.0 |
| Ac-(06-34-18) Phe2 Aze3Tyr4 4GuanPhe5 | 0.36 | nd | nd | 1.2 |
| Ac-(06-34-18) Phe2 Aze3Tyr4 NMeArg5 | 0.97 | nd | nd | 31.4 |

[1]Determined according to Method #1.
[2]Determined according to Method #3.
Table reproduced from PCT/EP2012/069898.

TABLE 2

Summary of the ex vivo rat and human plasma stabilities of different Loop1-modified 06-34-18 peptide derivatives, as determined by Method #3.

| | Ki (nM) human Kal | Rat Plasma Stability (t1/2 in hrs) | Human Plasma Stability (t1/2 in hrs) |
|---|---|---|---|
| Ac-06-34-18 Phe2 Tyr4 | 0.42 | 0.9 | 1.4 |
| Ac-06-34-18 Phe2 Tyr4 NMeArg5 | 4 | >20 | 1.7 |
| Ac-06-34-18 Phe2 Tyr4 HomoArg5 | 0.77 | 12.2 | 2.1 |

TABLE 2-continued

Summary of the ex vivo rat and human plasma stabilities of different Loop1-modified 06-34-18 peptide derivatives, as determined by Method #3.

|  | Ki (nM) human Kal | Rat Plasma Stability (t1/2 in hrs) | Human Plasma Stability (t1/2 in hrs) |
|---|---|---|---|
| Ac-06-34-18 Phe2 Tyr4 GuanidylPhe5 | 0.4 | 3 | 2.9 |

TABLE 3a

Alanine Scan in Loop2. Resultant potencies are compared to WT, and peptide fragments observed after incubation in human plasma are noted.

| Alanine Scan of Ac-(06-34-18) Phe2 Tyr4 | Ki (nM) | F (Ki$_{var}$/Ki$_{WT}$) | Fragments (human plasma) |
|---|---|---|---|
| Ac-(06-34-18) Phe2 Tyr4 (wild type) | 0.42 | 1 | -LHQ |
| Ac-(06-34-18) Phe2 Tyr4 Ala6 | 1.90 | 5 | -LHQ, -R |
| Ac-(06-34-18) Phe2 Tyr4 Ala7 | 23.43 | 56 | -R |
| Ac-(06-34-18) Phe2 Tyr4 Ala8 | 1.74 | 4 | -LHQ, -R |
| Ac-(06-34-18) Phe2 Tyr4 Ala9 | 1.58 | 4 | -LHQDL, -R |
| Ac-(06-34-18) Phe2 Tyr4 Ala10 | 13.46 | 32 | -LHQ, -LHQDL, -R |

TABLE 3b

D-amino acid Scan in Loop2. Resultant potencies are compared to WT, and peptide fragments observed after incubation in human plasma are noted.

| D-amino acid scan | Ki (nM) | F (Ki$_{var}$/Ki$_{WT}$) | Fragments (human plasma) |
|---|---|---|---|
| Ac-(06-34-18) Phe2 Tyr4 D-Leu6 | 9078.33 | 21615 | -R, -FPYR |
| Ac-(06-34-18) Phe2 Tyr4 D-His7 | 129.18 | 308 | -R, -FPYR |
| Ac-(06-34-18) Phe2 Tyr4 D-Gln8 | 316.90 | 755 | -R, -FPYR |
| Ac-(06-34-18) Phe2 Tyr4 D-Asp9 | 3.89 | 9 | -R, -FPYR |
| Ac-(06-34-18) Phe2 Tyr4 D-Leu10 | 415.67 | 990 | -R, -FPYR |

TABLE 3c

D-Alanine Scan in Loop2. Resultant potencies are compared to WT. Fragments were similar to those seen with the full D-amino acid replacements (Table 3b). Note that both Ac-(06-34-18) and Ac-(06-34-18) Phe2 Tyr4 were also assessed.

| D-Alanine Scan | Ki (nM) | F (Ki$_{var}$/Ki$_{WT}$) |
|---|---|---|
| Ac-(06-34-18) D-Ala6 | 1037.00 | 2469 |
| Ac-(06-34-18) D-Ala8 | 11.67 | 28 |
| Ac-(06-34-18) D-Ala9 | 0.87 | 2 |
| Ac-(06-34-18) Phe2 Tyr4 D-Ala6 | 9453.00 | 22507 |
| Ac-(06-34-18) Phe2 Tyr4 D-Ala8 | 242.60 | 578 |
| Ac-(06-34-18) Phe2 Tyr4 D-Ala9 | 19.87 | 47 |
| Ac-(06-34-18) Phe2 Tyr4 D-Ala10 | 572.15 | 1362 |

TABLE 4

5 x 5 peptides

|  | Sequence |  | SEQ ID NO: | Kallikrein Av Ki (nM) | Thrombin Ic50 | Factor XIIa |
|---|---|---|---|---|---|---|
| 06-01 | ACAWPARCLTVDLCA | A C A W P A R C L T V D L C A | 33 | <0.1* | >10000 | >10000 |
| 06-34 | ACRWPARCVHQDLCA | A C R W P A R C V H Q D L C A | 34 | <0.3* | >10000 | >10000 |
| 06-57 | ACSWPARCNHQDLCA | A C S W P A R C N H Q D L C A | 35 | 0.4 | >10000 | >10000 |
| 06-59 | ACRWPARCLTTSLCA | A C R W P A R C L T T S L C A | 36 | 0.5 | >10000 | >10000 |
| 06-54 (2A2) T | ACRWPARCTHQNYCA | A C R W P A R C T H Q N Y C A | 37 | 0.49 | >10000 | >10000 |
| 06-09 | ACTWPARCTHQNWCA | A C T W P A R C T H Q N W C A | 38 | 1.2 | >10000 | >10000 |
| 06-143 | ACFPSHDCDGRRMCA | A C F P S H D C D G R R M C A | 39 | 1.27 | >10000 | >10000 |
| 06-56 | ACGGPQNCRTWTTCA | A C G G P Q N C R T W T T C A | 40 | 2.1 | >10000 | >10000 |
| 06-157 | ACNWPYRCLHTDLCA | A C N W P Y R C L H T D L C A | 41 | 3.3 | >10000 | >10000 |
| 06-61 | ACSWPYRCLHQDYCA | A C S W P Y R C L H Q D Y C A | 42 | 5.8 | >10000 | >10000 |
| 06-64 T | ACGVPYRCTHQEMCA | A C G V P Y R C T H Q E M C A | 43 | 6.9 | >10000 | >10000 |
| 06-A2* | ACTWPARCTMQNWCA | A C T W P A R C T M Q N W C A | 44 | 181 |  | >10000 |
| 06-63 T | ACADPWACLFRRPCA | A C A D P W A C L F R R P C A | 45 | 1277 | >10000 |  |
| 1E6 | ACAWPARCLTTSLCG | A C A W P A R C L T T S L C G | 46 | 0.16 | >10000 | >10000 |
| 2A10 | ACTYPYKCLHQNLCA | A C T Y P Y K C L H Q N L C A | 47 | 4.98 |  |  |
| 1B1 | ACAWPAKCLTRELCA | A C A W P A K C L T R E L C A | 48 | 8.1 |  |  |
| 1F7 | ACGGYNNCRAFSYCA | A C G G Y N N C R A F S Y C A | 49 | 2.2 |  |  |

TABLE 5

06-34 - substitutions based on identification of
non-critical residues with natural amino acids

| Peptide | Sequence | IC50 human PK (nM) | IC50 rat PK (nM) | SEQ ID NO: |
|---|---|---|---|---|
| 06-34 | ACRWPARCVHQDLCA* | 0.19 | 7.38 | 34 |
| 06-34-01 | ACSWPARCVHQDLCA | 0.15 | 6.12 | 50 |
| 06-34-02 | ACRWPARCTHQDLCA | 0.16 | 1.09 | 51 |
| 06-34-03 (01 + 02) | ACSWPARCTHQDLCA | 0.082 | 0.87 | 52 |
| 06-34-04 | ACRWPARCMHQDLCA | 0.075 | 0.56 | 53 |
| 06-34-05 | ACRWPARCLHQDLCA | 0.076 | 0.62 | 54 |
| 06-34-17 (01 + 04) | ACSWPARCMHQDLCA | 0.073 | 0.44 | 55 |
| 06-34-18 (01 + 05) | ACSWPARCLHQDLCA | 0.070 | 0.56 | 56 |
| 06-34-19 (01 +05 + R/K) | ACSWPAKCLHQDLCA | 0.19 | 4.67 | 57 |

*Residue numbering is from left to right, where residues 1-5 are in loop 1, and residues 6-10 are in loop 2.

TABLE 6

06-34 - substitutions based on identification of non critical residues with N-methylated amino acids

| Peptide | Sequence | Ki human PK (nM) | SEQ ID NO: |
|---|---|---|---|
| 06-34 | ACRWPARCVHQDLCA | 0.128 | 34 |
| 06-34-03 - Ala1,6 | ACAWPARCAHQDLCA | 0.147 | 58 |
| 06-34-03 - N-MeGly1,6 | AC(N-MeG)WPARC(N-MeG)HQDLCA | 24.8 | 59 |
| 06-34-18 | ACSWPARCLHQDLCA | 0.040 | 60 |
| 06-34-18 - N-MeSer1 | AC(N-MeS)WPARCLHQDLCA | 0.560 | 61 |

TABLE 7

| Supplier | Short name | Full chemical name |
|---|---|---|
| AGTC | D-Asp | Fmoc-D-Asp(tBu)-OH |
| Anaspec | NDM-Arg | Fmoc-Nωωdimethyl-L-arginine |
| Anaspec | NMe-Ser | Fmoc-Nα-methyl-O-t-butyl-L-serine |
| Anaspec | NMe-Trp | Fmoc-Nα-methyl-L-tryptophan |
| Anaspec | NorHar | Fmoc-L-1;2;3;4-tetrahydro-norharman-3-carboxylic acid |
| Anaspec | 4PhenylPro | Fmoc-(2S;4S)-4-phenyl-pyrrolidine-2-carboxylic acid |
| Iris Biotech | Agb | Fmoc-L-Agb(Boc)2-OH |
| Iris Biotech | Agp | Fmoc-L-Agp(Boc)2-OH |
| Iris Biotech | β-Ala | Fmoc-beta-Ala-OH |
| Iris Biotech | Cit | Fmoc-Cit-OH |
| Iris Biotech | D-Cys | Fmoc-D-Cys-OH |
| Iris Biotech | β-HArg | Fmoc-L-beta-HArg(Pbf)-OH |
| Iris Biotech | NMe-Arg | Fmoc-L-MeArg(Mtr)-OH |
| Iris Biotech | 3Pal | Fmoc-L-3Pal-OH |
| Iris Biotech | 4Pal | Fmoc-L-4Pal-OH |
| Iris Biotech | Pen | Fmoc-Pen(Trt)-OH |
| Iris Biotech | D-Pro | Fmoc-D-Pro-OH |
| Iris Biotech | Tic | Fmoc-L-Tic-OH |
| Iris Biotech | D-Trp | Fmoc-D-Trp-OH |
| Merck Novabiochem | Aib | Fmoc-Aib-OH |
| Merck Novabiochem | D-Ala | Fmoc-D-Ala-OH |
| Merck Novabiochem | D-Arg | Fmoc-D-Arg(Pbf)-OH |
| Merck Novabiochem | 4GuanPhe | Fmoc-Phe(bis-Boc-4-guanidino)-OH |
| Merck Novabiochem | D-Gln | Fmoc-D-Gln(Trt)-OH |
| Merck Novabiochem | D-His | Fmoc-D-His(Trt)-OH |
| Merck Novabiochem | Hyp | Fmoc-Hyp(tBu)-OH |
| Merck Novabiochem | D-Leu | Fmoc-D-Leu-OH |
| Merck Novabiochem | NMe-Ala | Fmoc-L-MeAla-OH |

TABLE 7-continued

| Supplier | Short name | Full chemical name |
|---|---|---|
| Merck Novabiochem | NMe-Cys | Fmoc-N-Me-Cys(Trt)-OH |
| Merck Novabiochem | SDMA | Fmoc-SDMA(Boc)2-ONa |
| Merck Novabiochem | HArg | Fmoc-L-HArg(Boc)2-OH |
| Peptech Corporation | 4,4-BPAl | Fmoc-L-4,4'-Biphenylalanine |
| Peptech Corporation | 3,3-DPA | Fmoc-L-3,3-Diphenylalanine |
| Peptech Corporation | Dpg | Fmoc-Dipropylglycine |
| Peptech Corporation | 1NAl | Fmoc-L-1-Naphthylalanine |
| Peptech Corporation | 2NAl | Fmoc-L-2-Naphthylalanine |
| Peptech Corporation | Pip | Fmoc-L-Pipecolic acid |
| Polypeptide Group | Aba | Fmoc-L-2-aminobutyric acid |
| Polypeptide Group | Aze | Fmoc-L-azetidine-2-carboxylic acid |
| Polypeptide Group | 4BenzylPro | (2S,4R)-Fmoc-4-benzyl-pyrrolidine-2-carboxylic acid |
| Polypeptide Group | Cha | Fmoc-beta-cyclohexyl-L-alanine |
| Polypeptide Group | 4FluoPro | (2S,4R)-Fmoc-4-fluoro-pyrrolidine-2-carboxylic acid |
| Polypeptide Group | Ind | Fmoc-L-Indoline-2-carboxylic acid |
| AGTC | D-Asp | Fmoc-D-Asp(tBu)-OH |
| Merck Chemicals | Thi | Fmoc-L-Thi-OH |
| Sigma | 4ThiAz | Fmoc-β-(4-thiazolyl)-Ala-OH |
| Santa Cruz Biotechnology | 1,2,4-TriAz | Fmoc-3-(1,2,4-triazol-1-yl)-Ala-OH |
| Combi-Blocks | 4FuAla7 | Fmoc-L-2-Furylalanine |
| Fluorochem | N-His | 2-(1-Trityl-1H-imidazol-4-yl)-ethylamine |
| Iris Biotech | Agb | Fmoc-L-Agb(Boc)2-OH |
| Iris Biotech | Agp | Fmoc-L-Agp(Boc)2-OH |
| Merck | 1MeHis | Fmoc-1-methyl-L-histidine |
| Merck | 3MeHis | Fmoc-3-methyl-L-histidine |
| Sigma | bHGln | Fmoc-ß-Homogln(Trt)-OH |
| Iris Biotech | 3Pal | Fmoc-L-3Pal-OH |
| Iris Biotech | 4Pal | Fmoc-L-4Pal-OH |
| Merck Novabiochem | D-Leu | Fmoc-D-Leu-OH |
| Merck Novabiochem | HArg | Fmoc-L-HArg(Boc)2-OH |
| Polypeptide Group | Aze | Fmoc-L-azetidine-2-carboxylic acid |
| Combi Blocks | Ala-H | Fmoc-L-Alanine aldehyde |
| Combi Blocks | FuAla | Fmoc-L-2-furylalanine |

TABLE 8

| Peptide | Sequence | KI(nM) (human kallikrein) | Observable in rat plasma, for days | SEQ ID NO: |
|---|---|---|---|---|
| Ac-(06-34-18)WT | Ac-CSWPARCLHQDLC | 0.17 | 2 | 222 |
| Ac-(06-34-18) A2A3 | Ac-CSAAARCLHQDLC | 18545 | 1 | 61 |
| Ac-(06-34-18) A2Q3 | Ac-CSAQARCLHQDLC | 15840 | 1 | 62 |
| Ac-(06-34-18) Scram1 | Ac-CPSAWRCLHQDLC | 1091 | 2 | 63 |
| Ac-(06-34-18) Scram2 | Ac-CWASPRCLHQDLC | 11355 | 2 | 64 |
| Ac-(06-34-18) Scram3 | Ac-CAPWSRCLHQDLC | 1892 | 1 | 65 |
| Ac-(06-34-18) Scram4 | Ac-CWARSPCLHQDLC | 67500 | 1 | 66 |

TABLE 9

Comparative effects of D-amino acid substitution on potency and rat plasma stability.

| Peptide | Ki (nM) (human kallikrein) | Observable in rat plasma, for days |
|---|---|---|
| Ac-(06-34-18) wildtype | 0.17 | 2 |
| Ac-(06-34-18) D-Trp2 | 7558 | 2 |
| Ac-(06-34-18) D-Pro3 | 680 | 3 |
| Ac-(06-34-18) D-Ala4 | 1203 | >10 |
| Ac-(06-34-18) D-Arg5 | 52 | >10 |
| Ac-(06-34-18) D-Cys2 | 234 | >10 |

TABLE 10

Comparative effects of N-methylation of loop 1 residues and Cys2 on potency and rat plasma stability.

| Peptide | Ki (nM) (human kallikrein) | Observable in rat plasma, for days |
|---|---|---|
| Ac-(06-34-18) wildtype | 0.17 | 2 |
| Ac-(06-34-18) NMeSer1 | 0.5 | 3 |
| Ac-(06-34-18) NMeSer1, NMeAla4 | 444 | >10 |
| Ac-(06-34-18) NMeTrp2 | 228 | 5 |
| Ac-(06-34-18) NMeAla4 | 343 | >10 |
| Ac-(06-34-18) NMeArg5 | 3.5 | >10 |
| Ac-(06-34-18) NMeCys2 | 418 | 10 |

TABLE 11

Comparative effects of arginine analogues in Ac-06-34-18(TMB)-NH2 on potency and stability. Note that the Δ Arg modification did not display any inhibition up to 100 μM peptide.

| Peptide | Ki (nM) (human kallikrein) | Observable in rat plasma, for days |
|---|---|---|
| Ac-(06-34-18) wildtype | 0.17 | 2 |
| Ac-(06-34-18) HomoArg5 | 2.1 | >10 |
| Ac-(06-34-18) Agb5 | 83 | >10 |
| Ac-(06-34-18) Agp5 | 1770 | >10 |
| Ac-(06-34-18) βhomoArg5 | 8.2 | >10 |
| Ac-(06-34-18) 4GuanPhe5 | 0.3 | >10 |
| Ac-(06-34-18) SDMA5 | 1415 | >10 |
| Ac-(06-34-18) NDMA5 | 510 | >10 |
| Ac-(06-34-18) Cit5 | 7860 | >10 |
| Ac-(06-34-18) Δ Arg5 | >100000 | >10 |

TABLE 12

Comparative affinity effects of hydrophobic amino acids substituting Trp2 in Ac-06-34-18(TMB)-NH2

| Peptide | Ki (nM) (human kallikrein) | Observable in rat plasma, for days |
|---|---|---|
| Ac-(06-34-18) wildtype | 0.17 | 2 |
| Ac-(06-34-18) 1NAL2 | 10.7 | 2 |
| Ac-(06-34-18) 2NAL2 | 0.50 | 2 |
| Ac-(06-34-18) 3Pal2 | 59 | 2 |
| Ac-(06-34-18) 4Pal2 | 72 | 2 |
| Ac-(06-34-18) Cha2 | 4.7 | 2 |
| Ac-(06-34-18) 4,4BPal2 | 464 | 2 |
| Ac-(06-34-18) 3,3-DPA2 | 1.5 | 2 |
| Ac-(06-34-18) NorHar2 | 24 | 2 |

TABLE 13

Comparative affinities obtained for proline derivatives with gamma-carbon substituents, analogues of varying ring sizes, bi/tricyclic derivatives, and constrained amino acids such as Aib

| Peptide | Ki (nM) (human kallikrein) | Observable in rat plasma, for days |
|---|---|---|
| Ac-(06-34-18) wildtype | 0.17 | 2 |
| Ac-(06-34-18) HyP3 | 0.41 | 2 |
| Ac-(06-34-18) 4FluoPro3 | 0.24 | 2 |
| Ac-(06-34-18) 4Phenyl Pro3 | 0.58 | 2 |
| Ac-(06-34-18) 4Benzyl Pro3 | 191 | 2 |
| Ac-(06-34-18) Aze3 | 0.06 | 2 |
| Ac-(06-34-18) Pip3 | 0.26 | 2 |
| Ac-(06-34-18) Tic3 | 13.51 | 2 |
| Ac-(06-34-18) NorHar3 | 2.99 | 2 |
| Ac-(06-34-18) Ind3 | 1.35 | 2 |
| Ac-(06-34-18) Aib3 | 1.20 | 2 |

TABLE 14

Comparative effects of miscellaneous substitutions of Ser1, Ala4, and Cys2

| Peptide | Ki (nM) (human kallikrein) | Observable in rat plasma, for days |
|---|---|---|
| Ac-(06-34-18) wildtype | 0.17 | 2 |
| Ac-(06-34-18) Dpg1 | 1.09 | 2 |
| Ac-(06-34-18) Aba4 | 0.07 | 2 |
| Ac-(06-34-18) β-Ala4 | 17450 | 10 |
| Ac-(06-34-18) Aib4 | 289 | 7 |
| Ac-(06-34-18) Cys2ToPen2 | 2162 | 5 |

TABLE 15

Comparative enhancement in potency induced by incorporation of Aze3 in plasma-stabilised candidates.

| Peptide | Ki (nM) (human kallikrein) | Observable in rat plasma, for days[1] | $t_{1/2}$ (hrs) in rat plasma[2] | IC50 (nM) (rat kallikrein)[3] |
|---|---|---|---|---|
| Ac-(06-34-18) wildtype | 0.17 | 2.0 | 2.3 | 1.7 |
| Ac-(06-34-18) HomoArg5 | 2.1 | >10 | 10.7 | 64 |
| Ac-(06-34-18) 4GuanPhe5 | 0.34 | >10 | 2.8 | 21 |
| Ac-(06-34-18) NMeArg5 | 3.5 | >10 | >20 | 98 |
| Ac-(06-34-18) Aze3 HomoArg5 | 0.14 | >10 | nd | nd |
| Ac-(06-34-18) Aze3 4GuanPhe5 | 0.17 | >10 | nd | nd |
| Ac-(06-34-18) Aze3 NMeArg5 | 1.30 | >10 | nd | nd |

[1]Comparative stabilities estimated according to method #1.
[2]The true half-life of peptide stabilities in rat plasma was determined according to method #3.
[3]IC50 values are relative, not absolute.

TABLE 16

Effect on potency upon inclusion of Aba4 in peptides containing Aze3 and the plasma-stabilising modifications NMeArg5, HomoArg5, and 4GuanPhe5.

| Peptide | Ki (nM) (human kallikrein) |
|---|---|
| Ac-(06-34-18) wildtype | 0.17 |
| Ac-(06-34-18) Aze3 Aba4 NMeArg5 | 2.8 |
| Ac-(06-34-18) Aze3 Aba4 HomoArg5 | 0.9 |
| Ac-(06-34-18) Aze3 Aba4 4GuanPhe5 | 0.2 |

TABLE 17

42 unique Kallikrein binders were identified from selections using a randomised WPAR motif at positions 2, 3, 4 & 5 within the 06-34-03 sequence. The sequences were ranked according to Kallikrein binding and the relative abundance in the total selection outputs was noted.

| SEQUENCE | RANK | FREQUENCY | SEQ ID NO: |
|---|---|---|---|
| CSWPARCTHQDLC | 1 | 24 | 67 |
| CSWPSRCTHQDLC | 2 | 51 | 68 |
| CSFPFRCTHQDLC | 3 | 17 | 69 |
| CSWLARCTHQDLC | 4 | 8 | 70 |
| CSFPYRCTHQDLC | 5 | 12 | 71 |
| CSFPFKCTHQDLC | 6 | 4 | 72 |
| CSWAARCTHQDLC | 7 | 1 | 73 |
| CSHPYRCTHQDLC | 8 | 2 | 74 |
| CSHPFRCTHQDLC | 9 | 1 | 75 |
| CSWPYRCTHQDLC | 10 | 3 | 76 |
| CRFPFKCTHQDLC | 11 | 1 | 77 |
| CSFPFRCTHQDLC | 12 | 2 | 78 |
| CSLPFRCTHQDLC | 13 | 3 | 79 |
| CSWPFRCTHQDLC | 14 | 7 | 80 |
| CSFPIRCTHQDLC | 15 | 1 | 81 |
| CSLPFKCTHQDLC | 16 | 1 | 82 |
| CSLPFRCTHQDLC | 17 | 4 | 83 |
| CSYPIRCTHQDLC | 18 | 2 | 84 |
| CSWSARCTHQDLC | 19 | 10 | 85 |
| CSLPFKCTHQDLC | 20 | 1 | 86 |
| CSYPFRCTHQDLC | 21 | 1 | 87 |
| CSFPYKCTHQDLC | 22 | 1 | 88 |
| CSFPWRCTHQDLC | 23 | 1 | 89 |
| CSWHARCTHQDLC | 24 | 1 | 90 |
| CSLPFRCTHQDLC | 25 | 2 | 91 |
| CSYPYRCTHQDLC | 26 | 2 | 92 |
| CSWWARCTHQDLC | 27 | 1 | 93 |
| CSWPYKCTHQDLC | 28 | 1 | 94 |
| CSFLYKCTHQDLC | 29 | 2 | 95 |
| CSLPIRCTHQDLC | 30 | 1 | 96 |
| CSMPYRCTHQDLC | 31 | 2 | 97 |
| CSIPFKCTHQDLC | 32 | 1 | 98 |
| CSYPWRCTHQDLC | 33 | 1 | 99 |
| CSFPFWCTHQDLC | 34 | 1 | 100 |
| CSFSYKCTHQDLC | 35 | 1 | 101 |
| CSWSYRCTHQDLC | 36 | 1 | 102 |
| CSFMYKCTHQDLC | 37 | 1 | 103 |
| CSQVVGCTHQDLC | 38 | 1 | 104 |
| CSWPYHCTHQDLC | 39 | 1 | 105 |
| CSLFDHCTHQDLC | 40 | 1 | 106 |
| CSHRRWCTHQDLC | 41 | 1 | 107 |
| CSWQARCTHQDLC | 42 | 1 | 108 |

TABLE 18

A. Abundance of particular motif in each output. Output sequences were analysed according to the stringency of selection. The % of a particular motif in the output from a particular stringency selection was calculated.

| A | | WPSR | WPAR | WSAR | WPFR | WPYR | FPYR | FPFR |
|---|---|---|---|---|---|---|---|---|
| Stringency | High | 34 | 17 | 3 | 7 | 3 | 7 | 7 |
| | ↑ | 31 | 19 | 3 | 3 | 3 | 3 | 19 |
| | | 41 | 13 | 3 | 0 | 0 | 3 | 9 |
| | | 26 | 22 | 7 | 0 | 4 | 7 | 4 |
| | | 23 | 6 | 6 | 6 | 0 | 16 | 13 |
| | Low | 11 | 4 | 11 | 4 | 0 | 4 | 11 |

TABLE 19

Top 50 Kallikrein binders containing a fixed WPAR motif. The WPAR sequence was fixed in a bicycle library with positions 1, 6, 7, 8, 9 & 10 randomised. Kallikrein selection output sequences were isolated and assayed for Kallikrein binding. The sequences were ranked according to Kallikrein binding. The sequence of peptide 06-34-03 was isolated from selection and is highlighted in red. Trends are visible in the second loop of WPAR-containing Kallikrein-binding peptides.

| RANK | SEQUENCE | BINDING ASSAY SIGNAL | SEQ ID NO: |
|---|---|---|---|
| 1 | CNWPARCTHQDLC | 116 | 109 |
| 2 | CSWPARCTHQDLC | 110 | 87 |
| 3 | CHWPARCTHQDLC | 110 | 110 |
| 4 | CPWPARCTHQDLC | 107 | 111 |
| 5 | CSWPARCTHADLC | 100 | 112 |
| 6 | CSWPARCTHDDLC | 93 | 113 |
| 7 | CAWPARCTHTDLC | 92 | 114 |
| 8 | CQWPARCTHTDLC | 91 | 115 |
| 9 | CLWPARCTHQDLC | 90 | 116 |
| 10 | CTWPARCTHTDLC | 88 | 117 |
| 11 | CHWPARCTHQELC | 85 | 118 |
| 12 | CAWPARCTHDDLC | 84 | 119 |
| 13 | CSWPARCTHTDLC | 83 | 120 |
| 14 | CAWPARCTHVDLC | 82 | 121 |
| 15 | CAWPARCTHTDFC | 80 | 122 |
| 16 | CMWPARCMHQDLC | 79 | 123 |
| 17 | CAWPARCTHADLC | 79 | 124 |
| 18 | CQWPARCMHQDMC | 75 | 125 |
| 19 | CQWPARCTHSDLC | 74 | 126 |
| 20 | CLWPARCTHADLC | 74 | 127 |
| 21 | CRWPARCTHQDLC | 73 | 128 |
| 22 | CQWPARCMHQELC | 73 | 129 |
| 23 | CTWPARCLHQDLC | 73 | 130 |
| 24 | CSWPARCTHSHLC | 72 | 131 |
| 25 | CVWPARCTHQDLC | 71 | 132 |
| 26 | CTWPARCTHADLC | 71 | 133 |
| 27 | CHWPARCMHQDLC | 71 | 134 |
| 28 | CPWPARCTHTDLC | 70 | 135 |
| 29 | CAWPARCTHYDLC | 70 | 136 |
| 30 | CPWPARCTHQNLC | 69 | 137 |
| 31 | CSWPARCTHTELC | 69 | 138 |
| 32 | CAWPARCMHDDLC | 69 | 139 |
| 33 | CSWPARCLHTELC | 68 | 140 |
| 34 | CSWPARCIHQDLC | 68 | 141 |
| 35 | CTWPARCTHTDMC | 67 | 142 |
| 36 | CAWPARCTHTHLC | 66 | 143 |
| 37 | CAWPARCLHADMC | 66 | 144 |
| 38 | CAWPARCLHQDWC | 63 | 145 |
| 39 | CDWPARCMHQEFC | 63 | 146 |
| 40 | CAWPARCTHQTMC | 61 | 147 |
| 41 | CTWPARCLHQHMC | 61 | 148 |
| 42 | CSWPARCVHQDMC | 61 | 149 |
| 43 | CEWPARCLHTDLC | 60 | 150 |
| 44 | CLWPARCLTIELC | 59 | 151 |
| 45 | CSWPARCTHAEMC | 59S | 152 |
| 46 | CRWPARCTHTDLC | 59 | 153 |
| 47 | CTWPARCTHQAFC | 59 | 154 |
| 48 | CSWPARCTHSDLC | 59 | 155 |
| 49 | CSWPARCTHDDLC | 59 | 156 |
| 50 | CPWPARCLHTDLC | 58 | 157 |

TABLE 20

The output sequences from Kallikrein selections with fixed WPAR in the 1st loop, and their associated Kallikrein binding assay signals, were grouped according to their derivation from 'THxxL' motif (A), or 'xHxDL' motif (B). The average binding assay signal for all members of a given group was calculated. Groups containing precisely the given motif are highlighted green; examples of groups with either one more or one less change away from the motif are also shown.

A
Groups based on xHxDL motif

| Motif | Binding | Motif | Binding | Motif | Binding |
|---|---|---|---|---|---|
| THxDL | 78.5 | xHxDL | 70.9 | xHxxL | 56.1 |
| MHxDL | 66.7 | xHxDM | 52.8 | xHxxM | 46.3 |
| LHxDL | 58.0 | xHxEL | 51.7 | xHxxF | 43.8 |
| THxEL | 55.9 | xHxHM | 46.4 | xHxxW | 33.2 |
| THxHL | 52.5 | xHxNL | 46.2 | xTxxL | 31.1 |
| LHxEL | 52.3 | xHxDW | 44.2 | xHxxE | 19.3 |
| THxNL | 51.9 | xHxHL | 44.2 | | |
| THxDW | 44.9 | xHxFL | 40.4 | | |
| LHxDW | 44.7 | xTxEL | 39.9 | | |
| MHxEL | 42.4 | xTxDL | 39.4 | | |
| LTxEL | 39.9 | xHxQL | 39.0 | | |
| LTxDL | 39.4 | xHxAL | 35.5 | | |
| LHxQL | 39.0 | xHxSL | 35.0 | | |
| LHxDM | 38.0 | xTxSL | 33.1 | | |
| LHxSL | 37.4 | xHxYL | 29.2 | | |
| THxAL | 35.5 | | | | |
| LHxHL | 34.0 | | | | |
| LTxSL | 33.1 | | | | |
| THxSL | 28.9 | | | | |

B
Groups based on THxxL motif

| Motif | Binding | Motif | Binding |
|---|---|---|---|
| THxDL | 78.5 | THxxL | 61.0 | MHxxx | 56.5 |
| MHxDL | 66.7 | MHxxL | 55.0 | THxxx | 53.4 |
| LHxDL | 58.0 | LHxxL | 47.9 | LHxxx | 44.4 |
| THxEL | 55.9 | THxxM | 46.3 | LTxxx | 33.8 |
| THxHL | 52.5 | LHxxM | 39.0 | | |
| LHxEL | 52.3 | LTxxL | 38.4 | | |
| THxNL | 51.9 | | | | |
| THxFL | 40.4 | | | | |
| LTxEL | 39.9 | | | | |
| LTxDL | 39.4 | | | | |
| LHxSL | 37.4 | | | | |
| THxAL | 35.5 | | | | |
| LHxHL | 34.0 | | | | |
| LTxSL | 33.1 | | | | |
| THxSL | 28.9 | | | | |

TABLE 21

Affinities and stabilities of WPAR motif variants.

| Peptide | Ki (nM) (human kallikrein) | Observable in rat plasma, for days |
|---|---|---|
| Ac-(06-34-18) WPAR | 0.17 | 2 |
| Ac-(06-34-18) FPAR | 6.28 | 2 |
| Ac-(06-34-18) WPYR | 0.41 | 2 |
| Ac-(06-34-18) WPSR | 0.44 | 2 |
| Ac-(06-34-18) FPYR | 0.46 | 2 |

TABLE 22

Effect of substitutions on Phe2/Tyr4 with hydrophobic analogues

| Peptide | Ki (nM) (human kallikrein) |
|---|---|
| Ac-(06-34-18) Phe2 Tyr4 | 0.46 |
| Ac-(06-34-18) Phe2 Cha4 | 0.91 |
| Ac-(06-34-18) Phe2 3Pal4 | 2.57 |
| Ac-(06-34-18) Phe2 4Pal4 | 2.20 |
| Ac-(06-34-18) Phe2 1Nal4 | 13.5 |
| Ac-(06-34-18) Phe2 2Nal4 | 7.27 |
| Ac-(06-34-18) Phe2 4,4-BPal4 | 10.5 |
| Ac-(06-34-18) 3Pal2 Tyr4 | 0.91 |
| Ac-(06-34-18) 4Pal2 Tyr4 | 3.56 |
| Ac-(06-34-18) Cha2 Tyr4 | 1.87 |

TABLE 23

Summary of the effect of Arg5 substitutions and Aze3 on Ac-06-34-18(TMB)-NH2 Phe2Tyr4.

| Peptide | Ki (nM) (human kallikrein) | Observable in rat plasma, for days[1] | $t_{1/2}$ (hrs) in rat plasma[2] | IC50 (nM) (rat kallikrein)[3] |
|---|---|---|---|---|
| Ac-(06-34-18) Phe2 Tyr4 | 0.46 | 2 | 0.9 | 13.8 |
| Ac-(06-34-18) Phe2 Tyr4 HomoArg5 | 0.77 | >10 | 12.2 | 19.7 |
| Ac-(06-34-18) Phe2 Tyr4 4GuanPhe5 | 0.40 | >10 | 5.0 | 2.5 |
| Ac-(06-34-18) Phe2 Tyr4 NMeArg5 | 3.56 | >10 | >20 | 60.2 |
| Ac-(06-34-18) Phe2 Aze3 Tyr4 HomoArg5 | 0.12 | nd | nd | nd |
| Ac-(06-34-18) Phe2 Aze3Tyr4 4GuanPhe5 | 0.36 | nd | nd | nd |
| Ac-(06-34-18) Phe2 Aze3Tyr4 NMeArg5 | 0.97 | nd | nd | nd |

[1]Comparative stabilities estimated according to method #1.
[2]The true half-life of peptide stabilities in rat plasma was determined according to method #3.
[3]IC50 values are relative, not absolute.

TABLE 24a

Effect of single amino acid substitutions at position 6. The modifications were tested both in the context of Ac-(06-34-18) Phe2 Tyr4 (left column) and Ac-(06-34-18) (right column).

| Residue 6 Modifications | Ki (nM) Ac-(06-34-18) Phe2 Tyr4 | Ki (nM) Ac-(06-34-18) |
|---|---|---|
| Phe6 | 14.90 | nd |
| Ile6 | 1.46 | nd |
| Phg6 | 0.30 | 0.18 |
| tBuGly6 | 3.76 | 0.49 |
| Chg6 | 0.50 | 0.13 |

TABLE 24b

Effect of single amino acid substitutions at position 7. The modifications were tested only in the context of Ac-(06-34-18) Phe2 Tyr4.

| Residue 7 Modifications | Ki (nM) | F (Ki$_{var}$/Ki$_{WT}$) |
|---|---|---|
| Ac-(06-34-18) Phe2 Tyr4 (wild type) | 0.42 | 1 |
| Ac-(06-34-18) Phe2 Tyr4 Phe7 | 43 | 102 |
| Ac-(06-34-18) Phe2 Tyr4 Thi7 | 34 | 80 |
| Ac-(06-34-18) Phe2 Tyr4 4ThiAz7 | 14 | 33 |
| Ac-(06-34-18) Phe2 Tyr4 1,2,4-TriAz7 | 455 | 1084 |
| Ac-(06-34-18) Phe2 Tyr4 4FuAla7 | 17 | 39 |
| Ac-(06-34-18) Phe2 Tyr4 2Pal7 | 53 | 126 |
| Ac-(06-34-18) Phe2 Tyr4 3Pal7 | 130 | 308 |
| Ac-(06-34-18) Phe2 Tyr4 4Pal7 | 79 | 187 |
| Ac-(06-34-18) Phe2 Tyr4 Dap7 | 246 | 586 |
| Ac-(06-34-18) Phe2 Tyr4 Agp7 | 672 | 1599 |
| Ac-(06-34-18) Phe2 Tyr4 Agb7 | 2253 | 5365 |
| Ac-(06-34-18) Phe2 Tyr4 His1Me7 | 10 | 23 |
| Ac-(06-34-18) Phe2 Tyr4 His3Me7 | 292 | 696 |

TABLE 24c

Effect of single amino acid substitutions at position 8. The modifications were tested only in the context of Ac-(06-34-18) Phe2 Tyr4.

| Residue 8 Modifications | Ki (nM) | F (Ki$_{var}$/Ki$_{WT}$) |
|---|---|---|
| Ac-(06-34-18) Phe2 Tyr4 Thr8 | 4.23 | 10 |
| Ac-(06-34-18) Phe2 Tyr4 Thr7 Thr8 Glu9 | 81.02 | 193 |
| Ac-(06-34-18) Phe2 Tyr4 Asp8 | 3.83 | 9 |
| Ac-(06-34-18) Phe2 Tyr4 Glu8 | 2.53 | 6 |
| Ac-(06-34-18) Phe2 Tyr4 Dap8 | 5.49 | 13 |
| Ac-(06-34-18) Phe2 Tyr4 bHGln8 | 16.83 | 40 |

TABLE 25a

α-N-methyl amino acid scan in Loop2. Resultant potencies are compared to WT, and peptide fragments observed after incubation in human plasma are noted.

| N-methyl scan | Ki (nM) | F (Ki$_{var}$/Ki$_{WT}$) | Fragments (human plasma) |
|---|---|---|---|
| Ac-(06-34-18) Phe2 Tyr4 NMe-Leu6 | 57.41 | 137 | -R, -FPYR |
| Ac-(06-34-18) Phe2 Tyr4 NMe-His7 | 63.53 | 151 | -R, -FPYR |
| Ac-(06-34-18) Phe2 Tyr4 NMe-Gln8 | 62.77 | 149 | -R, -FPYR |
| Ac-(06-34-18) Phe2 Tyr4 NMe-Asp9 | 44.29 | 105 | -R, -FPYR |
| Ac-(06-34-18) Phe2 Tyr4 NMe-Leu10 | 586.38 | 1396 | -R, -FPYR |

TABLE 25b

Peptide backbone modifications in Loop2.

| Peptide Backbone Modifications | Ki (nM) | F (Ki$_{var}$/Ki$_{WT}$) |
|---|---|---|
| Ac-(06-34-18) Phe2 Tyr4 N-His7 | 218 | 519 |
| Ac-(06-34-18) Phe2 Tyr4 Ala(ψCH2NH)6 | 1.47 | 4 |

TABLE 26a

Comparative potencies of loop2 plasma protease stability enhanced candidates towards human and rat plasma kallikrein.

| Suitable candidates | Ki (nM) (human kallikrein) | Ki (nM) (rat kallikrein) |
|---|---|---|
| Ac-(06-34-18) Phe2 Tyr4 (wild type) | 0.90 | nd |
| Ac-(06-34-18) Phe2 Tyr4 D-Asp9 | 3.89 | 32.02 |
| Ac-(06-34-18) D-Ala9 | 0.87 | nd |
| Ac-(06-34-18) Phe2 Tyr4 Phg6 | 0.30 | 7.23 |
| Ac-(06-34-18) Phe2 Tyr4 tBuGly6 | 3.76 | 218.50 |
| Ac-(06-34-18) Phe2 Tyr4 Chg6 | 0.50 | 9.09 |
| Ac-(06-34-18) Phe2 Tyr4 Glu8 | 2.53 | nd |
| Ac-(06-34-18) Phe2 Tyr4 Ala(ψCH2NH)6 | 1.47 | 43.56 |

TABLE 26b

Comparative potencies of loop 1 and loop 2-modified 06-34-18 derivatives. Note the inclusion of Aze3 (affinity enhancing) and HArg5 (plasma stability enhancing) modifications in loop 1, and the stability enhancing modifications in loop 2.

| Loop1 and Loop 2 mulitvariants | Ki (nM) (human kallikrein) | Ki (nM) (rat kallikrein) |
|---|---|---|
| Ac-(06-34-18) Phe2 Aze3 Tyr4 HArg5 D-Asp9 | 0.90 | 14 |
| Ac-(06-34-18) Phe2 Aze3 Tyr4 HArg5 Glu8 | 1.65 | 23 |
| Ac-(06-34-18) Phe2 Aze3 Tyr4 HArg5 Ala(ψCH2NH)6 | 0.44 | 41 |
| Ac-(06-34-18) Phe2 Aze3 Tyr4 tBuGly6 | 1.91 | 193 |
| Ac-(06-34-18) Aze3 HArg5 Phg6 | 0.52 | 57 |
| Ac-(06-34-18) Phe2 Aze3 Tyr4 HArg5 Phg6 | 0.32 | 12 |

TABLE 27

Pharmacokinetic parameters of (Ac-(06-34-18) Phe2 Aze3 Tyr4 HArg5 Ala(ψCH2NH)6, Ac-(06-34-18) Phe2 Aze3 Tyr4 HArg5 D-Asp9, and Ac-(06-34-18) All D control in rat. Due to divergent peptide concentrations of Ac-(06-34-18) Phe2 Aze3 Tyr4 HArg5 D-Asp9 in two individual rats, clearance rates and volumes of distribution could not be calculated with confidence.

| Bicyclic Peptide | Clearance based on AUC$_{0-\infty}$ (ml/min/kg) | Volume of distribution based on AUC$_{0-\infty}$ (L/kg) | t$_{1/2\ elimination}$ (min) |
|---|---|---|---|
| (Ac-(06-34-18) Phe2 Aze3 Tyr4 HArg5 Ala(ψCH$_2$NH)6 | 6.2 | 0.44 | 48 |
| Ac-(06-34-18) Phe2 Aze3 Tyr4 HArg5 D-Asp9) | nd | nd | 27 |
| Ac-(06-34-18) All D, control | 4.5 | 0.3 | 54 |

The invention claimed is:

1. A peptide ligand specific for human Kallikrein comprising a polypeptide comprising three reactive groups, separated by two loop sequences, and a molecular scaffold which forms covalent bonds with the reactive groups of the polypeptide such that two polypeptide loops are formed on the molecular scaffold, wherein the loops of the peptide ligand comprise five amino acids and wherein the polypeptide comprises the motif $G_rx_1x_2x_3x_4x_5G_rx_6x_7x_8x_9x_{10}G_r$, wherein $x_1$ and $x_9$ are independently any amino acid, $x_2$ is tryptophan or phenylalanine, $x_3$ is proline or azetidine carboxylic acid, $x_4$ is alanine or tyrosine, $x_5$ is arginine, N-methyl arginine, homoarginine, or guanidylphenylalanine, $x_6$ is tyrosine, leucine or alanine, $x_7$ is histidine, $x_8$ is glutamine or threonine, $x_{10}$ is leucine, and Gr represents cysteine; and wherein the peptide bond between $x_6$ and $x_7$ is replaced by $\Psi CH_2NH$.

2. The peptide ligand according to claim 1, wherein in the first loop $x_3$ is azetidine carboxylic acid; and/or in the first loop $x_5$ is N-methyl arginine or homoarginine or guanidylphenylalanine.

3. The peptide ligand according to claim 2, wherein the polypeptide comprises a first loop which comprises the motif $G_rx_1Fx_3Yx_5G_r$ (SEQ ID NO: 6), wherein $x_3$ is azetidine carboxylic acid and/or $x_5$ is N-methyl arginine or homoarginine or guanidylphenylalanine.

4. The peptide ligand according to claim 1, wherein the molecular scaffold is a tris(bromomethyl)benzene, or a derivative thereof.

5. The peptide ligand according to claim 4, wherein the molecular scaffold is 1,3,5-tris(bromomethyl)-2,4,6-trimethylbenzene, 1,3,5-tris(bromomethyl)benzene, or 1,3,5-tris(bromomethyl)-2,4,6-triethylbenzene.

6. The peptide ligand according to claim 4, wherein the molecular scaffold is 1,3,5-tris(bromomethyl)benzene.

7. The peptide ligand according to claim 1, wherein the peptide ligand is attached to an antibody or a fragment thereof.

8. The peptide ligand according to claim 7, wherein in the first loop $x_3$ is azetidine carboxylic acid; and/or in the first loop $x_5$ is N-methyl arginine or homoarginine or guanidylphenylalanine.

9. The peptide ligand according to claim 7, wherein the polypeptide comprises a first loop which comprises the motif $G_rx_1Fx_3Yx_5G_r$ (SEQ ID NO: 6), wherein $x_3$ is azetidine carboxylic acid and/or $x_5$ is N-methyl arginine or homoarginine or guanidylphenylalanine.

10. The peptide ligand according to claim 7, wherein the peptide ligand comprises: Cys Ser1 Phe 2 Aze3 Tyr4 HArg5 Cys Ala($\Psi CH_2NH$)6 His7 Gln8 Asp9 Leu10 Cys (SEQ ID NO: 201).

11. The peptide ligand according to claim 7, wherein the antibody fragment is selected from an antibody light chain constant region (CL), an antibody CH1 heavy chain domain, an antibody CH2 heavy chain domain, an antibody CH3 heavy chain domain, or any combination thereof, in addition to the one or more constant region domains.

12. The peptide ligand according to claim 7, wherein the antibody or fragment thereof comprises a hinge region of an antibody.

13. The peptide ligand according to claim 12, wherein the hinge region comprises the region between the CH1 and CH2 domains of an IgG molecule.

14. The peptide ligand according to claim 7, wherein the antibody or fragment thereof comprises an Fc region of an IgG molecule.

15. The peptide ligand according to claim 7, wherein the peptide ligand comprises:

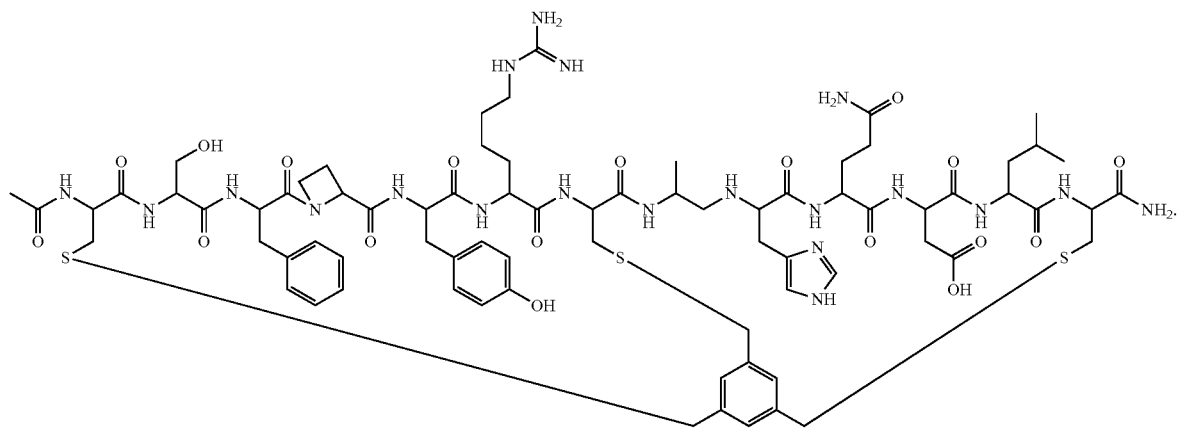 [SMILES: CC(=O)NC1CSCc2cc3cc(c2)CSCC(NC(=O)C(CCCCNC(=N)N)NC(=O)C(Cc2ccc(O)cc2)NC(=O)C2CCN2C(=O)C(Cc2ccccc2)NC(=O)C(CO)NC1=O)C(=O)NC(C)CNC(Cc1c[nH]cn1)C(=O)NC(CCC(N)=O)C(=O)NC(CC(=O)O)C(=O)NC(CC(C)C)C(=O)NC(C(N)=O)CSC3]

16. The peptide ligand according to claim 15, wherein the peptide ligand is attached to an antibody or a fragment thereof, wherein the antibody fragment is selected from an antibody light chain constant region (CL), an antibody CH1 heavy chain domain, an antibody CH2 heavy chain domain, an antibody CH3 heavy chain domain, or any combination thereof, in addition to the one or more constant region domains.

17. The peptide ligand according to claim 15, wherein the peptide ligand is attached to an antibody or a fragment thereof, which comprises a hinge region of an antibody.

18. The peptide ligand according to claim 17, wherein the hinge region comprises the region between the CH1 and CH2 domains of an IgG molecule.

19. The peptide ligand according to claim 15, wherein the peptide ligand is attached to an antibody or a fragment thereof, which comprises an Fc region of an IgG molecule.

20. A pharmaceutical composition comprising the peptide ligand according to claim 1 and a pharmacologically appropriate carrier.

21. A pharmaceutical composition comprising the peptide ligand according to claim 7 and a pharmacologically appropriate carrier.

* * * * *

UNITED STATES PATENT AND TRADEMARK OFFICE
CERTIFICATE OF CORRECTION

| | |
|---|---|
| PATENT NO. | : 10,870,679 B2 |
| APPLICATION NO. | : 16/013795 |
| DATED | : December 22, 2020 |
| INVENTOR(S) | : Daniel Teufel et al. |

It is certified that error appears in the above-identified patent and that said Letters Patent is hereby corrected as shown below:

On the Title Page

Item (71) Replace Applicant name from "BicyleRD Limited" to "BicycleRD Limited"

Signed and Sealed this
Eleventh Day of July, 2023

Katherine Kelly Vidal
*Director of the United States Patent and Trademark Office*

SEQUENCE LISTING

<160> NUMBER OF SEQ ID NOS: 222

<210> SEQ ID NO 1
<211> LENGTH: 17
<212> TYPE: PRT
<213> ORGANISM: Artificial sequence

```
<220> FEATURE:
<223> OTHER INFORMATION: Synthetic peptide PK2

<400> SEQUENCE: 1

Ala Cys Ser Asp Arg Phe Arg Asn Cys Pro Leu Trp Ser Gly Thr Cys
1               5                   10                  15

Gly

<210> SEQ ID NO 2
<211> LENGTH: 17
<212> TYPE: PRT
<213> ORGANISM: Artificial sequence
<220> FEATURE:
<223> OTHER INFORMATION: Synthetic peptide PK15

<400> SEQUENCE: 2

Ala Cys Ser Asp Arg Phe Arg Asn Cys Pro Ala Asp Glu Ala Leu Cys
1               5                   10                  15

Gly

<210> SEQ ID NO 3
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(4)
<223> OTHER INFORMATION: Xaa is Proline or Azetine Carboxylic Acid
<220> FEATURE:
<221> NAME/KEY: VARIANT
<222> LOCATION: (6)..(6)
<223> OTHER INFORMATION: Xaa is Arginine, N-methyl Arginine,
      Homoarginine, or guanidylphenylalanine
<220> FEATURE:
<221> NAME/KEY: VARIANT
<222> LOCATION: (7)..(7)
<223> OTHER INFORMATION: Xaa is any amino acid

<400> SEQUENCE: 3

Xaa Xaa Trp Xaa Ala Xaa Xaa
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (7)..(7)
<223> OTHER INFORMATION: Xaa is any amino acid
```

```
<400> SEQUENCE: 4

Xaa Xaa Trp Pro Ser Arg Xaa
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (7)..(7)
<223> OTHER INFORMATION: Xaa is any amino acid

<400> SEQUENCE: 5

Xaa Xaa Phe Pro Phe Arg Xaa
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(4)
<223> OTHER INFORMATION: Xaa is Proline or Azetine Carboxylic Acid
<220> FEATURE:
<221> NAME/KEY: VARIANT
<222> LOCATION: (6)..(6)
<223> OTHER INFORMATION: Xaa is Arginine, N-methyl Arginine,
      Homoarginine, or guanidylphenylalanine
<220> FEATURE:
<221> NAME/KEY: VARIANT
<222> LOCATION: (7)..(7)
<223> OTHER INFORMATION: Xaa is any amino acid

<400> SEQUENCE: 6

Xaa Xaa Phe Xaa Tyr Xaa Xaa
1               5

<210> SEQ ID NO 7
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION
```

<400> SEQUENCE: 7

Cys Ser Trp Pro Ala Arg Cys Leu His Gln Asp Leu Cys
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 8

Cys Ser Phe Pro Tyr Arg Cys Leu His Gln Asp Leu Cys
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetic peptide motif
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (3)..(3)
<223> OTHER INFORMATION: Xaa is Trp or Phe
<220> FEATURE:
<221> NAME/KEY: VARIANT
<222> LOCATION: (5)..(5)
<223> OTHER INFORMATION: Xaa is any amino acid
<220> FEATURE:
<221> NAME/KEY: VARIANT
<222> LOCATION: (6)..(6)
<223> OTHER INFORMATION: Xaa is Lys or Arg
<220> FEATURE:
<221> NAME/KEY: VARIANT
<222> LOCATION: (7)..(7)
<223> OTHER INFORMATION: Xaa is Cys, Lys, Asp, Glu, Arg, Tyr, Ser, or
      selenocysteine
<220> FEATURE:
<221> NAME/KEY: VARIANT
<222> LOCATION: (8)..(8)
<223> OTHER INFORMATION: Xaa is Thr or Leu
<220> FEATURE:
<221> NAME/KEY: VARIANT
<222> LOCATION: (10)..(10)
<223> OTHER INFORMATION: Xaa is Gln or Thr
<220> FEATURE:
<221> NAME/KEY: VARIANT
<222> LOCATION: (13)..(13)
<223> OTHER INFORMATION: Xaa is any amino acid

<400> SEQUENCE: 9

Xaa Xaa Xaa Pro Xaa Xaa Xaa Xaa His Xaa Asp Leu Xaa
1               5                   10

<210> SEQ ID NO 10

```
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: VARIANT
<222> LOCATION: (3)..(8)
<223> OTHER INFORMATION: Xaa at positions 3-8 stands for a random
      natural amino acid and up to three of them may be absent;
      represents a range of between 3 and 6 amino acids.
<220> FEATURE:
<221> NAME/KEY: VARIANT
<222> LOCATION: (10)..(15)
<223> OTHER INFORMATION: Xaa at positions 10-15 stands for a random
      natural amino acid and up to three of them may be absent;
      represents a range of between 3 and 6 amino acids.

<400> SEQUENCE: 10

Ala Cys Xaa Xaa Xaa Xaa Xaa Xaa Cys Xaa Xaa Xaa Xaa Xaa Xaa Cys
1               5                   10                  15

Gly

<210> SEQ ID NO 11
<211> LENGTH: 4
<212> TYPE: PRT
<213> ORGANISM: Artificial sequence
<220> FEATURE:
<223> OTHER INFORMATION: Synthetic peptide linker

<400> SEQUENCE: 11

Gly Gly Ser Gly
1

<210> SEQ ID NO 12
<211> LENGTH: 32
<212> TYPE: DNA
<213> ORGANISM: Artificial sequence
<220> FEATURE:
<223> OTHER INFORMATION: Primer

<400> SEQUENCE: 12
ggcggttctg gcgctgaaac tgttgaaagt ag                                   32

<210> SEQ ID NO 13
<211> LENGTH: 41
<212> TYPE: DNA
<213> ORGANISM: Artificial sequence
<220> FEATURE:
<223> OTHER INFORMATION: Primer

<400> SEQUENCE: 13
gaagccatgg cccccgaggc cccggacgga gcattgacag g                         41

<210> SEQ ID NO 14
<211> LENGTH: 77
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
```

```
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 14
tatgcggccc agccggccat ggcannktgt nnknnknnkt gcnnknnknn knnktgtnnk    60
gggcggttct ggcgctg                                                  77

<210> SEQ ID NO 15
<211> LENGTH: 13
<212> TYPE: PRT
<213> ORGANISM: Artificial sequence
<220> FEATURE:
<223> OTHER INFORMATION: Synthetic sequence: Semi-random peptide for a
      3x3 library
<220> FEATURE:
<221> NAME/KEY: VARIANT
<222> LOCATION: (6)..(8)
<223> OTHER INFORMATION: Xaa is any amino acid
<220> FEATURE:
<221> NAME/KEY: VARIANT
<222> LOCATION: (10)..(12)
<223> OTHER INFORMATION: Xaa is any amino acid

<400> SEQUENCE: 15

Pro Ala Met Ala Cys Xaa Xaa Xaa Cys Xaa Xaa Xaa Cys
1               5                   10

<210> SEQ ID NO 16
<211> LENGTH: 67
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
```

```
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 16
tatgcggccc agccggccat ggcatgtnnk nnknnktgcn nknnknnktg tggcggttct      60
ggcgctg                                                                67

<210> SEQ ID NO 17
<211> LENGTH: 7
<212> TYPE: PRT
<213> ORGANISM: Artificial sequence
<220> FEATURE:
<223> OTHER INFORMATION: Peptide motif
<220> FEATURE:
<221> NAME/KEY: VARIANT
<222> LOCATION: (2)..(2)
<223> OTHER INFORMATION: Xaa is any amino acid

<400> SEQUENCE: 17

Cys Xaa Trp Pro Ala Arg Cys
1               5

<210> SEQ ID NO 18
<211> LENGTH: 8
<212> TYPE: PRT
<213> ORGANISM: Artificial sequence
<220> FEATURE:
<223> OTHER INFORMATION: Peptide motif
<220> FEATURE:
<221> NAME/KEY: VARIANT
<222> LOCATION: (4)..(5)
<223> OTHER INFORMATION: Xaa is any amino acid

<400> SEQUENCE: 18

Cys Gly Gly Xaa Xaa Asn Cys Arg
1               5

<210> SEQ ID NO 19
<211> LENGTH: 4
<212> TYPE: PRT
<213> ORGANISM: Artificial sequence
<220> FEATURE:
<223> OTHER INFORMATION: Peptide motif

<400> SEQUENCE: 19

Trp Pro Ala Arg
1

<210> SEQ ID NO 20
<211> LENGTH: 4
<212> TYPE: PRT
<213> ORGANISM: Artificial sequence
<220> FEATURE:
<223> OTHER INFORMATION: Peptide motif

<400> SEQUENCE: 20

Trp Pro Ser Arg
1

<210> SEQ ID NO 21
<211> LENGTH: 4
<212> TYPE: PRT
<213> ORGANISM: Artificial sequence
```

```
<220> FEATURE:
<223> OTHER INFORMATION: Peptide motif

<400> SEQUENCE: 21

Trp Ser Ala Arg
1

<210> SEQ ID NO 22
<211> LENGTH: 4
<212> TYPE: PRT
<213> ORGANISM: Artificial sequence
<220> FEATURE:
<223> OTHER INFORMATION: Peptide motif

<400> SEQUENCE: 22

Trp Pro Phe Arg
1

<210> SEQ ID NO 23
<211> LENGTH: 4
<212> TYPE: PRT
<213> ORGANISM: Artificial sequence
<220> FEATURE:
<223> OTHER INFORMATION: Peptide motif

<400> SEQUENCE: 23

Trp Pro Tyr Arg
1

<210> SEQ ID NO 24
<211> LENGTH: 4
<212> TYPE: PRT
<213> ORGANISM: Artificial sequence
<220> FEATURE:
<223> OTHER INFORMATION: Peptide motif

<400> SEQUENCE: 24

Phe Pro Phe Arg
1

<210> SEQ ID NO 25
<211> LENGTH: 4
<212> TYPE: PRT
<213> ORGANISM: Artificial sequence
<220> FEATURE:
<223> OTHER INFORMATION: Peptide motif

<400> SEQUENCE: 25

Phe Pro Tyr Arg
1

<210> SEQ ID NO 26
<211> LENGTH: 13
<212> TYPE: PRT
<213> ORGANISM: Artificial sequence
<220> FEATURE:
<223> OTHER INFORMATION: Synthetic peptide: Phage library with a fixed-
      WPAR sequence and all other positions randomised
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (8)..(12)
<223> OTHER INFORMATION: Xaa is any amino acid

<400> SEQUENCE: 26
```

Cys Xaa Trp Pro Ala Arg Cys Xaa Xaa Xaa Xaa Xaa Cys
1               5                   10

<210> SEQ ID NO 27
<211> LENGTH: 13
<212> TYPE: PRT
<213> ORGANISM: Artificial sequence
<220> FEATURE:
<223> OTHER INFORMATION: Peptide motif
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (8)..(8)
<223> OTHER INFORMATION: Xaa is Thr or Leu
<220> FEATURE:
<221> NAME/KEY: VARIANT
<222> LOCATION: (10)..(10)
<223> OTHER INFORMATION: Xaa is Gln or Thr

<400> SEQUENCE: 27

Cys Xaa Trp Pro Ala Arg Cys Xaa His Xaa Asp Leu Cys
1               5                   10

<210> SEQ ID NO 28
<211> LENGTH: 13
<212> TYPE: PRT
<213> ORGANISM: Artificial sequence
<220> FEATURE:
<223> OTHER INFORMATION: Peptide motif
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (10)..(10)
<223> OTHER INFORMATION: Xaa is Gln or Thr

<400> SEQUENCE: 28

Cys Xaa Trp Pro Ala Arg Cys Thr His Xaa Asp Leu Cys
1               5                   10

<210> SEQ ID NO 29
<211> LENGTH: 5
<212> TYPE: PRT
<213> ORGANISM: Artificial sequence
<220> FEATURE:
<223> OTHER INFORMATION: Peptide motif
<220> FEATURE:
<221> NAME/KEY: VARIANT
<222> LOCATION: (3)..(3)
<223> OTHER INFORMATION: Xaa is any amino acid

<400> SEQUENCE: 29

Thr His Xaa Asp Leu
1               5

<210> SEQ ID NO 30
<211> LENGTH: 5
<212> TYPE: PRT
<213> ORGANISM: Artificial sequence
<220> FEATURE:
<223> OTHER INFORMATION: Peptide motif

<400> SEQUENCE: 30

Thr His Gln Asp Leu
1               5

```
<210> SEQ ID NO 31
<211> LENGTH: 4
<212> TYPE: PRT
<213> ORGANISM: Artificial sequence
<220> FEATURE:
<223> OTHER INFORMATION: Peptide motif

<400> SEQUENCE: 31

Phe Pro Ala Arg
1

<210> SEQ ID NO 32
<211> LENGTH: 5
<212> TYPE: PRT
<213> ORGANISM: Artificial sequence
<220> FEATURE:
<223> OTHER INFORMATION: Synthetic peptide

<400> SEQUENCE: 32

Leu Thr Thr Glu Leu
1               5

<210> SEQ ID NO 33
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 33

Ala Cys Ala Trp Pro Ala Arg Cys Leu Thr Val Asp Leu Cys Ala
1               5                   10                  15

<210> SEQ ID NO 34
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 34

Ala Cys Arg Trp Pro Ala Arg Cys Val His Gln Asp Leu Cys Ala
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 35

Ala Cys Ser Trp Pro Ala Arg Cys Asn His Gln Asp Leu Cys Ala
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 36
```

Ala Cys Arg Trp Pro Ala Arg Cys Leu Thr Thr Ser Leu Cys Ala
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 37

Ala Cys Arg Trp Pro Ala Arg Cys Thr His Gln Asn Tyr Cys Ala
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 38

Ala Cys Thr Trp Pro Ala Arg Cys Thr His Gln Asn Trp Cys Ala
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 39

Ala Cys Phe Pro Ser His Asp Cys Asp Gly Arg Arg Met Cys Ala
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 40

Ala Cys Gly Gly Pro Gln Asn Cys Arg Thr Trp Thr Thr Cys Ala
1               5                   10                  15

<210> SEQ ID NO 41
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 41

Ala Cys Asn Trp Pro Tyr Arg Cys Leu His Thr Asp Leu Cys Ala
1               5                   10                  15

<210> SEQ ID NO 42
<211> LENGTH: 15
<212> TYPE: PRT
<213> ORGANISM: Artificial sequence
<220> FEATURE:

```
<223> OTHER INFORMATION: Synthetic sequence: Bicyclic peptide from 5x5
      library

<400> SEQUENCE: 42

Ala Cys Ser Trp Pro Tyr Arg Cys Leu His Gln Asp Tyr Cys Ala
1               5                   10                  15

<210> SEQ ID NO 43
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 43

Ala Cys Gly Val Pro Tyr Arg Cys Thr His Gln Glu Met Cys Ala
1               5                   10                  15

<210> SEQ ID NO 44
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 44

Ala Cys Thr Trp Pro Ala Arg Cys Thr Met Gln Asn Trp Cys Ala
1               5                   10                  15

<210> SEQ ID NO 45
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 45

Ala Cys Ala Asp Pro Trp Ala Cys Leu Phe Arg Arg Pro Cys Ala
1               5                   10                  15

<210> SEQ ID NO 46
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 46

Ala Cys Ala Trp Pro Ala Arg Cys Leu Thr Thr Ser Leu Cys Gly
1               5                   10                  15

<210> SEQ ID NO 47
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 47

Ala Cys Thr Tyr Pro Tyr Lys Cys Leu His Gln Asn Leu Cys Ala
1               5                   10                  15
```

```
<210> SEQ ID NO 48
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 48

Ala Cys Ala Trp Pro Ala Lys Cys Leu Thr Arg Glu Leu Cys Ala
1               5                   10                  15

<210> SEQ ID NO 49
<211> LENGTH: 15
<212> TYPE: PRT
<213> ORGANISM: Artificial sequence
<220> FEATURE:
<223> OTHER INFORMATION: Synthetic sequence: Bicyclic peptide from 5x5
      library

<400> SEQUENCE: 49

Ala Cys Gly Gly Tyr Asn Asn Cys Arg Ala Phe Ser Tyr Cys Ala
1               5                   10                  15

<210> SEQ ID NO 50
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 50

Ala Cys Ser Trp Pro Ala Arg Cys Val His Gln Asp Leu Cys Ala
1               5                   10                  15

<210> SEQ ID NO 51
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 51

Ala Cys Arg Trp Pro Ala Arg Cys Thr His Gln Asp Leu Cys Ala
1               5                   10                  15

<210> SEQ ID NO 52
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 52

Ala Cys Ser Trp Pro Ala Arg Cys Thr His Gln Asp Leu Cys Ala
1               5                   10                  15

<210> SEQ ID NO 53
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 53
```

```
Ala Cys Arg Trp Pro Ala Arg Cys Met His Gln Asp Leu Cys Ala
1               5                   10                  15

<210> SEQ ID NO 54
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 54

Ala Cys Arg Trp Pro Ala Arg Cys Leu His Gln Asp Leu Cys Ala
1               5                   10                  15

<210> SEQ ID NO 55
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 55

Ala Cys Ser Trp Pro Ala Arg Cys Met His Gln Asp Leu Cys Ala
1               5                   10                  15

<210> SEQ ID NO 56
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 56

Ala Cys Ser Trp Pro Ala Arg Cys Leu His Gln Asp Leu Cys Ala
1               5                   10                  15

<210> SEQ ID NO 57
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 57

Ala Cys Ser Trp Pro Ala Lys Cys Leu His Gln Asp Leu Cys Ala
1               5                   10                  15

<210> SEQ ID NO 58
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)

<400> SEQUENCE: 58

Ala Cys Ala Trp Pro Ala Arg Cys Ala His Gln Asp Leu Cys Ala
1               5                   10                  15

<210> SEQ ID NO 59
<211> LENGTH: 15
<212> TYPE: PRT
<213> ORGANISM: Artificial sequence
```

```
<220> FEATURE:
<223> OTHER INFORMATION: Synthetic sequence: Variant of peptide 06-34 of
      PCT/EP2014/057440 (SEQ ID NO: 34)
<220> FEATURE:
<221> NAME/KEY: MOD_RES
<222> LOCATION: (3)..(3)
<223> OTHER INFORMATION: MeGly
<220> FEATURE:
<221> NAME/KEY: MOD_RES
<222> LOCATION: (9)..(9)
<223> OTHER INFORMATION: MeGly

<400> SEQUENCE: 59

Ala Cys Gly Trp Pro Ala Arg Cys Gly His Gln Asp Leu Cys Ala
1               5                   10                  15

<210> SEQ ID NO 60
<211> LENGTH: 15
<212> TYPE: PRT
<213> ORGANISM: Artificial sequence
<220> FEATURE:
<223> OTHER INFORMATION: Synthetic sequence: Variant of peptide 06-34 of
      PCT/EP2014/057440 (SEQ ID NO: 34)
<220> FEATURE:
<221> NAME/KEY: SITE
<222> LOCATION: (3)..(3)
<223> OTHER INFORMATION: Xaa is N-MeSer

<400> SEQUENCE: 60

Ala Cys Xaa Trp Pro Ala Arg Cys Leu His Gln Asp Leu Cys Ala
1               5                   10                  15

<210> SEQ ID NO 61
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative
<220> FEATURE:
<221> NAME/KEY: MOD_RES
<222> LOCATION: (1)..(1)
<223> OTHER INFORMATION: ACETYLATION

<400> SEQUENCE: 61

Cys Ser Ala Ala Ala Arg Cys Leu His Gln Asp Leu Cys
1               5                   10

<210> SEQ ID NO 62
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative
<220> FEATURE:
<221> NAME/KEY: MOD_RES
<222> LOCATION: (1)..(1)
<223> OTHER INFORMATION: ACETYLATION

<400> SEQUENCE: 62

Cys Ser Ala Gln Ala Arg Cys Leu His Gln Asp Leu Cys
1               5                   10

<210> SEQ ID NO 63
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative
```

```
<220> FEATURE:
<221> NAME/KEY: MOD_RES
<222> LOCATION: (1)..(1)
<223> OTHER INFORMATION: ACETYLATION

<400> SEQUENCE: 63

Cys Pro Ser Ala Trp Arg Cys Leu His Gln Asp Leu Cys
1               5                   10

<210> SEQ ID NO 64
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative
<220> FEATURE:
<221> NAME/KEY: MOD_RES
<222> LOCATION: (1)..(1)
<223> OTHER INFORMATION: ACETYLATION

<400> SEQUENCE: 64

Cys Trp Ala Ser Pro Arg Cys Leu His Gln Asp Leu Cys
1               5                   10

<210> SEQ ID NO 65
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative
<220> FEATURE:
<221> NAME/KEY: MOD_RES
<222> LOCATION: (1)..(1)
<223> OTHER INFORMATION: ACETYLATION

<400> SEQUENCE: 65

Cys Ala Pro Trp Ser Arg Cys Leu His Gln Asp Leu Cys
1               5                   10

<210> SEQ ID NO 66
<211> LENGTH: 13
<212> TYPE: PRT
<213> ORGANISM: Artificial sequence
<220> FEATURE:
<223> OTHER INFORMATION: Synthetic sequence: Ac-06-34-18(TMB)-NH2
      derivative
<220> FEATURE:
<221> NAME/KEY: MOD_RES
<222> LOCATION: (1)..(1)
<223> OTHER INFORMATION: ACETYLATION

<400> SEQUENCE: 66

Cys Trp Ala Arg Ser Pro Cys Leu His Gln Asp Leu Cys
1               5                   10

<210> SEQ ID NO 67
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 67

Cys Ser Trp Pro Ala Arg Cys Thr His Gln Asp Leu Cys
1               5                   10
```

<210> SEQ ID NO 68
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 68

Cys Ser Trp Pro Ser Arg Cys Thr His Gln Asp Leu Cys
1               5                   10

<210> SEQ ID NO 69
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 69

Cys Ser Phe Pro Phe Arg Cys Thr His Gln Asp Leu Cys
1               5                   10

<210> SEQ ID NO 70
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 70

Cys Ser Trp Leu Ala Arg Cys Thr His Gln Asp Leu Cys
1               5                   10

<210> SEQ ID NO 71
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 71

Cys Ser Phe Pro Tyr Arg Cys Thr His Gln Asp Leu Cys
1               5                   10

<210> SEQ ID NO 72
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 72

Cys Ser Phe Pro Phe Lys Cys Thr His Gln Asp Leu Cys
1               5                   10

<210> SEQ ID NO 73
<211> LENGTH: 13
<212> TYPE: PRT

-continued

<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 73

Cys Ser Trp Ala Ala Arg Cys Thr His Gln Asp Leu Cys
1               5                   10

<210> SEQ ID NO 74
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 74

Cys Ser His Pro Tyr Arg Cys Thr His Gln Asp Leu Cys
1               5                   10

<210> SEQ ID NO 75
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 75

Cys Ser His Pro Phe Arg Cys Thr His Gln Asp Leu Cys
1               5                   10

<210> SEQ ID NO 76
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 76

Cys Ser Trp Pro Tyr Arg Cys Thr His Gln Asp Leu Cys
1               5                   10

<210> SEQ ID NO 77
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 77

Cys Arg Phe Pro Phe Lys Cys Thr His Gln Asp Leu Cys
1               5                   10

<210> SEQ ID NO 78
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at positions 2, 3, 4 & 5 within the 06-34-03 sequence

<400> SEQUENCE: 78

Cys Ser Phe Pro Phe Arg Cys Thr His Gln Asp Leu Cys
1               5                   10

<210> SEQ ID NO 79
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 79

Cys Ser Leu Pro Phe Arg Cys Thr His Gln Asp Leu Cys
1               5                   10

<210> SEQ ID NO 80
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 80

Cys Ser Trp Pro Phe Arg Cys Thr His Gln Asp Leu Cys
1               5                   10

<210> SEQ ID NO 81
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 81

Cys Ser Phe Pro Ile Arg Cys Thr His Gln Asp Leu Cys
1               5                   10

<210> SEQ ID NO 82
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 82

Cys Ser Leu Pro Phe Lys Cys Thr His Gln Asp Leu Cys
1               5                   10

<210> SEQ ID NO 83
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 83

-continued

Cys Ser Leu Pro Phe Arg Cys Thr His Gln Asp Leu Cys
1               5                   10

<210> SEQ ID NO 84
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 84

Cys Ser Tyr Pro Ile Arg Cys Thr His Gln Asp Leu Cys
1               5                   10

<210> SEQ ID NO 85
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 85

Cys Ser Trp Ser Ala Arg Cys Thr His Gln Asp Leu Cys
1               5                   10

<210> SEQ ID NO 86
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 86

Cys Ser Leu Pro Phe Lys Cys Thr His Gln Asp Leu Cys
1               5                   10

<210> SEQ ID NO 87
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 87

Cys Ser Tyr Pro Phe Arg Cys Thr His Gln Asp Leu Cys
1               5                   10

<210> SEQ ID NO 88
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the
      06-34-03 sequence

<400> SEQUENCE: 88

Cys Ser Phe Pro Tyr Lys Cys Thr His Gln Asp Leu Cys
1               5                   10

<210> SEQ ID NO 89
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 89

Cys Ser Phe Pro Trp Arg Cys Thr His Gln Asp Leu Cys
1               5                   10

<210> SEQ ID NO 90
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 90

Cys Ser Trp His Ala Arg Cys Thr His Gln Asp Leu Cys
1               5                   10

<210> SEQ ID NO 91
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 91

Cys Ser Leu Pro Phe Arg Cys Thr His Gln Asp Leu Cys
1               5                   10

<210> SEQ ID NO 92
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 92

Cys Ser Tyr Pro Tyr Arg Cys Thr His Gln Asp Leu Cys
1               5                   10

<210> SEQ ID NO 93
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 93

Cys Ser Trp Trp Ala Arg Cys Thr His Gln Asp Leu Cys
1               5                   10

<210> SEQ ID NO 94
<211> LENGTH: 13
<212> TYPE: PRT

```
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 94

Cys Ser Trp Pro Tyr Lys Cys Thr His Gln Asp Leu Cys
1               5                   10

<210> SEQ ID NO 95
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 95

Cys Ser Phe Leu Tyr Lys Cys Thr His Gln Asp Leu Cys
1               5                   10

<210> SEQ ID NO 96
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 96

Cys Ser Leu Pro Ile Arg Cys Thr His Gln Asp Leu Cys
1               5                   10

<210> SEQ ID NO 97
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 97

Cys Ser Met Pro Tyr Arg Cys Thr His Gln Asp Leu Cys
1               5                   10

<210> SEQ ID NO 98
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 98

Cys Ser Ile Pro Phe Lys Cys Thr His Gln Asp Leu Cys
1               5                   10

<210> SEQ ID NO 99
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
``` positions 2, 3, 4 & 5 within the 06-34-03 sequence

<400> SEQUENCE: 99

Cys Ser Tyr Pro Trp Arg Cys Thr His Gln Asp Leu Cys
1               5                   10

<210> SEQ ID NO 100
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 100

Cys Ser Phe Pro Phe Trp Cys Thr His Gln Asp Leu Cys
1               5                   10

<210> SEQ ID NO 101
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 101

Cys Ser Phe Ser Tyr Lys Cys Thr His Gln Asp Leu Cys
1               5                   10

<210> SEQ ID NO 102
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 102

Cys Ser Trp Ser Tyr Arg Cys Thr His Gln Asp Leu Cys
1               5                   10

<210> SEQ ID NO 103
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 103

Cys Ser Phe Met Tyr Lys Cys Thr His Gln Asp Leu Cys
1               5                   10

<210> SEQ ID NO 104
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 104

Cys Ser Gln Val Val Gly Cys Thr His Gln Asp Leu Cys
1               5                   10

<210> SEQ ID NO 105
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 105

Cys Arg Trp Pro Tyr His Cys Thr His Gln Asp Leu Cys
1               5                   10

<210> SEQ ID NO 106
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 106

Cys Ser Leu Phe Asp His Cys Thr His Gln Asp Leu Cys
1               5                   10

<210> SEQ ID NO 107
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 107

Cys Ser His Arg Arg Trp Cys Thr His Gln Asp Leu Cys
1               5                   10

<210> SEQ ID NO 108
<211> LENGTH: 13
<212> TYPE: PRT
<213> ORGANISM: Artificial sequence
<220> FEATURE:
<223> OTHER INFORMATION: Synthetic sequence: Kallikrein binder
      identified from selections using a randomised WPAR motif at
      positions 2, 3, 4 & 5 within the 06-34-03 sequence

<400> SEQUENCE: 108

Cys Ser Trp Gln Ala Arg Cys Thr His Gln Asp Leu Cys
1               5                   10

<210> SEQ ID NO 109
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 109

Cys Asn Trp Pro Ala Arg Cys Thr His Gln Asp Leu Cys
1               5                   10

<210> SEQ ID NO 110

```
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 110

Cys His Trp Pro Ala Arg Cys Thr His Gln Asp Leu Cys
1               5                   10

<210> SEQ ID NO 111
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 111

Cys Pro Trp Pro Ala Arg Cys Thr His Gln Asp Leu Cys
1               5                   10

<210> SEQ ID NO 112
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 112

Cys Ser Trp Pro Ala Arg Cys Thr His Ala Asp Leu Cys
1               5                   10

<210> SEQ ID NO 113
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 113

Cys Ser Trp Pro Ala Arg Cys Thr His Asp Asp Leu Cys
1               5                   10

<210> SEQ ID NO 114
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 114

Cys Ala Trp Pro Ala Arg Cys Thr His Thr Asp Leu Cys
1               5                   10

<210> SEQ ID NO 115
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 115
```

Cys Gln Trp Pro Ala Arg Cys Leu His Thr Asp Leu Cys
1               5                   10

<210> SEQ ID NO 116
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 116

Cys Leu Trp Pro Ala Arg Cys Thr His Gln Asp Leu Cys
1               5                   10

<210> SEQ ID NO 117
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 117

Cys Thr Trp Pro Ala Arg Cys Thr His Thr Asp Leu Cys
1               5                   10

<210> SEQ ID NO 118
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 118

Cys His Trp Pro Ala Arg Cys Thr His Gln Glu Leu Cys
1               5                   10

<210> SEQ ID NO 119
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 119

Cys Ala Trp Pro Ala Arg Cys Leu His Asp Asp Leu Cys
1               5                   10

<210> SEQ ID NO 120
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 120

Cys Ser Trp Pro Ala Arg Cys Leu His Thr Asp Leu Cys
1               5                   10

<210> SEQ ID NO 121
<211> LENGTH: 13
<212> TYPE: PRT
<213> ORGANISM: Artificial sequence
<220> FEATURE:

<223> OTHER INFORMATION: Synthetic sequence: Kallikrein binder
    containing a WPAR motif

<400> SEQUENCE: 121

Cys Ala Trp Pro Ala Arg Cys Thr His Val Asp Leu Cys
1               5                   10

<210> SEQ ID NO 122
<211> LENGTH: 13
<212> TYPE: PRT
<213> ORGANISM: Artificial sequence
<220> FEATURE:
<223> OTHER INFORMATION: Synthetic sequence: Kallikrein binder
    containing a WPAR motif

<400> SEQUENCE: 122

Cys Ala Trp Pro Ala Arg Cys Thr His Thr Asp Phe Cys
1               5                   10

<210> SEQ ID NO 123
<211> LENGTH: 13
<212> TYPE: PRT
<213> ORGANISM: Artificial sequence
<220> FEATURE:
<223> OTHER INFORMATION: Synthetic sequence: Kallikrein binder
    containing a WPAR motif

<400> SEQUENCE: 123

Cys Met Trp Pro Ala Arg Cys Met His Gln Asp Leu Cys
1               5                   10

<210> SEQ ID NO 124
<211> LENGTH: 13
<212> TYPE: PRT
<213> ORGANISM: Artificial sequence
<220> FEATURE:
<223> OTHER INFORMATION: Synthetic sequence: Kallikrein binder
    containing a WPAR motif

<400> SEQUENCE: 124

Cys Ala Trp Pro Ala Arg Cys Thr His Ala Asp Leu Cys
1               5                   10

<210> SEQ ID NO 125
<211> LENGTH: 13
<212> TYPE: PRT
<213> ORGANISM: Artificial sequence
<220> FEATURE:
<223> OTHER INFORMATION: Synthetic sequence: Kallikrein binder
    containing a WPAR motif

<400> SEQUENCE: 125

Cys Gln Trp Pro Ala Arg Cys Met His Gln Asp Met Cys
1               5                   10

<210> SEQ ID NO 126
<211> LENGTH: 13
<212> TYPE: PRT
<213> ORGANISM: Artificial sequence
<220> FEATURE:
<223> OTHER INFORMATION: Synthetic sequence: Kallikrein binder
    containing a WPAR motif

<400> SEQUENCE: 126

Cys Gln Trp Pro Ala Arg Cys Thr His Ser Asp Leu Cys
1               5                   10

```
<210> SEQ ID NO 127
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 127

Cys Leu Trp Pro Ala Arg Cys Thr His Ala Asp Leu Cys
1               5                   10

<210> SEQ ID NO 128
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 128

Cys Arg Trp Pro Ala Arg Cys Thr His Gln Asp Leu Cys
1               5                   10

<210> SEQ ID NO 129
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 129

Cys Gln Trp Pro Ala Arg Cys Met His Gln Glu Leu Cys
1               5                   10

<210> SEQ ID NO 130
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 130

Cys Thr Trp Pro Ala Arg Cys Leu His Gln Asp Leu Cys
1               5                   10

<210> SEQ ID NO 131
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 131

Cys Ser Trp Pro Ala Arg Cys Thr His Ser His Leu Cys
1               5                   10

<210> SEQ ID NO 132
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 132
```

Cys Val Trp Pro Ala Arg Cys Thr His Gln Asp Leu Cys
1               5                   10

<210> SEQ ID NO 133
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 133

Cys Thr Trp Pro Ala Arg Cys Thr His Ala Asp Leu Cys
1               5                   10

<210> SEQ ID NO 134
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 134

Cys His Trp Pro Ala Arg Cys Met His Gln Asp Leu Cys
1               5                   10

<210> SEQ ID NO 135
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 135

Cys Pro Trp Pro Ala Arg Cys Thr His Thr Asp Leu Cys
1               5                   10

<210> SEQ ID NO 136
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 136

Cys Ala Trp Pro Ala Arg Cys Thr His Tyr Asp Leu Cys
1               5                   10

<210> SEQ ID NO 137
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 137

Cys Pro Trp Pro Ala Arg Cys Thr His Gln Asn Leu Cys
1               5                   10

<210> SEQ ID NO 138
<211> LENGTH: 13
<212> TYPE: PRT
<213> ORGANISM: Artificial sequence

```
<220> FEATURE:
<223> OTHER INFORMATION: Synthetic sequence: Kallikrein binder
      containing a WPAR motif

<400> SEQUENCE: 138

Cys Ser Trp Pro Ala Arg Cys Thr His Thr Glu Leu Cys
1               5                   10

<210> SEQ ID NO 139
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 139

Cys Ala Trp Pro Ala Arg Cys Met His Asp Asp Leu Cys
1               5                   10

<210> SEQ ID NO 140
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 140

Cys Ser Trp Pro Ala Arg Cys Leu His Thr Glu Leu Cys
1               5                   10

<210> SEQ ID NO 141
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 141

Cys Ser Trp Pro Ala Arg Cys Ile His Gln Asp Leu Cys
1               5                   10

<210> SEQ ID NO 142
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 142

Cys Thr Trp Pro Ala Arg Cys Thr His Thr Asp Met Cys
1               5                   10

<210> SEQ ID NO 143
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 143

Cys Ala Trp Pro Ala Arg Cys Thr His Thr His Leu Cys
1               5                   10
```

<210> SEQ ID NO 144
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 144

Cys Ala Trp Pro Ala Arg Cys Leu His Ala Asp Met Cys
1               5                   10

<210> SEQ ID NO 145
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 145

Cys Ala Trp Pro Ala Arg Cys Leu His Gln Asp Trp Cys
1               5                   10

<210> SEQ ID NO 146
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 146

Cys Asp Trp Pro Ala Arg Cys Met His Gln Glu Phe Cys
1               5                   10

<210> SEQ ID NO 147
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 147

Cys Ala Trp Pro Ala Arg Cys Thr His Gln Thr Met Cys
1               5                   10

<210> SEQ ID NO 148
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 148

Cys Thr Trp Pro Ala Arg Cys Leu His Gln His Met Cys
1               5                   10

<210> SEQ ID NO 149
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

```
<400> SEQUENCE: 149

Cys Ser Trp Pro Ala Arg Cys Val His Gln Asp Met Cys
1               5                   10

<210> SEQ ID NO 150
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 150

Cys Glu Trp Pro Ala Arg Cys Leu His Thr Asp Leu Cys
1               5                   10

<210> SEQ ID NO 151
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 151

Cys Leu Trp Pro Ala Arg Cys Leu Thr Thr Glu Leu Cys
1               5                   10

<210> SEQ ID NO 152
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 152

Cys Ser Trp Pro Ala Arg Cys Thr His Ala Glu Met Cys
1               5                   10

<210> SEQ ID NO 153
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 153

Cys Arg Trp Pro Ala Arg Cys Thr His Thr Asp Leu Cys
1               5                   10

<210> SEQ ID NO 154
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 154

Cys Thr Trp Pro Ala Arg Cys Thr His Gln Ala Phe Cys
1               5                   10

<210> SEQ ID NO 155
<211> LENGTH: 13
<212> TYPE: PRT
```

```
<213> ORGANISM: Artificial sequence
<220> FEATURE:
<223> OTHER INFORMATION: Synthetic sequence: Kallikrein binder
      containing a WPAR motif

<400> SEQUENCE: 155

Cys Ser Trp Pro Ala Arg Cys Thr His Ser Asp Leu Cys
1               5                   10

<210> SEQ ID NO 156
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 156

Cys Ser Trp Pro Ala Arg Cys Leu His Asp Asp Leu Cys
1               5                   10

<210> SEQ ID NO 157
<211> LENGTH: 13
<212> TYPE: PRT
<213> ORGANISM: Artificial sequence
<220> FEATURE:
<223> OTHER INFORMATION: Synthetic sequence: Kallikrein binder
      containing a WPAR motif

<400> SEQUENCE: 157

Cys Pro Trp Pro Ala Arg Cys Leu His Thr Asp Leu Cys
1               5                   10

<210> SEQ ID NO 158
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 158

Met His Xaa Asp Leu
1               5

<210> SEQ ID NO 159
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 159

Leu His Xaa Asp Leu
1               5

<210> SEQ ID NO 160
<211> LENGTH: 5
<212> TYPE: PRT
<213> ORGANISM: Artificial sequence
<220> FEATURE:
<223> OTHER INFORMATION: Synthetic sequence: Peptide motif
```

```
<220> FEATURE:
<221> NAME/KEY: VARIANT
<222> LOCATION: (3)..(3)
<223> OTHER INFORMATION: Xaa is any amino acid

<400> SEQUENCE: 160

Thr His Xaa Glu Leu
1               5

<210> SEQ ID NO 161
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 161

Thr His Xaa His Leu
1               5

<210> SEQ ID NO 162
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 162

Leu His Xaa Glu Leu
1               5

<210> SEQ ID NO 163
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 163

Thr His Xaa Asn Leu
1               5

<210> SEQ ID NO 164
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 164

Thr His Xaa Asp Trp
1               5
```

```
<210> SEQ ID NO 165
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 165

Leu His Xaa Asp Trp
1               5

<210> SEQ ID NO 166
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 166

Met His Xaa Glu Leu
1               5

<210> SEQ ID NO 167
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 167

Leu Thr Xaa Glu Leu
1               5

<210> SEQ ID NO 168
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 168

Leu Thr Xaa Asp Leu
1               5

<210> SEQ ID NO 169
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid
```

```
<400> SEQUENCE: 169

Leu His Xaa Gln Leu
1               5

<210> SEQ ID NO 170
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 170

Leu His Xaa Asp Met
1               5

<210> SEQ ID NO 171
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 171

Leu His Xaa Ser Leu
1               5

<210> SEQ ID NO 172
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 172

Thr His Xaa Ala Leu
1               5

<210> SEQ ID NO 173
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 173

Leu His Xaa His Leu
1               5

<210> SEQ ID NO 174
<211> LENGTH: 5
<212> TYPE: PRT
<213> ORGANISM: Artificial sequence
<220> FEATURE:
```

```
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 174

Leu Thr Xaa Ser Leu
1               5

<210> SEQ ID NO 175
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 175

Thr His Xaa Ser Leu
1               5

<210> SEQ ID NO 176
<211> LENGTH: 5
<212> TYPE: PRT
<213> ORGANISM: Artificial sequence
<220> FEATURE:
<223> OTHER INFORMATION: Synthetic sequence: Peptide motif
<220> FEATURE:
<221> NAME/KEY: VARIANT
<222> LOCATION: (3)..(3)
<223> OTHER INFORMATION: Xaa is any amino acid

<400> SEQUENCE: 176

Thr His Xaa Phe Leu
1               5

<210> SEQ ID NO 177
<211> LENGTH: 15
<212> TYPE: PRT
<213> ORGANISM: Artificial sequence
<220> FEATURE:
<223> OTHER INFORMATION: Synthetic sequence: Bicyclic peptide phage
      library 5x5
<220> FEATURE:
<221> NAME/KEY: VARIANT
<222> LOCATION: (3)..(7)
<223> OTHER INFORMATION: Xaa is any amino acid
<220> FEATURE:
<221> NAME/KEY: VARIANT
<222> LOCATION: (9)..(13)
<223> OTHER INFORMATION: Xaa is any amino acid

<400> SEQUENCE: 177

Ala Cys Xaa Xaa Xaa Xaa Xaa Cys Xaa Xaa Xaa Xaa Xaa Cys Ala
1               5                   10                  15

<210> SEQ ID NO 178
<211> LENGTH: 11
<212> TYPE: PRT
<213> ORGANISM: Artificial sequence
<220> FEATURE:
<223> OTHER INFORMATION: Synthetic sequence: Bicyclic peptide phage
      library 3x3 A
<220> FEATURE:
<221> NAME/KEY: VARIANT
<222> LOCATION: (3)..(5)
<223> OTHER INFORMATION: Xaa is any amino acid
```

```
<220> FEATURE:
<221> NAME/KEY: VARIANT
<222> LOCATION: (7)..(9)
<223> OTHER INFORMATION: Xaa is any amino acid

<400> SEQUENCE: 178

Ala Cys Xaa Xaa Xaa Cys Xaa Xaa Xaa Cys Ala
1               5                   10

<210> SEQ ID NO 179
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 179

Ser Cys Phe Asn Arg Cys Arg Val Pro Cys Phe
1               5                   10

<210> SEQ ID NO 180
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 180

Lys Cys Phe Thr Ala Cys Arg Val Asp Cys Phe
1               5                   10

<210> SEQ ID NO 181
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 181

Arg Cys Phe Asn Leu Cys Arg Val Gly Cys Leu
1               5                   10

<210> SEQ ID NO 182
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 182

Asp Cys Phe Gln Gly Cys Arg Val Phe Cys Ser
1               5                   10

<210> SEQ ID NO 183
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 183

Gln Cys Phe Glu Leu Cys Arg Val Val Cys Leu
1               5                   10
```

<210> SEQ ID NO 184
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 184

Met Cys Phe Asp Ser Cys Arg Val Asn Cys Thr
1               5                   10

<210> SEQ ID NO 185
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 185

Ser Cys Phe Ala Leu Cys Arg Val Pro Cys Gln
1               5                   10

<210> SEQ ID NO 186
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 186

Val Cys Phe Pro Leu Cys Arg Val Pro Cys Ile
1               5                   10

<210> SEQ ID NO 187
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 187

Val Cys Phe Gly Val Cys Arg Val Leu Cys Ala
1               5                   10

<210> SEQ ID NO 188
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 188

Lys Cys Phe Gln Ala Cys Arg Val Ser Cys Tyr
1               5                   10

<210> SEQ ID NO 189
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 189

Val Cys Phe Ser Leu Cys Arg Ala Gly Cys Leu
1               5                   10

<210> SEQ ID NO 190
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 190

Arg Cys Phe Glu Lys Cys Arg Ala Phe Cys Tyr
1               5                   10

<210> SEQ ID NO 191
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 191

Arg Cys Trp Gln Thr Cys Arg Val Ser Cys Val
1               5                   10

<210> SEQ ID NO 192
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 192

Leu Cys Trp Thr Gly Cys Arg Val Ser Cys Phe
1               5                   10

<210> SEQ ID NO 193
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 193

Gly Cys Trp Ala Pro Cys Arg Val Gly Cys Tyr
1               5                   10

<210> SEQ ID NO 194
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 194

Arg Cys Trp Thr Ala Cys Arg Gly Leu Cys Phe
1               5                   10

<210> SEQ ID NO 195
<211> LENGTH: 11

```
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 195

Asp Cys Tyr Gln Leu Cys Arg Val Ser Cys Glu
1               5                   10

<210> SEQ ID NO 196
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 196

Thr Cys Phe Arg Ser Cys Lys Val Ala Cys Tyr
1               5                   10

<210> SEQ ID NO 197
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 B
      library

<400> SEQUENCE: 197

Gln Cys Phe Gln Ala Cys Lys Thr Leu Cys Trp
1               5                   10

<210> SEQ ID NO 198
<211> LENGTH: 5
<212> TYPE: PRT
<213> ORGANISM: Artificial sequence
<220> FEATURE:
<223> OTHER INFORMATION: Synthetic peptide

<400> SEQUENCE: 198

Leu His Gln Asp Leu
1               5

<210> SEQ ID NO 199
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: SITE
<222> LOCATION: (2)..(2)
<223> OTHER INFORMATION: Xaa is homohistidine

<400> SEQUENCE: 199

Leu Xaa Gln Asp Leu
1               5

<210> SEQ ID NO 200
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: SITE
<222> LOCATION: (1)..(2)
```

```
<223> OTHER INFORMATION: Reduced amide

<400> SEQUENCE: 200

Ala His Gln Asp Leu
1               5

<210> SEQ ID NO 201
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: SITE
<222> LOCATION: (4)..(4)
<223> OTHER INFORMATION: Xaa is azetidine carboxylic acid
<220> FEATURE:
<221> NAME/KEY: SITE
<222> LOCATION: (6)..(6)
<223> OTHER INFORMATION: Xaa is homoarginine
<220> FEATURE:
<221> NAME/KEY: SITE
<222> LOCATION: (8)..(9)
<223> OTHER INFORMATION: Reduced amide pseudo peptide bond

<400> SEQUENCE: 201

Cys Ser Phe Xaa Tyr Xaa Cys Ala His Gln Asp Leu Cys
1               5                   10

<210> SEQ ID NO 202
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 202

Ala Cys Phe Lys His Cys Arg Val Ala Cys Ala
1               5                   10

<210> SEQ ID NO 203
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 203

Ala Cys Phe Pro Lys Cys Arg Val Ala Cys Ala
1               5                   10

<210> SEQ ID NO 204
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 204

Ala Cys Phe Asp Pro Cys Arg Val Ile Cys Ala
1               5                   10

<210> SEQ ID NO 205
<211> LENGTH: 11
<212> TYPE: PRT
<213> ORGANISM: Artificial sequence
```

```
<220> FEATURE:
<223> OTHER INFORMATION: Synthetic sequence: Bicyclic peptide from 3x3 A
      library

<400> SEQUENCE: 205

Ala Cys Phe Lys Asn Cys Arg Val Asn Cys Ala
1               5                   10

<210> SEQ ID NO 206
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 206

Ala Cys Phe Asn Lys Cys Arg Val Asn Cys Ala
1               5                   10

<210> SEQ ID NO 207
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 207

Ala Cys Phe Lys Gln Cys Arg Val Asn Cys Ala
1               5                   10

<210> SEQ ID NO 208
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 208

Ala Cys Phe Tyr Lys Cys Arg Val Asn Cys Ala
1               5                   10

<210> SEQ ID NO 209
<211> LENGTH: 11
<212> TYPE: PRT
<213> ORGANISM: Artificial sequence
<220> FEATURE:
<223> OTHER INFORMATION: Synthetic sequence: Bicyclic peptide from 3x3 A
      library

<400> SEQUENCE: 209

Ala Cys Phe Lys Ala Cys Arg Val Asn Cys Ala
1               5                   10

<210> SEQ ID NO 210
<211> LENGTH: 15
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (2)..(7)
<223> OTHER INFORMATION: X = any amino acid
<220> FEATURE:
<221> NAME/KEY: X
<222> LOCATION: (9)..(15)
```

<223> OTHER INFORMATION: X = any amino acid

<400> SEQUENCE: 210

Cys Xaa Xaa Xaa Xaa Xaa Xaa Cys Xaa Xaa Xaa Xaa Xaa Xaa Cys
1               5                   10                  15

<210> SEQ ID NO 211
<211> LENGTH: 7
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = any amino acid
<220> FEATURE:
<221> NAME/KEY: X
<222> LOCATION: (2)..(2)
<223> OTHER INFORMATION: X = any amino acid
<220> FEATURE:
<221> NAME/KEY: X
<222> LOCATION: (3)..(3)
<223> OTHER INFORMATION: X = tryptophan or phenylalanine
<220> FEATURE:
<221> NAME/KEY: X
<222> LOCATION: (5)..(5)
<223> OTHER INFORMATION: X = any amino acid
<220> FEATURE:
<221> NAME/KEY: X
<222> LOCATION: (6)..(6)
<223> OTHER INFORMATION: X =lysine or arginine
<220> FEATURE:
<221> NAME/KEY: X
<222> LOCATION: (7)..(7)
<223> OTHER INFORMATION: X = any amino acid

<400> SEQUENCE: 211

Xaa Xaa Xaa Pro Xaa Xaa Xaa
1               5

<210> SEQ ID NO 212
<211> LENGTH: 7
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = any amino acid
<220> FEATURE:
<221> NAME/KEY: X
<222> LOCATION: (2)..(2)
<223> OTHER INFORMATION: X = threonine or leucine
<220> FEATURE:
<221> NAME/KEY: X
<222> LOCATION: (4)..(4)
<223> OTHER INFORMATION: X = glutamine or threonine
<220> FEATURE:
<221> NAME/KEY: X
<222> LOCATION: (5)..(5)
<223> OTHER INFORMATION: X = any amino acid
<220> FEATURE:
<221> NAME/KEY: X
<222> LOCATION: (7)..(7)
<223> OTHER INFORMATION: X = any amino acid

<400> SEQUENCE: 212

Xaa Xaa His Xaa Xaa Leu Xaa
1               5

<210> SEQ ID NO 213

```
<211> LENGTH: 7
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = any amino acid
<220> FEATURE:
<221> NAME/KEY: X
<222> LOCATION: (2)..(2)
<223> OTHER INFORMATION: X = any amino acid
<220> FEATURE:
<221> NAME/KEY: X
<222> LOCATION: (4)..(4)
<223> OTHER INFORMATION: X = any amino acid
<220> FEATURE:
<221> NAME/KEY: X
<222> LOCATION: (7)..(7)
<223> OTHER INFORMATION: X = any amino acid

<400> SEQUENCE: 213

Xaa Xaa His Xaa Asp Leu Xaa
1               5

<210> SEQ ID NO 214
<211> LENGTH: 7
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = any amino acid
<220> FEATURE:
<221> NAME/KEY: X
<222> LOCATION: (4)..(5)
<223> OTHER INFORMATION: X = any amino acid
<220> FEATURE:
<221> NAME/KEY: X
<222> LOCATION: (7)..(7)
<223> OTHER INFORMATION: X = any amino acid

<400> SEQUENCE: 214

Xaa Thr His Xaa Xaa Leu Xaa
1               5

<210> SEQ ID NO 215
<211> LENGTH: 7
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = any amino acid; from 0 to 20 residues
<220> FEATURE:
<221> NAME/KEY: X
<222> LOCATION: (2)..(2)
<223> OTHER INFORMATION: X = Cys, Lys, Asp, Glu, Arg, Tyr, Ser, or
      selenocysteine
<220> FEATURE:
<221> NAME/KEY: X
<222> LOCATION: (3)..(3)
<223> OTHER INFORMATION: X = any amino acid; from 3-6 residues
<220> FEATURE:
<221> NAME/KEY: X
<222> LOCATION: (4)..(4)
<223> OTHER INFORMATION: X is Cys, Lys, Asp, Glu, Arg, Tyr, Ser, or
      selenocysteine
<220> FEATURE:
<221> NAME/KEY: X
```

```
<222> LOCATION: (5)..(5)
<223> OTHER INFORMATION: X = any amino acid; from 3 to 6 residues
<220> FEATURE:
<221> NAME/KEY: X
<222> LOCATION: (6)..(6)
<223> OTHER INFORMATION: X is Cys, Lys, Asp, Glu, Arg, Tyr, Ser, or
      selenocysteine
<220> FEATURE:
<221> NAME/KEY: X
<222> LOCATION: (7)..(7)
<223> OTHER INFORMATION: X = any amino acid; from 0 to 20 residues

<400> SEQUENCE: 215

Xaa Xaa Xaa Xaa Xaa Xaa Xaa
1               5

<210> SEQ ID NO 216
<211> LENGTH: 9
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = any amino acid
<220> FEATURE:
<221> NAME/KEY: X
<222> LOCATION: (3)..(5)
<223> OTHER INFORMATION: X = any amino acid
<220> FEATURE:
<221> NAME/KEY: X
<222> LOCATION: (7)..(9)
<223> OTHER INFORMATION: X = any amino acid

<400> SEQUENCE: 216

Xaa Cys Xaa Xaa Xaa Cys Xaa Xaa Xaa
1               5

<210> SEQ ID NO 217
<211> LENGTH: 4
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = tryptophan or phenylalanine
<220> FEATURE:
<221> NAME/KEY: X
<222> LOCATION: (3)..(3)
<223> OTHER INFORMATION: X = any amino acid
<220> FEATURE:
<221> NAME/KEY: X
<222> LOCATION: (4)..(4)
<223> OTHER INFORMATION: X = lysine or arginine

<400> SEQUENCE: 217

Xaa Pro Xaa Xaa
1

<210> SEQ ID NO 218
<211> LENGTH: 13
<212> TYPE: PRT
<213> ORGANISM: Artificial Sequence
<220> FEATURE:
<223> OTHER INFORMATION: Peptide
<220> FEATURE:
<221> NAME/KEY: X
<222> LOCATION: (2)..(2)
<223> OTHER INFORMATION: X = any amino acid
```

```
<220> FEATURE:
<221> NAME/KEY: X
<222> LOCATION: (8)..(8)
<223> OTHER INFORMATION: X = threonine or leucine
<220> FEATURE:
<221> NAME/KEY: X
<222> LOCATION: (10)..(10)
<223> OTHER INFORMATION: X = glutamine or threonine

<400> SEQUENCE: 218

Cys Xaa Trp Pro Ala Arg Cys Xaa His Xaa Asp Leu Cys
1               5                   10

<210> SEQ ID NO 219
<211> LENGTH: 5
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (3)..(4)
<223> OTHER INFORMATION: X = any amino acid

<400> SEQUENCE: 219

Thr His Xaa Xaa Leu
1               5

<210> SEQ ID NO 220
<211> LENGTH: 5
<212> TYPE: PRT
<213> ORGANISM: Artificial Sequence
<220> FEATURE:
<223> OTHER INFORMATION: Peptide motif
<220> FEATURE:
<221> NAME/KEY: X
<222> LOCATION: (1)..(1)
<223> OTHER INFORMATION: X = any amino acid
<220> FEATURE:
<221> NAME/KEY: X
<222> LOCATION: (3)..(3)
<223> OTHER INFORMATION: X = any amino acid

<400> SEQUENCE: 220

Xaa His Xaa Asp Leu
1               5

<210> SEQ ID NO 221
<211> LENGTH: 4
<212> TYPE: PRT
<213> ORGANISM: Artificial Sequence
<220> FEATURE:
<223> OTHER INFORMATION: Peptide motif

<400> SEQUENCE: 221

Trp Pro Ala Lys
1

<210> SEQ ID NO 222
<211> LENGTH: 13
<212> TYPE: PRT
<213> ORGANISM: Artificial Sequence
<220> FEATURE:
<223> OTHER INFORMATION: Peptide

<400> SEQUENCE: 222

Cys Ser Trp Pro Ala Arg Cys Leu His Gln Asp Leu Cys
1               5                   10
```